US008204302B2

(12) United States Patent
Larsen et al.

(10) Patent No.: US 8,204,302 B2
(45) Date of Patent: *Jun. 19, 2012

(54) SYSTEMS AND METHODS FOR AUTOMATICALLY DETERMINING 3-DIMENSIONAL OBJECT INFORMATION AND FOR CONTROLLING A PROCESS BASED ON AUTOMATICALLY-DETERMINED 3-DIMENSIONAL OBJECT INFORMATION

(75) Inventors: Paul A. Larsen, Midland, MI (US); James B. Rawlings, Madison, WI (US); Nicola J. Ferrier, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/047,491

(22) Filed: Mar. 14, 2011

(65) Prior Publication Data

US 2011/0222777 A1    Sep. 15, 2011

Related U.S. Application Data

(63) Continuation of application No. 11/856,537, filed on Sep. 17, 2007, now Pat. No. 7,916,935.

(60) Provisional application No. 60/826,198, filed on Sep. 19, 2006.

(51) Int. Cl.
*G06K 9/00* (2006.01)
*G06T 15/00* (2011.01)

(52) U.S. Cl. .................. 382/154; 345/419; 348/42

(58) Field of Classification Search ............ 382/154, 382/285; 345/419–427; 356/12–14; 348/42–60; 359/462–477; 352/57–65; 33/20.4; 353/7–9; 378/41–42; 396/324–331

See application file for complete search history.

(56) References Cited

U.S. PATENT DOCUMENTS

| | | | | |
|---|---|---|---|---|
| 6,995,762 | B1 * | 2/2006 | Pavlidis et al. | 345/419 |
| 7,133,551 | B2 * | 11/2006 | Chen et al. | 382/154 |
| 7,653,216 | B2 * | 1/2010 | Kanade et al. | 382/106 |
| 7,885,467 | B2 * | 2/2011 | Larsen et al. | 382/225 |
| 7,916,935 | B2 * | 3/2011 | Larsen et al. | 382/154 |
| 2003/0071811 | A1 * | 4/2003 | Iwata et al. | 345/420 |
| 2003/0147553 | A1 * | 8/2003 | Chen et al. | 382/154 |

(Continued)

OTHER PUBLICATIONS

Lowe, David G., "Three-Dimensional Object Recognition From Single Two-Dimensional Images" Artificial Intelligence, vol. 31, Issue 3, 1987, pp. 355-395.*

*Primary Examiner* — Aaron W Carter
(74) *Attorney, Agent, or Firm* — Crawford Maunu PLLC

(57) ABSTRACT

An image containing one or more types of objects to be located is analyzed to locate linear features within the image. The objects have edges having known spatial relationships. The linear features and identified virtual lines are analyzed to find groups of linear features and/or virtual lines that have one of the known spatial relationships. These relationships can include parallel edges, edges that meet at certain angles or angle ranges, the number of lines meeting a vertex and the like. The identified group is compared with projected 2-dimensional representation(s) of the object(s) to determine whether any additional lines appear in the image that are part of the located object. In various exemplary embodiments, two or more hypotheses for how the identified group of linear features maps to the 3-dimensional representation of the object can be generated. The best fitting hypothesis becomes the recognized 3-dimensional shape and orientation for that object.

23 Claims, 37 Drawing Sheets

U.S. PATENT DOCUMENTS

2006/0025888 A1* 2/2006 Gutmann et al. ............. 700/245
2007/0257910 A1* 11/2007 Gutmann et al. ............. 345/424
2008/0068379 A1* 3/2008 Larsen et al. ................. 345/427
2009/0262113 A1* 10/2009 Kotake et al. ................. 345/427

* cited by examiner

SYSTEMS AND METHODS FOR AUTOMATICALLY DETERMINING 3-DIMENSIONAL OBJECT INFORMATION AND FOR CONTROLLING A PROCESS BASED ON AUTOMATICALLY-DETERMINED 3-DIMENSIONAL OBJECT INFORMATION

RELATED PATENT DOCUMENTS

This patent document is a continuation under 35 U.S.C. §120 of application Ser. No. 11/856,537, now U.S. Pat. No. 7,916,935, which was filed on Sep. 17, 2007, which claims priority benefit under 35 U.S.C. §119 of U.S. Application No. 60/826,198 filed on Sep. 19, 2006, to which priority is also claimed here; both of these patent documents are fully incorporated herein by reference.

FEDERALLY-SPONSORED RESEARCH AND DEVELOPMENT

This invention was made with government support under 0540147 awarded by the National Science Foundation. The government has certain rights in the invention.

BACKGROUND OF THE INVENTION

1. Field of the Invention

This invention is directed to systems and methods for determining three-dimensional information about objects, such as their shapes, sizes, orientations and the like, and for systems and methods for controlling one or more processes or devices based on the determined three-dimensional object information.

2. Related Art

Suspension crystallization processes often result in crystals having a wide range of particle sizes. When crystallizing crystal-forming chemical compounds, controlling the particle size distribution (PSD) is typically highly important. For example, when the particle size distribution of high-aspect-ratio crystals is within a desired range, the efficiency of the downstream manufacturing process may be optimized or maximized. Likewise, when the particle size distribution of such high-aspect-ratio crystals is within a desired range, the overall quality of the end product being made, whether such high-aspect-ratio crystals are an intermediate product or the final end product, may be optimized or maximized.

Conventional techniques for determining the particle size distribution of a group of crystals include laser diffraction and laser backscattering, which are commonly-used on-line techniques. It should be appreciated that the drawbacks associated with these techniques discussed below are characteristic of the drawbacks associated with other techniques. T. Allen, "Particle Size Measurement, Vol. 1, 5$^{th}$ Edition", Chapman and Hall, London, 1997, discusses the conventional techniques in detail.

Laser diffraction operates by passing laser light through a quantity of the suspended crystal particles. The diffracted laser beams are diffracted onto a CCD array or the like, where the diffraction patterns are captured. Based on the captured diffraction patterns, the crystal size and particle size distribution can be determined However, the analysis algorithms developed for analyzing the diffracted patterns have all been developed based on the assumption that the particles are spherical. Spherical particles make the analysis easy, because the diffraction patterns are independent of the orientation of the crystal particles and thus are solely dependent on the size of the crystal particles. Such orientation independence is obviously an appropriate assumption only for spherical particles, or near spherical particles, such as tetrahedrons, cubes and other near spherical orientation particles that can be treated as being generally orientation independent.

Because the measured size of many types of crystals, even such near-spherical crystals, is dependent on the orientation of the crystal particles, such laser diffraction methods are limited. Additionally, because the diffraction patterns are formed by passing light through a sample, such diffraction patterns are typically inappropriate for in-situ measurements or measurements of crystal solutions having high solids concentrations, where an insufficient amount of light would actually pass through the sample and be recorded. Thus, laser diffraction can over-estimate the broadness of the spherical diameter distribution, sometimes significantly, due to such orientation effects and the spherical models used to interpret the diffraction data.

In contrast to laser diffraction, which relies on light passing through the sample, laser backscattering relies on the particles reflecting a sufficient amount of light back towards the light source. Laser backscattering provides a chord length distribution that can be related theoretically to the particle size distribution. In laser backscattering, the laser beam is rotated over the particle slurry such that each particle backscatters light as the light passes over that particle. Based on a time-to-cross measurement and the known speed of movement of the laser beam, the chord length of the laser beam's path over the crystal can be determined. The chord length distribution can only be related back to the actual size distribution of the crystals by assuming some geometry for the particles, such as an aspect ratio, a specific orientation and/or the like. However, actual in-situ crystals have an infinite number of orientations. Moreover, the aspect ratio, i.e., a length to thickness, of the crystals is one of the variables that appropriate control of the crystallization process affects. Accordingly, assumptions about the crystals' geometry render the laser backscattering analysis less than complete.

As a result of the shortcomings of laser diffraction and laser backscattering, various imaging-based systems have been developed to size high-aspect-ratio, i.e., elongated, crystals. Such imaging systems and techniques offer the potential to extract both size and shape information. Thus, such imaging based systems and techniques are a promising and attractive approach for obtaining particle size distributions for non-spherical particles. Conventional, imaging-based, on-line particle size and shape analyzers are available from Malvern and Beckman-Coulter, such as the Malvern Sysmex FPIA3000 and the Beckman-Coulter RapidVUE. *Powder Sampling and Particle Size Determination*, by T. Allen, Elsevier, 2003, surveys other imaging-based instruments.

Typically, these instruments require withdrawing a sample of the crystal slurry from the crystallization reaction vessel. Drawing such samples is inconvenient, possibly hazardous, and raises concerns about whether the sample is truly representative of the bulk slurry. One notable system that provides for in-situ sampling is the Particle Vision and Measurement (PVM) system from Lasentec, Inc. The Lasentec Particle Vision and Measurement in-situ probe is combined with automatic image analysis software that is useful for some types of crystals. However, this system does not give suitable results for high-aspect-ratio crystal particles.

U.S. patent application Ser. No. 11/237,088, which is assigned to the same assignee as the present application and which is incorporated by reference herein in its entirety, discloses systems and methods for determining a particle size distribution by obtaining and analyzing an in-situ image of the crystallization process. In particular, the 088 patent application determines a length measurement for each located crystal. A crystal is located by finding line segments within the obtained in-situ image. Line segments that appear to be part of a single crystal edge are combined to form virtual lines. Parallel line segments and/or virtual lines that meet defined relationships are identified as the edges of a given crystal. Connected components associated with the parallel line segments and/or virtual lines are combined, and a length of the combined connected component is the length size of that given crystal.

SUMMARY OF THE DISCLOSED EMBODIMENTS

Prior to the systems and methods disclosed in the 088 patent application, in-situ video microscopy has thus far been limited to quality monitoring. This has primarily been due to the nature of the in-situ images, which contain blurred, out of focus and overlapping crystal particles. Thus, the nature of the in-situ images and the available analytical tools previous to the systems and methods disclosed in the 088 patent application precluded successfully applying image analysis to automatically quantify particle size and/or shape. More broadly, prior to the systems and methods disclosed in the 088 patent application, automatically analyzing images, such as for machine vision, intelligence gathering, and the like, has required well controlled environmental parameters, such as lighting, focus, depth of field, contrast, brightness and/or the like. For example, conventional machine vision systems and methods typically required that the illumination level be known or measured, that the direction and angle of the illumination source(s) relative to the object being imaged be known, that the distance from the surface being imaged be known or controlled, and the like. In general, most conventional automatic image analysis systems and methods required very well behaved images with little noise and that the general location of the portion of the object to be imaged be known, in combination with the well-controlled lighting parameters discussed above.

In contrast, at least some embodiments of systems and methods according to this invention are able to acquire and analyze information from images of objects having relatively long and/or relatively closely-spaced linear features having one of a plurality of defined spatial relationships, where the images can be of very low quality. Such images will typically have poor contrast and/or brightness, poor focus, objects that are either incompletely in the field of view and/or that are overlapping, objects that lie at poorly defined, or even at random and/or arbitrary, locations, varying lighting conditions and/or the like.

The inventors have determined that appropriately segmenting such images, especially poor quality images, is desirable to successfully automatically analyzing such images, such as, for example, in-situ images of a crystallization process used to attempt to determine three-dimensional particle size and shape information, such as various size distributions of particles appearing in the image.

In this context, segmentation refers to separating objects of interest in the image, such as, for example, specific crystals, from the background, such as, for example, the uncrystallized reactants, the liquid solvent(s) and/or the slurry of background crystals being formed during a crystallization reaction. Of course, segmentation is always easier if the objects are imaged using transmitted light, because the outlines of the particle are easily distinguished. However, for in-situ imaging, reflected light often must be used due to the high solids concentrations that typically occur during crystallization. Accordingly, segmenting such images is substantially more difficult.

For example, "Multi-scale Segmentation Image Analysis for the In-Process Monitoring of Particle Shape with Batch Crystallizers", J. Calderon De And a et al, Chem. Eng. Sci., 60: 1053-1065, 2005, discloses a technique for automatically segmenting in-process suspension crystallizer images. This technique was only demonstrated on images that appeared to have been acquired at low solids concentrations where there are no overlapping particles and the particles edges are fairly well defined. Similarly, "In Situ Visualization of Coal Particle Distribution in a Liquid Fluidized Bed Using Fluorescence Microscopy", E. Kaufman et al, Powder Tech., 78: 239-246, 1994, discloses an in-situ fluorescence imaging method, where the liquid phase of a fluidized bed was made to fluoresce while leaving the coal particles opaque. This enabled a gray-level threshold method to be used to detect the particle edges. However, for more dense particle volume fractions, the inventors had to manually determine which of these segmented particles could be used for sizing.

This invention provides systems and methods for analyzing even low quality images of objects having edge features having known spatial relationships.

This invention separately provides systems and methods for analyzing images of objects having relatively long and/or relatively closely-spaced edge features.

This invention separately provides systems and methods for analyzing images of objects having edge features having defined angular relationships.

This invention separately provides systems and methods for segmenting objects having edge features having known spatial relationships from other portions of the image.

This invention separately provides systems and methods for segmenting objects having relatively long and/or relatively closely-spaced edge features from other image portions.

This invention separately provides systems and methods for segmenting objects having edge features having defined angular relationships from other image portions.

This invention separately provides systems and methods for segmenting objects, appearing in low quality images, that are generally insensitive to lighting conditions.

This invention separately provides systems and methods for reliably locating objects in an image generally independently of brightness and/or contrast levels in the image.

This invention separately provides systems and methods for analyzing in-situ images of objects having edges having known spatial relationships.

This invention separately provides systems and methods for segmenting an in-situ image of objects having edges having known spatial relationships.

This invention separately provides systems and methods for identifying areas, within an in-situ image of objects having edges having known spatial relationships, that represent the objects.

In various exemplary embodiments of systems and methods according to this invention, an image of objects having edges having known spatial relationships, such as an in-situ image of crystals having a known crystal form and/or habit, are first analyzed to locate linear features within the image. In various exemplary embodiments, Burns direction analysis is used to locate these linear features. Connected pixels having the same general gradient direction are grouped into line support regions and a linear feature is determined for each line support region.

In various exemplary embodiments, the linear features are analyzed to identify longer linear features and/or two or more shorter linear features that are effectively co-linear. One or more virtual lines that represent these longer linear features or the combination of these two or more shorter co-linear lines are determined based on the various linear features. The linear features and virtual lines, or more generally, line-like features, are then analyzed to find groups of two or more linear features and/or virtual lines that have one of the plurality of defined angular relationships, for the particular crystal form and/or habit of the crystals being formed. Such defined angular relationships include edges that are parallel, edges that meet at certain angles or angle ranges, the number of lines meeting a vertex and the like. Based on the nature of the object, these relationships can include that the linear features and/or virtual lines overlap an appropriate amount and/or are spaced an appropriate distance apart.

In various exemplary embodiments, to find the underlying virtual lines, each pair of linear features is analyzed to determine if that pair of linear features is co-linear or overlapping. Groups of the located linear features and/or virtual lines are then clustered into viewpoint-invariant line groups, or VIGs, based on the defined angular relationships that can occur for a given object's 3-dimensional shape.

In various exemplary embodiments, the linear features and/or virtual lines of the identified group are compared with a wire frame or other appropriate 3-dimensional representation of the object to be located in the image to determine whether there are any additional linear features and/or virtual lines appearing in the image that are part of the located object. In various exemplary embodiments, two or more hypotheses for how the identified group of linear features and/or virtual lines maps to the 3-dimensional representation of the object can be generated. For each hypothesis, the image is analyzed to identify additional linear features and/or virtual lines in the image that are part of the located object based on that hypothesis. The best fitting hypothesis becomes the recognized 3-dimensional shape and orientation for that object.

In various exemplary embodiments, additional linear features and/or virtual lines that appear to correspond to additional edges of the object to be located are combined with the set of linear features and/or virtual lines that have the appropriate relationship to form the group of linear features and/or virtual lines that correspond to and/or are associated with, the projected, fitted model.

In various exemplary embodiments, the determined orientation and/or dimensional information for a plurality of objects is analyzed to determine statistical information about the plurality of objects. In various exemplary embodiments, the orientation, dimensional and/or statistical information is used to monitor one or more processes associated with the objects, to control one or more processes associated with the objects, to reject the objects or a structure or device comprising the objects, or the like.

For example, one or more statistical measures can be determined for the determined parameters' dimensional information, orientation and/or the like for the representative shapes, such as distribution, mean, median and/or the like of, size, length, width, area, orientation or the like. Based on these statistical measures, one or more process control variables can be modified. Alternatively, a determination can be made whether the process has reached a sufficient completion stage such that the objects can be passed on to a downstream process, if the objects are appropriate for further processing or sale, or the like.

In various exemplary embodiments, an image analysis system according to this invention includes an image segmentation circuit, routine or application, a linear feature clustering circuit, routine or application, a parameter determining circuit, routine or application, a statistical value determining circuit, routine or application, and a control signal determining circuit, routine or application. In various exemplary embodiments, these control signals are output to a process control device, a material handling system, an attention indicating system, or the like.

These and other features and advantages or various exemplary embodiments of systems and methods according to this invention will be described in greater detail below with respect to the exemplary embodiments shown in the attached figures.

BRIEF DESCRIPTION OF DRAWINGS

Various exemplary embodiments of the systems and methods according to this invention will be described in detail, with reference to the following Figures, wherein.

DETAILED DESCRIPTION OF DISCLOSED EMBODIMENTS

Figure 1:
FIG. 1 illustrates various types of crystals.

Various systems and methods according to this invention are usable to locate objects having a defined 3-dimensional shape profile in any image. Various exemplary embodiments of systems and methods according to this invention are particularly useable to locate objects having known dimensions and/or dimensional relationships in very noisy and/or low quality images. In general, "low quality" images are those images where the foreground objects are difficult to distinguish from the background of the image and/or various foreground images are difficult to distinguish from each other. Such "low quality" images typically have inappropriate contrast and/or brightness levels, are out of focus, and/or are full of non-image artifacts, such as moire patterns, noise, various image distortions and the like. In general, in various exemplary embodiments of systems and methods according to this invention, objects within the image can be identified and segmented without regard to the contrast and/or brightness levels of the image. Thus, various exemplary embodiments of systems and methods according to this invention can locate objects from images that have less than ideal contrast, brightness, focus and/or other lighting parameter values and/or that were acquired with less than optimal focus and/or lighting parameter values for the particular objects of interest and/or for the background or foreground objects appearing within the image.

For ease of understanding and explanation, the following detailed description of specific exemplary embodiments of systems and methods according to this invention will be described with respect to locating and segmenting crystal particles appearing within an image obtained by in-situ sampling of the crystallization process occurring within a reaction vessel. Likewise, for ease of understanding and explanation, the shape information obtained from such located and segmented crystals within the image and the statistical information obtained from a plurality of such crystals segmented from the image are used to control and/or monitor various aspects of the crystallization process.

However, it should be appreciated that the systems and methods according to this invention are not limited to in-situ images of crystal particles nor to controlling and/or monitoring such crystallization processes. Rather, it should be appreciated that systems and methods according to this invention can be applied to locate and segment other objects having a known shape profile from an image containing such objects and/or can be used to analyze one or more of those objects for individual shape information or the like and/or for statistical information about the group of objects. This individual and/or statistical information can be used in various exemplary embodiments of systems and methods according to this invention to inform various actions that can be taken with respect to the objects, such as monitoring, process control, material handling, inspection and the like.

Likewise, it should be appreciated, that in various exemplary embodiments of systems and methods according to this invention, objects of a given 3-dimensional shape profile can be identified and segmented from an acquired image, even if that image is of rather low quality and/or is relatively noisy. It should further be appreciated that any other image of one or more objects, beyond in-situ images, where the brightness, the contrast, the lighting conditions, the focus, and/or any other parameter that affects the quality of the image, can vary in unknown and/or uncontrolled ways, can also be analyzed using systems and methods according to this invention.

Thus, while the following detailed description focuses primarily on crystal particles, it should be appreciated that the subject matter of this invention is not limited to such exemplary embodiments. Therefore, various exemplary embodiments of systems and methods according to this invention can be directed to analyzing images, to segment, identify and/or locate (or the like) objects having known 3-dimensional shapes, dimensions, spatial relationships and/or dimensional relationships.

FIG. 1 shows three different crystals having different basic crystal shapes. In particular, FIG. 1(a) shows a crystal having a central body that is a polyhedral prism and that is capped by two "pyramidal" polyhedrons. In particular, the central body is wider than it is tall, in that it has a thickness $T_1$ that is greater than its body length $L_1$. FIG. 1(b) shows a second crystal having a shape that can be described as octahedral or bipyramidal. FIG. 1(c) shows a high aspect ratio, rod-like, needle-like or acicular crystal. In particular, the crystal shown in FIG. 1(c) has a length L that is approximately six times its thickness T.

In each of the images shown in FIGS. 1(a), 1(b) and 1(c), the images can be quite noisy and of sufficiently poor quality, such that it is difficult to discern the object. Because each of the crystals shown in FIGS. 1(a)-1(c) have a plurality of parallel edges visible in these images, the systems and methods disclosed in the incorporated 088 patent application can be used, with appropriate modifications to the parameter values, to locate various ones of the crystals appearing in each image.

However, the systems and methods disclosed in the incorporated 088 patent application are focused on parallel lines and generate only a length measure for the located crystals. It would be advantageous to identify the object to be located using other types of line relationships and/or to generate other information about the located objects, such as shape, thickness and/or width, aspect ratio, orientation and/or any other appropriate information.

Accordingly, the inventors have developed novel image-based systems and methods that are usable to analyze even low-quality images to extract or segment objects from the surrounding background and/or foreground portions of the image. Once the objects are segmented from the image, shape, size, orientation and/or other relevant information can be determined for individual objects, and statistical information about the objects, such as numbers, orientations, shapes, dimensions and/or other relevant parameters about the objects can be developed. For example, for crystals, such images can be analyzed to determine lengths, widths, aspect ratios and other shape and dimensional information, which can be used to develop particle size distributions and the like.

Figure 2:
FIG. 2 illustrates a representative image to be analyzed.
Figure 3:
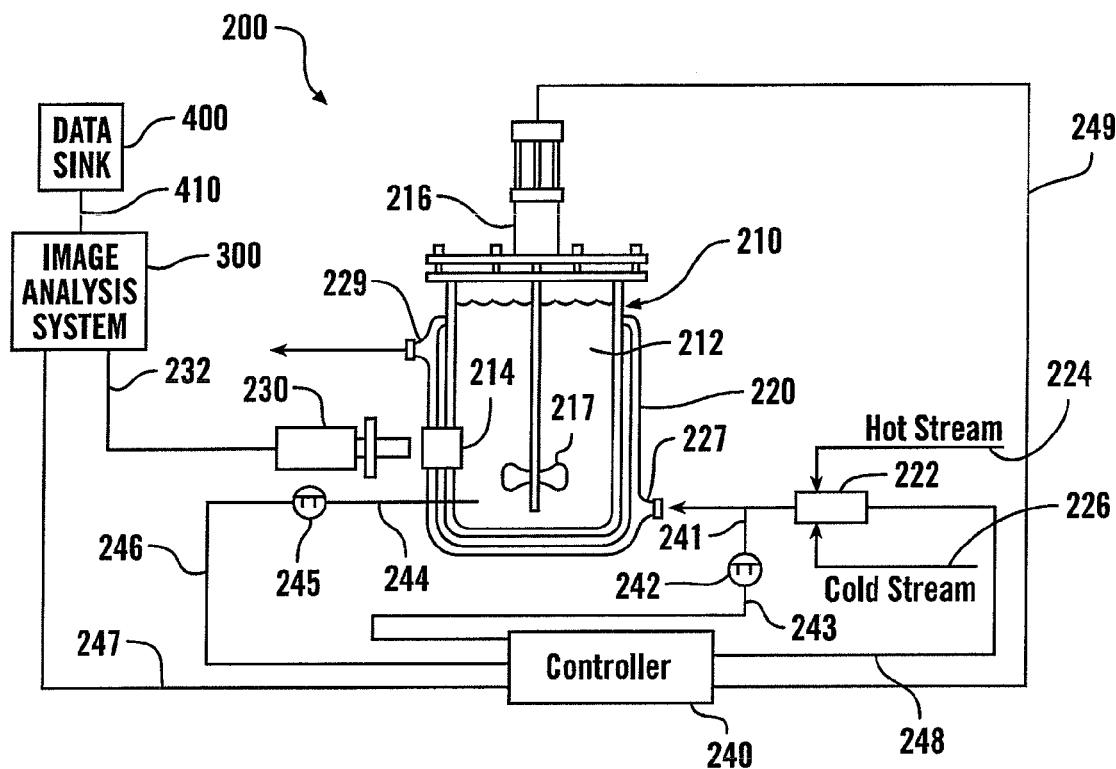
FIG. 3 illustrates one exemplary embodiment of a process control system that incorporates one or more exemplary embodiments of systems and methods according to this invention.

FIG. 2 shows one exemplary embodiment of an image 100 that is typically obtained using the system 200 shown in FIG. 3. In particular, the image shown in FIG. 2 is an image of a plurality of crystals that are growing within a reaction vessel at the time the image 100 was captured. In particular, the in-situ image 100 includes a portion 110 that includes a sample crystal. In particular, the image shown in FIG. 2 is of very low quality, in that the objects in this image are generally out of focus. Additionally the contrast and brightness are generally inappropriate, making it difficult to distinguish individual crystals in the foreground of the image from each other and from the background of the image. Because the image is out of focus, the contrast is too low, and the brightness is too high, the edges of the crystals are diffuse and difficult to identify, even by hand.

FIG. 3, as outlined above, illustrates one exemplary embodiment of a system 200 that is useable to perform a suspension crystallization process, as well as to capture an in-situ image of that process and to analyze that image to ultimately obtain information on the crystallization process, including particle size distribution and the like. As shown in FIG. 3, the system 200 includes a reaction vessel 210 having a reaction space or interior 212. The reaction vessel 210 is surrounded by a temperature control jacket 220. In a crystallization process, a solution from which at least one component is to be crystallized is placed into the reaction space 212. A digital camera or other digital image capture device 230 is arranged adjacent to an optical flat 214 of the reaction vessel 210 so that the digital camera or other digital image capture device 230 can capture an image of the interior 212 of the reaction vessel 210. The image capture device 230 outputs a captured digital image as an array of pixels over a signal line 232 to an image analysis system 300. The image analysis system 300, which will be described in greater detail below, analyzes the digital image provided by the image capture device 230 and generates one or more process and/or device control signals and/or one or more sets of statistical information about the crystallization process occurring within the reaction vessel 210. This information can either be output over a signal line 247 to the controller 240 and/or can be output over a signal line 410 to a data sink 400.

As indicated above, the reaction vessel 210 includes a reaction space 212 in which a solution containing a chemical to be precipitated out as crystals is placed. The optical flat or optical device or other viewing structure 214 provides a generally transparent and generally distortion-free view into the reaction space 212 of the reaction vessel 210 and is formed in the side of the reaction vessel 210. For large, production-size reaction vessels 210, the reaction vessel will have a transparent window adjacent to the optical flat to allow a view into the interior 212. Of course, the window and the optical flat can be combined into a single structure. However, if the reaction vessel is clear, as is common with small, research-oriented reaction vessels, no window into the interior 212 of the reaction vessel 210 is needed. An impeller 217, driven by an external impeller motor 216, is positioned in the reaction space 212 of the reaction vessel 210. The impeller 217 is useable to stir the solution placed inside the interior 212 of the reaction vessel 210.

The temperature control jacket 220 typically extends around the entire exterior of the reaction vessel 210, possibly except in the location of the optical flat or other optical device 214. The temperature control jacket 220 typically has a hollow interior having an inlet 227 and an outlet 229. A temperature control fluid, such as water or the like, can be introduced through the inlet 227 to raise, maintain, or cool the temperature of the solution placed in the reaction space 212 of the reaction vessel 210. As shown in FIG. 3, a mixing valve 222 is connected to the inlet 227. A cold fluid supply line 226 and a warm fluid supply line 224 are each connected to the mixing valve 222 and supply, respectively, cold and warm temperature control fluid to the mixing valve 222. Depending on the position of the mixing valve 222, various proportions of the hot and cold temperature control fluids are mixed together to provide a desired flow, at a desired temperature, of the temperature control fluid from the mixing valve 222 through the inlet 227 into the interior of the temperature control jacket 220 and out through the outlet 229.

The controller 240 is also connected to a pair of temperature sensors 242 and 245 over a pair of signal lines 243 and 246, respectively. The temperature sensors 242 and 245 are connected to temperature probes 241 and 244, respectively. The controller 240 inputs the sensed temperature information from the temperature sensors 242 and 245, along with the process control signals and/or the statistical information from the image analysis system 300 over the signal line 247, and outputs various process and/or device control signals, including control signals over the signal lines 248 and 249 to the mixing valve 222 and/or to the impeller motor 216. Based on the control signals output on the signal lines 248 and 249 from the controller 240, the controller 240 can, among other actions, turn on the impeller motor 216 and/or can adjust the temperature of the temperature control fluid flowing through the jacket 220.

In operation, after a solution to be crystallized is introduced in to the reaction space 212 of the reaction vessel 210, the solution is typically slowly cooled by controlling the temperature of the temperature control fluid flowing through the inlet 227 into the interior of the temperature control jacket 220. As the temperature of the solution is reduced gradually, at least one of the chemicals or components in the solution begins crystallizing. As the crystallization process continues, various images of the state of the crystallization process are captured using the image capture device 230. The images are transmitted from the image capture device 230 over the signal line 232 to the image analysis system 300, which analyzes the images and generates various process information signals, which are output over the signal line 247 to the controller 240. As the crystallization process continues, temperature signals over the signal lines 243 and 246 and the process information signals over the signal line 247 are combined by the controller 240 to generate control signals, for example, to adjust the temperature of the fluid flowing from the mixing valve 222 into the inlet 227 or to control the impeller 216. In many crystallization processes, the controller 240 at least in part operates the mixing valve 222 and/or the impeller 216 to maintain the aspect ratio of the crystals within a desired range.

As outlined above, the image capture device 230 captures in-situ images of the state of the crystallization process. These images are digital images comprising a 2-dimensional array of pixels, where each pixel has a grayscale or intensity value, which is typically a value between 0 and 255 ($2^8$ values). This image data is output to the image analysis system 300 over the signal line 232. The image analysis system 300 analyzes the digital image to locate probable crystals within the image, to extract information about those crystals from the image, and possibly to generate one or more statistical values based on the various shape parameters.

It should be appreciated that, in various exemplary embodiments, the image analysis system 300 can generate other types of signals that can be used in addition to, or in place of, the process information signals output on the signal line 247 to the controller 240. For example, the image analysis system 300 can be designed to output, after analyzing the captured in-situ images, extracting the desired information from the images and generating and analyzing statistical values, signals that trigger alarms to personnel monitoring the crystallization process. Such alarms can indicate that more interactive control of the process by the monitoring personnel is required, that the crystallization process can no longer be automatically monitored and controlled, or that the crystallization process has failed in some manner. Such signals can also be used to indicate that the crystallization process has completed. Such signals can alert the monitoring personnel, who transfer the contents of the reaction vessel 210 to a downstream process and replenish the contents of the reaction space 212 with additional solution to be crystallized. These signals can also be output to the controller 240 or another controller, either of which can automatically cause the content of the reaction space 212 to be transferred to a downstream process and the reaction space 212 prepared to receive, and/or provided with, another charge of solution to be crystallized.

The image analysis system 300 can also output the parameter information and/or the statistical information to a data sink 400 over a signal line 410. This data sink 400 can be a memory or other device usable to indefinitely store that information, and/or some other device designed to analyze that information and generate one or more control signals or the like, similarly to the controller 240. In general, the data sink 400 can be any known or later device that is able to use information that can be output by the image analysis system 300.

It should be appreciated that the image analysis system 300 can be implemented using any known or later developed device or system of devices, including an application-specific integrated circuit (ASIC) or other integrated circuit structure, a hardwired electronic or logic circuit such as a discrete element circuit, a programmable logic device such as a PLD, PLA, FPGA or PAL, a suitably-programmed digital signal processor (DSP), a suitably-programmed micro-controller, a suitably-programmed microprocessor, a suitably-programmed special-purpose or general-purpose computer or the like, possibly along with one or more related peripheral integrated circuit elements.

When implemented using hardware elements, various exemplary embodiments of the image analysis system 300 will typically include circuit or other hardware structures corresponding to one or more of an image segmenting circuit, a linear feature analyzing circuit, a viewpoint-invariant line group clustering circuit, a hypothesis generating circuit, an object model fitting circuit, a model projecting circuit, a hypothesis scoring circuit, a parameter determining circuit, a statistical measure determining circuit, and/or a control and/or information signal output circuit. When implemented using firmware and/or software elements, various exemplary embodiments of the image analysis system 300 will typically include one or more sets of one or more instructions, including one or more of: instructions for segmenting the acquired image, instructions for analyzing linear features, instructions for clustering lines into viewpoint-invariant line groups, instructions for generating hypotheses, instructions for fitting an object model to a viewpoint-invariant line group, instructions for generating a 2-dimensional projection of the fitted model, instructions for scoring a hypothesis, instructions for determining parameters for the segmented or clustered areas of the image, instructions for generating one or more statistical measures and/or instructions for generating and/or outputting control and/or information signals.

It should be appreciated that these instructions can be organized in any known or later developed form, such as, for example, routines and/or subroutines, objects, applications, procedures, managers and/or any other known or later developed software structure. The instructions can be compiled, and thus suitable for direct execution by a processor, or can be interpreted by an intermediate program executing on a processor.

It should be appreciated that a routine, an application, a manager, a procedure, an object or other known or later developed software structure can be a self-consistent sequence of computerized steps that lead to a desired result. These steps can be defined by and/or in one or more computer instructions stored in a computer readable medium, which encompasses using a carrier wave or the like to provide the software instructions to a processor. These steps can be performed by a processor executing the instructions that define the steps. Thus, the terms "routine", "application", "manager", "procedure", and "object" can refer to, for example, a sequence of instructions, a sequence of instructions organized within a programmed procedure or a programmed function, and/or a sequence of instructions organized within programmed processes executing in one or more computers. Such routines, applications, managers, procedures, objects or other known or later developed software structure can also be implemented directly in circuitry that performs the procedure.

In general, any device, system or structure, which is capable of implementing a finite state machine, that is in turn capable of implementing various ones of the flowcharts shown in FIGS. 4, 5, and 7-18 and/or processes or methods described below, can be used to implement the image analysis system 300. It should be appreciated that methods according to this invention can be performed by a computer executing one or more appropriate programs, by special purpose hardware designed to perform such methods, or any combination of such hardware, firmware and software elements.

It should further be appreciated that the image analysis system 300 can be combined with either or both of the image capture device 230 and/or the controller 240. For example, the image analysis system 300 and the controller 240 could both be implemented using a single programmed processor and related peripheral integrated circuit elements, such as in a desktop or laptop computer, a server, a network of computers, the Lasentec Particle Vision and Measurement (PVM) system or similar systems, the Malvern Sysmex FPIA3000 system or similar systems and the Beckman-Coulter RapidVUE system or similar systems and the like, which could also incorporate the camera hardware.

It should also be appreciated that, in various other exemplary embodiments of systems and methods according to this invention, material and processes other than crystals in a crystallization process can be the subjects of systems and methods according to this invention. For example, many products obtain strength and other desirable material properties based on the constituent material being essentially randomly distributed, such that the orientations of the material object are distributed equally in all directions. For example, "felts" of various materials, such as paper, fabrics, engineered wood products and the like, obtain strength and other desirable material properties in this manner. Typically, the constituent objects of these products have known dimensions or dimensional relationships.

Accordingly, systems and methods according to this invention can analyze images of these products to locate and segment such constituent objects, extract shape information about those objects and generate statistical information about those objects, such as the distribution or orientations of the objects. Based on the statistical information, the images can be used to inspect the products and determine if the products pass inspection or must be rejected. Such information can also be used to provide process control feedback signals and/or to monitor the production processes, as outlined above with respect to the crystals and the reaction of the reaction vessel 210. In general, regardless of the source of the image data, systems and methods according to this invention can be used to segment such objects having known dimensional and/or spatial relationships.

Figure 4:
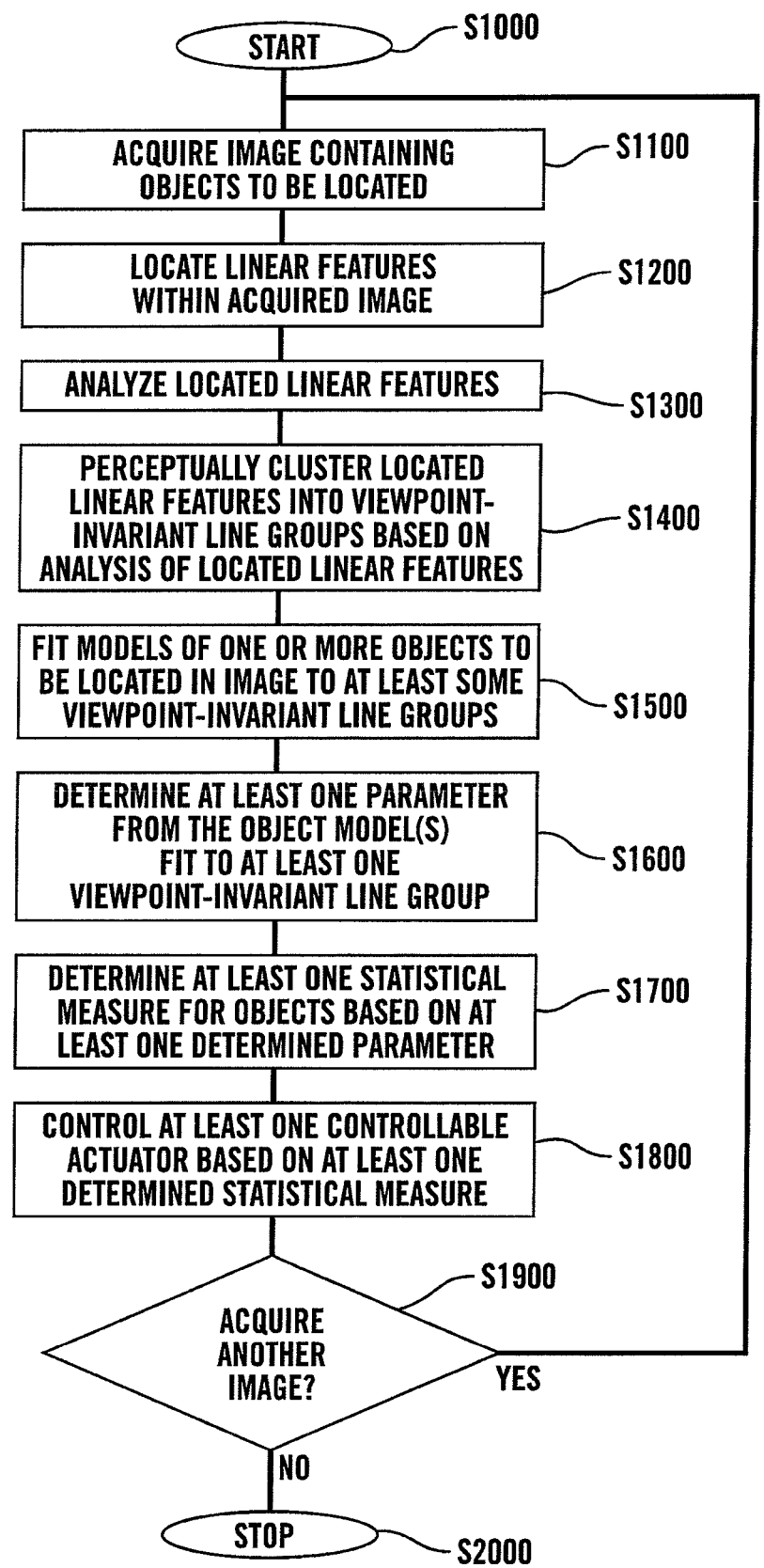
FIG. 4 is a flowchart outlining one exemplary embodiment of a method for identifying objects in an image and of a method for controlling process parameters based on the identified objects according to this invention.

FIG. 4 is a flowchart outlining one exemplary embodiment of a method for analyzing images of objects having known spatial and/or dimensional relationships, and for using information extracted from such images. For ease of understanding and explanation, the following detailed descriptions of the various flowcharts outlining exemplary embodiments of methods according to this invention are directed to analyzing images containing crystals. However, it should be appreciated that the images being analyzed are not limited to images of crystals, as outlined above. It should also be appreciated that the terms "lines" and "line-like features" are intended to include both located linear features and generated virtual lines.

As shown in FIG. 4, beginning in step S1000, operation of the method continues to step S1100, where an image, such as an in-situ crystallization image of a crystallization process occurring within a reactor vessel or a low quality image of a plurality of general objects, is acquired. Then, in step S1200, a plurality of linear features are located within the acquired image. Next, in step S1300, the located linear features are analyzed. Operation then continues to step S1400.

In step S1400, sets of located linear features are clustered into viewpoint-invariant line groups based on the analyses of the located lines, that is, the located linear features and/or the generated virtual lines, that were generated in step S1300. Next, in step S1500, one or more models of one or more objects to be located in the image are fit to at least some of the viewpoint-invariant line groups generated in step S1400. Then, in step S1600, at least one parameter is determined from each object model that has been fit to a particular viewpoint-invariant line group. It should be appreciated that, in various exemplary embodiments, these parameters can be, but are not limited to, the length, width, height, shape and/or orientation of the instance of the object model that has been fit to a particular viewpoint-invariant line group, a representative area of image portions associated with the first model, aspect ratio of the fit model, or the like. Operation then continues to step S1700.

In step S1700, at least one statistical measure for the crystals within the reactor vessel can be determined based on the at least one determined parameter for the sets of clustered linear features. Then, in step S1800, at least one controllable actuator, process variable, alarm and/or the like is controlled based on at least one of the at least one determined statistical measure and/or at least one of the at least one determined parameter. For example, in the system 200 shown in FIG. 3, at least one process variable for the crystallization process occurring within the reactor vessel can be modified based on at least one of the at least one determined statistical measure and/or at least one of the at least one determined parameter. It should be appreciated that, in the process shown in FIG. 3, the process variable can be cooling temperature, cooling rate, stirring rate or the like. The process variable can also be an indication of whether the crystallization process has completed or not. It should be appreciated that any useful process variable that affects and/or controls the crystallization process can be modified according to this invention. Next, in step S1900, a determination is made whether another image is to be acquired. If so, operation returns to step S1100. Otherwise, operation continues to step S2000, where operation of the method ends.

It should be appreciated that, in various other exemplary embodiments, the controllable actuator can be a valve, a material handling system, a motor, a pump, a compressor or the like. For example, in the system 200 shown in FIG. 2, the controllable actuator can include the mixing valve 222, the impeller 216, a drain valve useable to remove the contents of the reaction space 212, a supply valve useable to supply a new charge of solution to the reaction space 212 or the like. Alternatively, one or more alarms can be triggered, such as an indicating device being activated, to acquire the attention of one or more monitoring personnel. It should also be appreciated that, if the statistical information is not desired or needed, step S1700 can be omitted.

The exemplary method according to this invention outlined above with respect to FIG. 4, and especially steps S1200-S1400, is based on the assumption that the object to be extracted or segmented has edges or other line-like features that have known spatial and/or dimensional relationships. For example, a high-aspect-ratio, rod-like or needle-like object can be approximated as a group of two or more spatially adjacent lines having similar spatial orientations and similar lengths. It should be appreciated that other types of objects can have other types of known spatial or dimensional relationships. For example, while needle-like or rod-like objects, such as crystals, have edges that are generally relatively long, substantially parallel over their length, and spaced closely together, other types of objects may have other spatial and/or dimensional relationships.

For example, polyhedral objects will typically have edges that are within a defined range of angular orientations to each other, that have end points that are within a defined proximity of each other, have parallel edges that overlap for a significant portion of their length, and/or that have a defined range of possible lengths or relative lengths. It should be appreciated that, as long as the relationships of the edges of the objects can be well defined and will appear in the image generally over defined or definable ranges, systems and methods according to this invention can be used to locate and segment such objects from the background and/or foreground portions of the acquired image. Accordingly, in step S1200, the image is inspected to identify image features. Then, in steps S1300 and S1400, the identified image features are analyzed to identify groups of the located image features that satisfy the particular spatial and/or dimensional relationships for the particular object to be located in the image.

Line segments are commonly used as inputs to higher-level processes in automated image analysis methods. Accordingly, many different methods have been developed for extracting line segments from images. These methods can be roughly divided in to three categories: 1) Hough-transform based methods, 2) methods based on edge-linking followed by line segment grouping, and 3) gradient-based methods. Various exemplary embodiments of systems and methods according to this invention use a particular type of gradient-based method, the Burns line finder, as disclosed in "Extracting Straight Lines," J. B. Burns et al, IEEE Trans. Pattern Anal. Machine Intell., 8(4); 425-455, July 1986, which is incorporated herein by reference in its entirety. The inventors have discovered that, for the range of images, including low quality, noisy images, for which systems and methods according to this invention are particularly useful, the Burns line finder is advantageous over Hough-transform based methods, because it is scale-independent, has lower computational and memory requirements, and finds line end points more readily. The Burns line finder is unique in that it detects lines on the basis of image intensity gradient direction, whereas most line-finders are based on image intensity gradient magnitude. Accordingly, the Burns line finder is able to detect subtle linear features that would be missed by other line finding techniques.

As outlined above, images analyzable using systems and methods according to this invention include in-situ images acquired by viewing the interior of the reaction vessel 210 through the optical flat 214. Typically, a light source is directed through the optical flat 214 and the light reflecting off the various crystals within the reaction space 212 of the reaction vessel 210 is directed back to the image capture device 230. It should be appreciated that the amount of light directed back to the image capture device 230, i.e., the brightness of the image, and the contrast in the image, are typically functions of the instantaneous solids concentration within the solution within the reaction vessel 210.

That is, when most of the chemicals are still in solution and few crystals have formed, the absence of opaque, reflective material results in only a small amount of light being reflected and returning to the image capture device. Thus, the images typically are dim. As the crystallization reaction continues, the solids concentration of the solution continues to increase, as do the number and size of the crystals. As the solids concentration increases, less of the light penetrates deeply in to the reaction vessel 210. In addition, the light that does penetrate into the reaction vessel 210 typically reflects off a crystal suspended in the crystallization solution. This light is rarely directed back towards the image capture device 230. Rather, this light is typically reflected laterally or deeper in to the solution.

Thus, as the solids concentration increases, both the brightness and the overall contrast in the image can change significantly. Because the contrast and brightness of the image vary substantially during the crystallization process, methods that rely on the contrast magnitude, which is a function of overall contrast and image brightness, becomes problematic. To use such methods, the parameters for the gradient magnitude image intensity analysis need to be continually adjusted based on the instantaneous solids concentration. This, of course, is extremely difficult. It should be appreciated that any other image, beyond the in-situ images discussed above, where the brightness, the contrast, the lighting conditions, the focus, and/or any other parameter that affects the quality of the image, can vary in unknown and/or uncontrolled ways, can also be analyzed using systems and methods according to this invention.

In contrast, the image intensity gradient direction rarely changes significantly, regardless of any variation in the image intensity and in the overall image contrast. That is, the image intensity gradient direction is typically insensitive to changes in contrast and/or to changes in brightness. Thus, the image intensity gradient direction technique is particularly useful when analyzing low quality, noisy, poorly lit images, images taken when the lighting conditions are unknown or uncontrolled, or the like. However, it should be appreciated that image intensity gradient magnitude techniques can be used even if the image intensity and the image contrast of the captured images are appropriately adjusted or otherwise compensated for.

Figure 5:
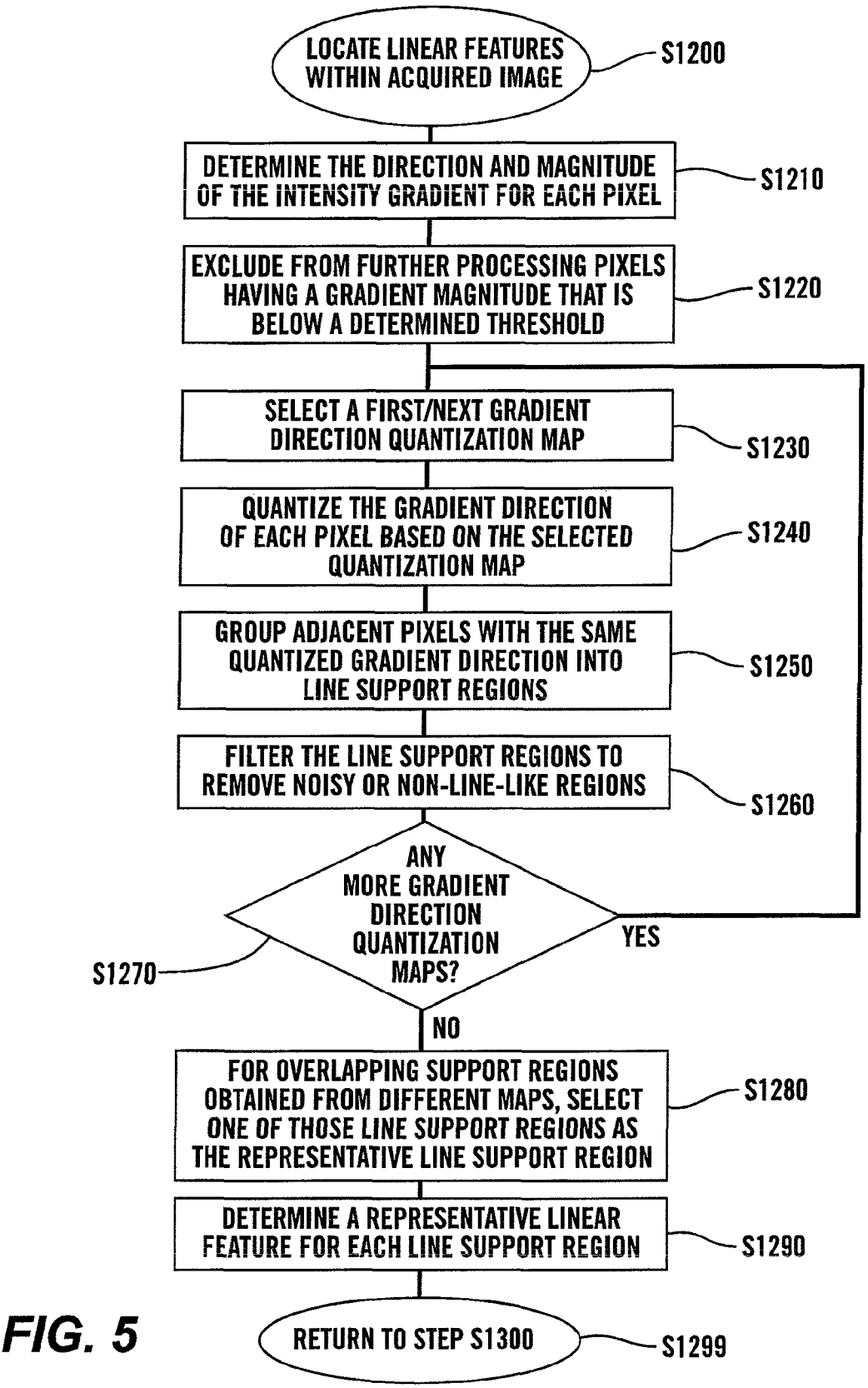
FIG. 5 is a flowchart outlining one exemplary embodiment of a method for locating linear features within an image according to this invention.
Figure 19:
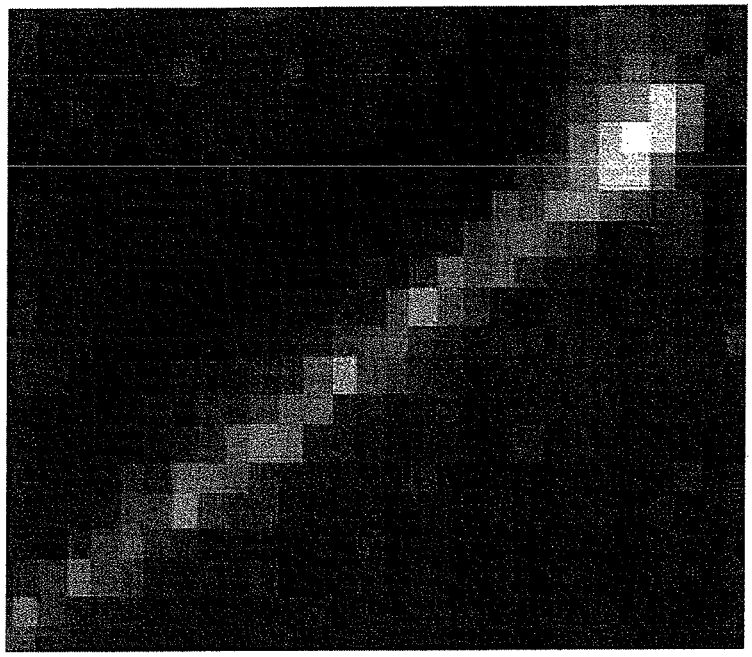
FIG. 19 illustrates one exemplary image containing an object edge to be segmented according to this invention.

FIG. 5 outlines one exemplary embodiment of a method according to this invention for locating linear features within the acquired image. As shown in FIG. 5, beginning in step S1200, operation continues to step S1210, where the direction and magnitude of the intensity gradient is determined for each pixel. This can be most easily seen in FIGS. 19 and 20. FIG. 19 shows an enlarged portion of an acquired image, where the individual pixels can be seen. The image gradient is a function of the image values, where low image values correspond to dark areas and high image values correspond to light areas. The gradient direction typically points from the low image value pixels towards the high image value pixels.

Figure 20:
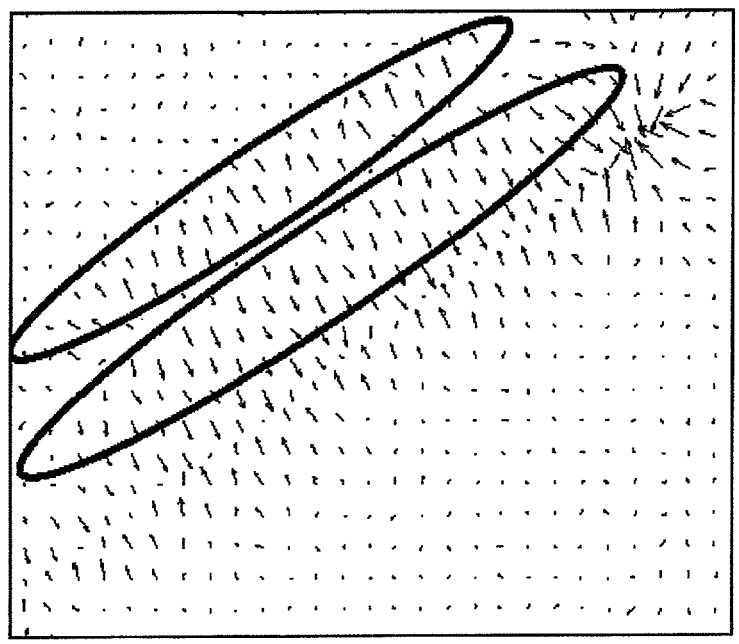
FIG. 20 is a graph illustrating gradient directions obtained by analyzing the image shown in FIG. 19.

For the image portion shown in FIG. 19, the direction of the image gradient is determined according to the technique disclosed in the incorporated Burns reference, resulting in the gradient vector field shown in FIG. 20. In the portion of image data shown in FIG. 19, a streak of relatively darker pixels extends from around the mid-point of the left side of the image to about the mid-point of the top side of the image. Parallel to that relatively darker streak, a relatively lighter streak extends from the lower left hand corner to the upper right hand corner of the image. The gradient direction typically extends from a relatively darker pixel to a relatively lighter pixel. Because, as outlined above, pixel values typically decrease to indicate darker image regions, the gradient direction typically extends from pixels having relatively low image values to pixels having relatively high image values.

As shown in FIG. 20, in the upper left hand and lower right hand corners, because the pixels all have similar image values the gradient direction is typically nonexistent or randomly oriented relative to the adjacent pixels. However, in the diagonal region extending from the upper right to the lower left portions of the image, there are two regions where the image gradient points in roughly the same direction over sets of pixels that are at least touching on their vertices. Because, as outlined above, the gradient direction typically extends from relatively higher valued pixels to relatively lower valued pixels, the two circled regions in FIG. 20 correspond to the image gradient directions extending from the relatively darker streak shown in FIG. 19.

Next, in step S1220, pixels having a gradient magnitude that is below a determined threshold are excluded from further processing. Referring to FIG. 20, the regions in the upper left hand corner and the lower right hand corner, while having gradient directions, have very small changes in image value. Thus, these regions have relatively small gradient magnitudes and thus are excluded from further processing.

Then, in step S1230, a first or next gradient direction quantization map is selected. Operation then continues to step S1240. It should be appreciated that the gradient direction, which can take any value between 0° and 360°, can be divided into any number of quantization sets, and that the 0° point of the circle can be set at any location. It should further be appreciated that, because the gradient direction divisions and the orientation of the 0° direction are somewhat arbitrary, it is possible to divide the pixels associated with a single edge in the image between two quantization groups based on small variations in the gradient direction. Multiple gradient direction maps can be used to avoid this problem.

In various exemplary embodiments of systems and methods according to this invention, the 360° gradient circle is divided into six 60° quantization sectors. To create two different quantization maps, two different 0° starting points, offset by 30°, are selected. However, it should be appreciated that any number of different quantization maps, with different 0° starting positions, different numbers of divisions, or bins, extending over different angular ranges and/or the like can be used to create any set of desired quantization maps.

In step S1240, the gradient direction of each pixel is quantized based on the selected quantization map. Then, in step S1250, adjacent pixels with the same quantized gradient direction, i.e., pixels grouped into the same 60° division or bin, are grouped into one or more line support regions. Next, in step S1260, the line support regions are filtered to remove noisy and/or non-line-like regions. Operation then continues to step S1270.

It should be appreciated that, in step S1250, the adjacent pixels are grouped based on connected component analysis. In various exemplary embodiments of systems and methods according to this invention, 8-way connectivity is allowed, such that pixels touching only at a single vertex point having the same quantized gradient are nevertheless grouped into the same line support region. It should be appreciated that the connected component analysis can be limited to 4-way connectivity, such that only pixels that share an edge are grouped together into line support regions. However, this is likely to lead to line support regions that are inappropriately small. It should also be appreciated that step S1260 is optional. Thus, step S1260 could be skipped and the noisy or non-line-like regions left in the set of line support regions developed in step S1250. In this case, operation would continue directly from step S1250 to step S1270.

In step S1270, a determination is made whether there are any more gradient direction quantization maps that need to be applied to the determined gradient directions for the image pixels. If so, operation returns to step S1230, where a next gradient direction quantization map is selected. Otherwise, if all of the gradient direction quantization maps have been applied, operation continues to step S1280. In step S1280, for any line support regions, which were generated based on one gradient direction quantization map, that overlap one or more other line support regions that were generated from other gradient direction quantization maps, one line support region of each such set of overlapping line support regions is selected as the representative line support region for that set of overlapping line support regions. It should be appreciated that, in various exemplary embodiments, this selection is done according to the technique outlined in the incorporated Burns reference. It should further be appreciated, that if only a single quantization direction gradient map is implemented, steps S1270 and S1280 can be omitted. In this case, operation would continue directly from step S1250 or step S1260 (as outlined above) to step S1290.

In step S1290, a representative linear feature is determined for each line support region. In various exemplary embodiments, this is done by blob analysis, where, for each line support region, an ellipse, having the same geometric moments as that line support region, is determined. In various exemplary embodiments, for each line support region, the properties of the best-fit ellipse for that line support region are used as the properties of that line support region. That is, the major axis of the best-fit ellipse is used as the representative line, where its length is the length of the major axis, its orientation is the orientation of the major axis, its centroid is the center of the major axis, and the length of the minor axis of the ellipse is the width of the representative line.

Figure 21:
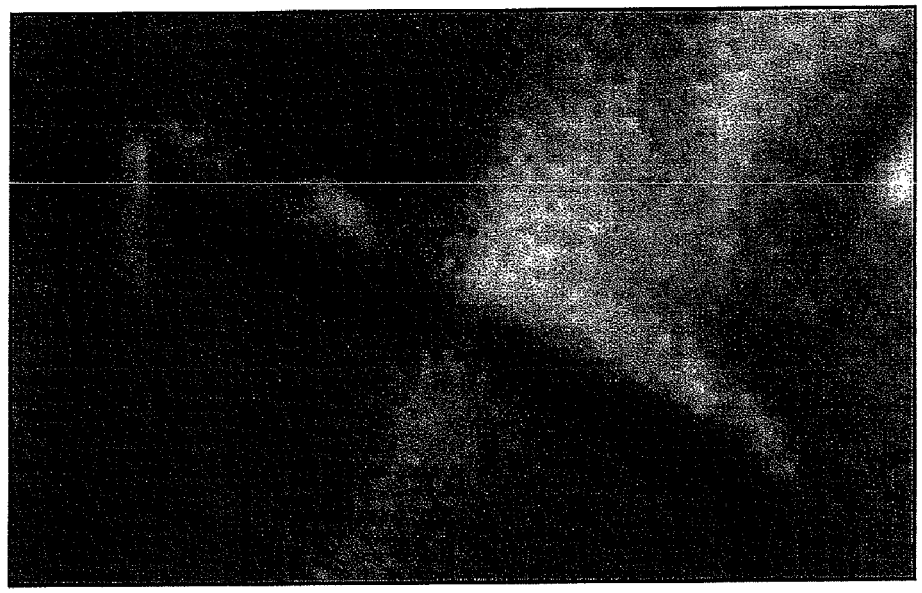
FIG. 21 shows an enlarged portion of the image shown in FIG. 2.
Figure 22:
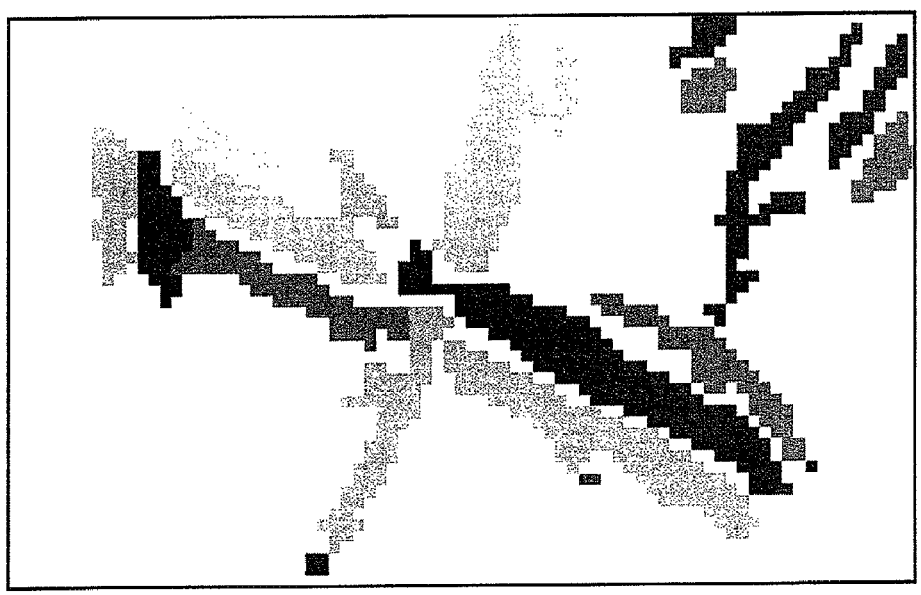
FIG. 22 illustrates one exemplary embodiment of a set of connected components generated from the image shown in FIG. 21 obtained by applying steps S1210-S1250 to that image.

This process is shown in FIGS. 21-24. In particular, FIG. 21 shows, in greater detail, the portion 110 of the acquired image 100 shown in FIG. 2. FIG. 22 shows 15 line support regions identified by applying steps S1210-S1280 to the image shown in FIG. 21.

Figure 23:
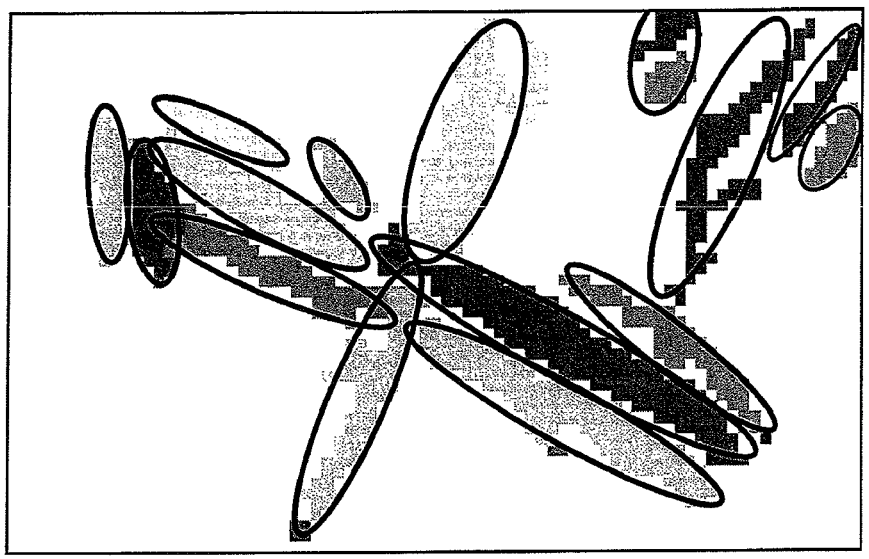
FIG. 23 illustrates one exemplary embodiment of mathematical representations for the connected components shown in FIG. 22.
Figure 24:
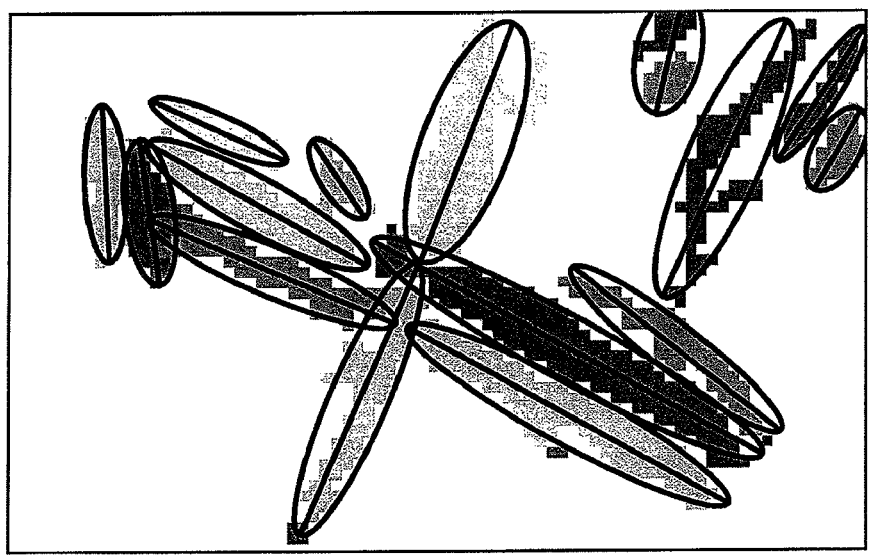
FIG. 24 illustrates one exemplary embodiment of linear features extracted from the mathematical representations shown in FIG. 23.
Figure 25:
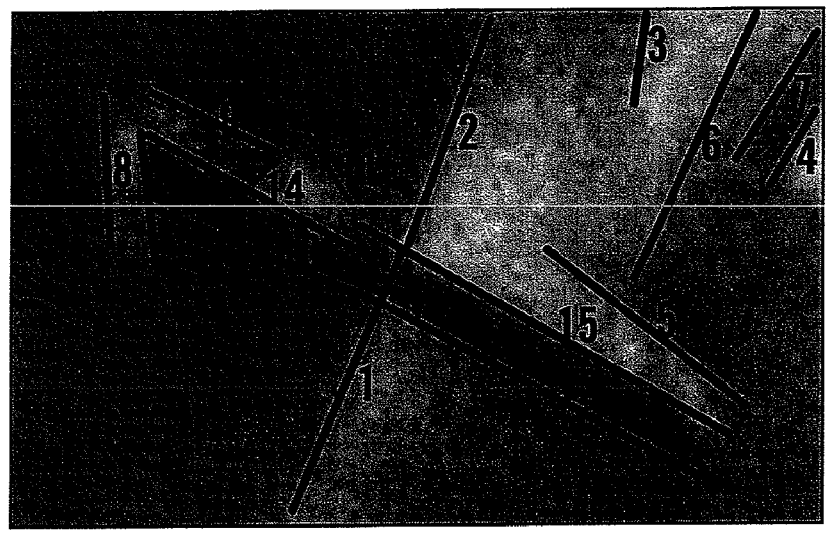
FIG. 25 shows the image shown in FIG. 21 with the linear features shown in FIG. 24 superimposed on it.

FIG. 23 shows the best fit ellipses determined for each of the 15 line support regions shown in FIG. 22. FIG. 24 shows the best fit ellipses and their major axes superimposed on the line support regions shown in FIG. 22. FIGS. 23 and 24 thus illustrate one exemplary embodiment of determining the representative linear feature for each line support region of step S1290. FIG. 25 shows the linear features determined in step S1290 superimposed over the original image data shown in FIG. 21, with each of the representative linear features labeled 1-15 for the 15 identified line support regions shown in FIG. 22.

Figure 6:
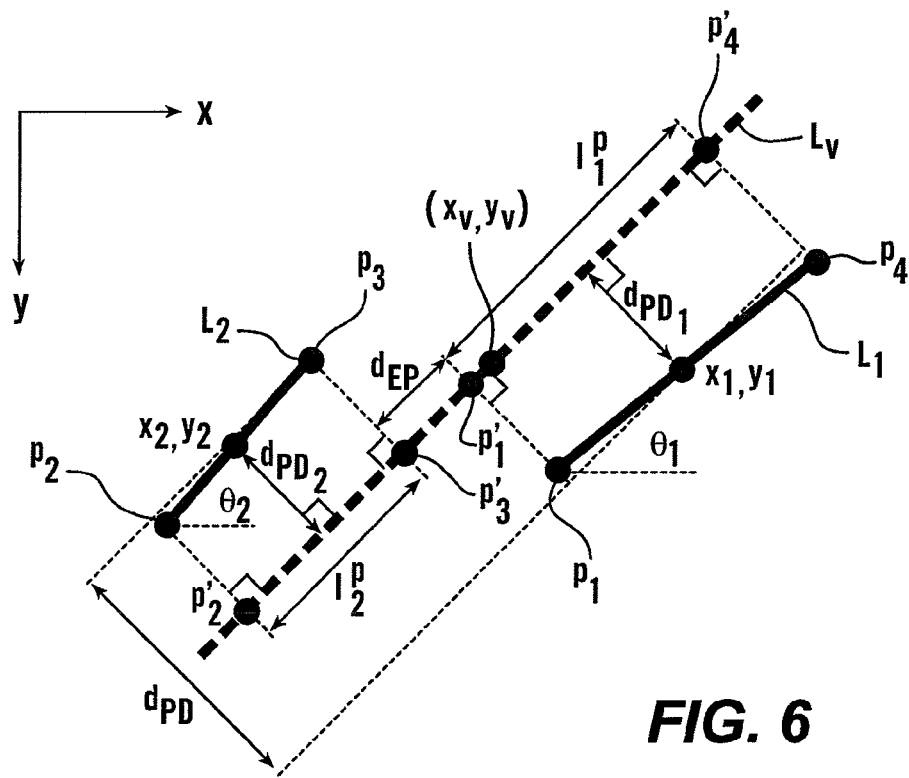
FIG. 6 illustrates one exemplary embodiment of how various line parameters are defined.

FIG. 6 shows a pair of linear features $L_1$ and $L_2$ that are representative of a pair of line-like regions that have been extracted from a sample image. Each of the linear features $L_1$ and $L_2$ have an orientation $\theta_1$ and $\theta_2$, respectively, that defines the angle that the linear features $L_1$ and $L_2$ make with respect to some reference line in the image. Because these images are typically digital images comprising a 2-dimensional array of pixels, the reference line is typically either horizontal or vertical. However, it should be appreciated that the reference line can be at any angle, as the important aspect is not the absolute orientation of each of the lines with respect to the reference line, but rather the relative orientation of the lines to each other. Thus, the important feature is the angular difference $\Delta\theta$, which is defined as the absolute difference between the two orientations $\theta_1$ and $\theta_2$, or:

$$\Delta\theta = |\theta_1 - \theta_2|. \quad (1)$$

As a result, the absolute orientation of each linear feature $L_1$ and $L_2$ to the reference line drops out of the equation and is thus irrelevant.

In addition to the relative orientation between the two linear features, the line lengths $l_1$ and $l_2$ and the spatial positions of the linear features $L_1$ and $L_2$ relative to each other are also useful information. Thus, the perpendicular distance $d_{PD}$, between the linear features $L_1$ and $L_2$ defines their lateral spatial offset. If the perpendicular distance $d_{PD}$ is 0, the lines are co-linear. Since it is highly unlikely many lines will be truly co-linear, a threshold value $\epsilon_{PD}$ is typically designated such that, when the perpendicular distance $d_{PD}$ is less than the threshold $\epsilon_{PD}$, the lines $L_1$ and $L_2$ are considered to be co-linear. It should be appreciated that the perpendicular distance $d_{PD}$ can be determined in a variety of ways. For example, the perpendicular distance $d_{PD}$ can be determined by extending one line to a point that is perpendicular to one end point of the other line and taking the perpendicular distance at that point. Moreover, this can be done for both linear features and the two perpendicular distances can then be combined and averaged to find an average perpendicular distance. It should be appreciated that any other appropriate method for determining the perpendicular distance $d_{PD}$ can be used. Likewise, an end point distance $d_{EP}$ is determined to indicate how far apart the nearest end points of the two linear features $L_1$ and $L_2$ are. Because there is always some uncertainty in determining the end points of the linear features, $L_1$ and $L_2$, the linear features $L_1$ and $L_2$ can be considered to be overlapping if the end point distance $d_{EP}$ is negative, or 0, or even positive if the end point distance $d_{EP}$ is within an end point threshold $\epsilon_{PD}$.

As indicated above, once the various linear features are extracted from the acquired image, the spatial relationships between sets of two or more of the linear features are examined to: 1) determine if the linear features are co-linear, and thus represent portions of the same edge feature of the object depicted in the acquired image, or 2) have an appropriate spatial relationship such that the linear features represent two different yet related edges on the same object. In various exemplary embodiments according to this invention, these appropriate spatial relationships can include angular offset between the lines, orientation offset along the direction the lines extend in, and/or offset perpendicular to the linear features.

As shown in FIG. 6, for any pair of two linear features $L_1$ and $L_2$, each linear feature $L_1$ and $L_2$, respectively, will have an orientation $\theta_1$ and $\theta_2$ relative to some reference line in the image. Each of the linear features $L_1$ and $L_2$ will also have respective mid-points $(x_1, y_1)$ and $(x_2, y_2)$. As outlined above, there are various ways to determine these spatial parameters.

FIG. 6 illustrates one exemplary embodiment of a technique for determining these parameters according to this invention. In particular, as shown in FIG. 6, a virtual line $L_v$ is defined between the two linear features $L_1$ and $L_2$. In particular, the virtual line $L_v$ is defined by determining the length-weighted averages of the positions and orientations of the linear features $L_1$ and $L_2$. Thus, the orientation $\theta_v$ and the mid-point or centroid $(x_v, y_v)$ of the virtual line $L_v$ are defined as:

$$x_v = \frac{(l_1 * x_1) + (l_2 * x_2)}{l_1 + l_2} \quad (2)$$

$$y_v = \frac{(l_1 * y_1) + (l_2 * y_2)}{l_1 + l_2} \quad (3)$$

$$\theta_v = \frac{(l_1 * \theta_1) + (l_2 * \theta_2)}{l_1 + l_2} \quad (4)$$

where:

$l_1$ and $l_2$ are the lengths of the linear features $L_1$ and $L_2$;

$\theta_1$ and $\theta_2$ are the orientations of the linear features $L_1$ and $L_2$;

$x_1$ and $x_2$ are the x-axis positions of the midpoints or centroids of the linear features $L_1$ and $L_2$; and $y_1$ and $y_2$ are the y-axis coordinates of the mid-points of the linear features $L_1$ and $L_2$.

As shown in FIG. 6, the two linear features $L_1$ and $L_2$ have, respectively, end points $p_1$ and $p_4$, and $p_2$ and $p_3$. Each of these end points is perpendicularly projected onto the virtual line $L_v$ as the points $p'_1$-$p'_4$. The length $l_v$ of the virtual line 1, is defined as the shortest line that includes all of the projected end points $p''_1$-$p_4$, i.e., in the example shown in FIG. 6, the line extending from $p'_2$ to $p'_4$.

Figure 7:
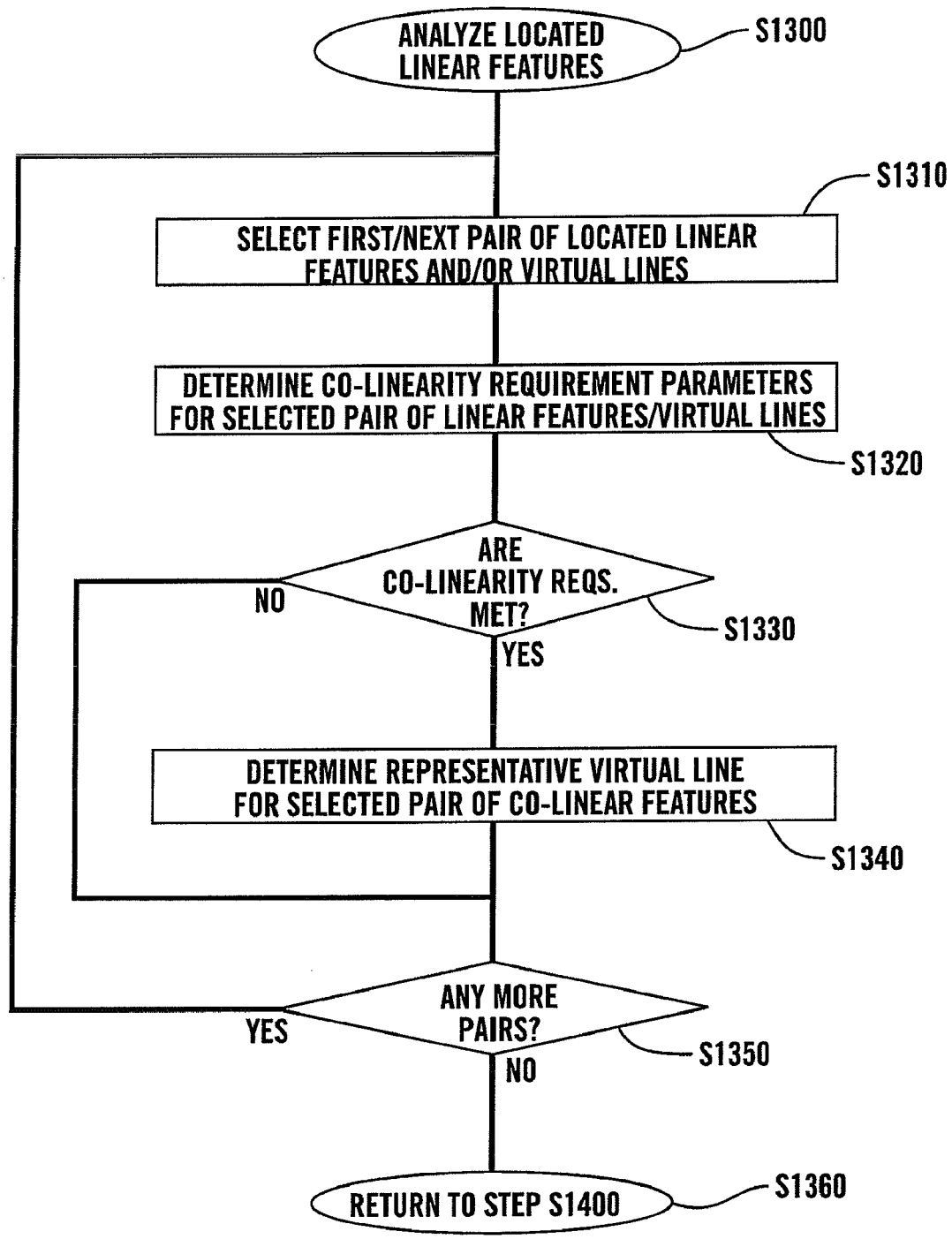
FIG. 7 is a flowchart outlining a first exemplary embodiment of a method for analyzing the located linear features according to this invention.

FIG. 7 is a flowchart outlining a first exemplary embodiment of a method for analyzing the located linear features according to this invention. As shown in FIG. 7, beginning in step S1300, operation continues to step S1310, where a first or next pair of located linear features and/or virtual lines, which will be described below with respect to step S1340, are selected. Then, in step S1320, one or more co-linearity parameters are determined for the selected pair of linear features and/or virtual lines. Next, in step S1330, a determination is made whether the determined co-linearity requirements are met by the determined co-linearity parameters for selected pair of linear features and/or virtual lines. If so, operation continues to step S1340. Otherwise, operation jumps directly to step S1350.

In step S1340, a representative virtual line is determined for the selected pair of co-linear linear features and/or virtual lines, as outlined above with respect to FIG. 6. Operation then continues to step S1350, where a determination is made whether there are any more pairs that need to be selected. If so, operation jumps back to step S1310. Otherwise, operation continues to step S1360, where operation of the method returns to step S1400.

It should be appreciated that, in various exemplary embodiments of systems and methods according to this invention, only pairs of linear features are selected and analyzed in steps S1310-1350. Thus, in such exemplary embodiments, each virtual line represents exactly two lines that are determined to be co-linear. While this is usually sufficient, it may be desirable to generate virtual lines that represent the combination of three or more lines that meet the co-linearity requirements. This may be desirable when analyzing extremely noisy or poorly lit images, images anticipated to have many overlapping objects, or images having extremely long objects, where it may be difficult to generate at most two lines that represent the full extent of the length of the object.

Accordingly, in various other exemplary embodiments, after a virtual line is created in step S1340, that first virtual line is added back into the list of linear features and is used as one element with each of the other linear features to determine if any of the other linear features, when paired with that first virtual line, also meet the co-linearity requirements. If so, in various exemplary embodiments, a second virtual line is created that represents the combination of the first virtual line with the selected linear feature. That first virtual line may be maintained or may be discarded. In various other exemplary embodiments, a second virtual line is created that represents the virtual line generated directly from all three (or more) linear features. Again, the first virtual line may be maintained or may be discarded.

In various other exemplary embodiments, after all of the pairs of linear features have been selected and all of the virtual lines for those linear features have been generated, the virtual lines are examined to determine if any pair of virtual lines contains the same linear features. If so, a new virtual line is created, as outlined above with respect to FIG. 6, using the two virtual lines instead of two linear features. This process can, of course, then be repeated to determine if the new virtual line shares a constituent linear feature with any other virtual lines. If so, the process can be repeated. It should be appreciated, that in such exemplary embodiments, the original virtual lines can either be maintained or discarded as desired.

Figure 26:
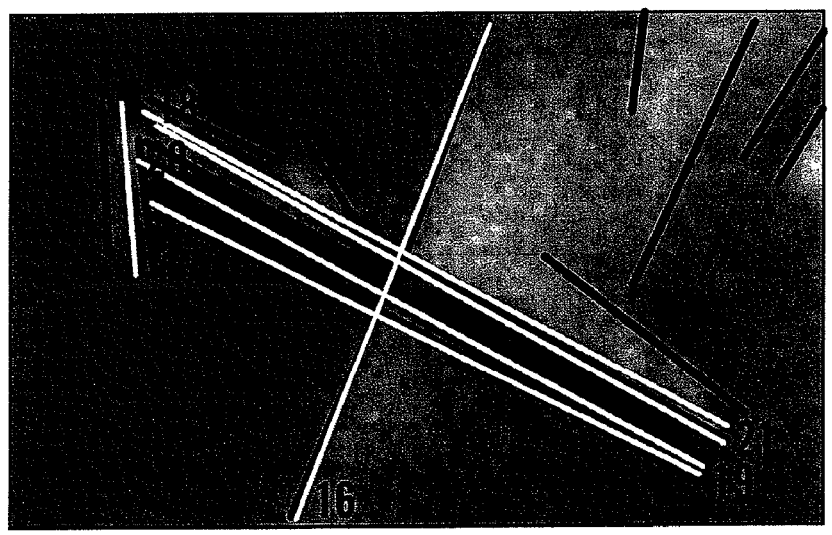
FIG. 26 illustrates the virtual lines generated after analyzing the linear features shown in FIG. 25 based on the co-linearity requirements.

FIG. 26 illustrates the virtual lines determined from the linear features shown in FIG. 25. In particular, the virtual lines shown in FIG. 26 were determined by using only linear features to determine the virtual lines. That is, no pairs of virtual lines with either linear features or other virtual lines were used to determine the virtual lines shown in FIG. 26. As shown in FIG. 26, six pairs of the linear features shown in FIG. 25 meet the co-linearity requirements, resulting in the six virtual lines 16-21 shown in FIG. 26. In particular, virtual line 16 corresponds to linear features 1 and 2, virtual line 17 corresponds to linear features 8 and 13, virtual line 18 corresponds to linear features 9 and 15, virtual line 19 corresponds to linear features 10 and 12, virtual line 20 corresponds to linear features 12 and 14, and virtual line 21 corresponds to linear features 14 and 15.

Figure 8:
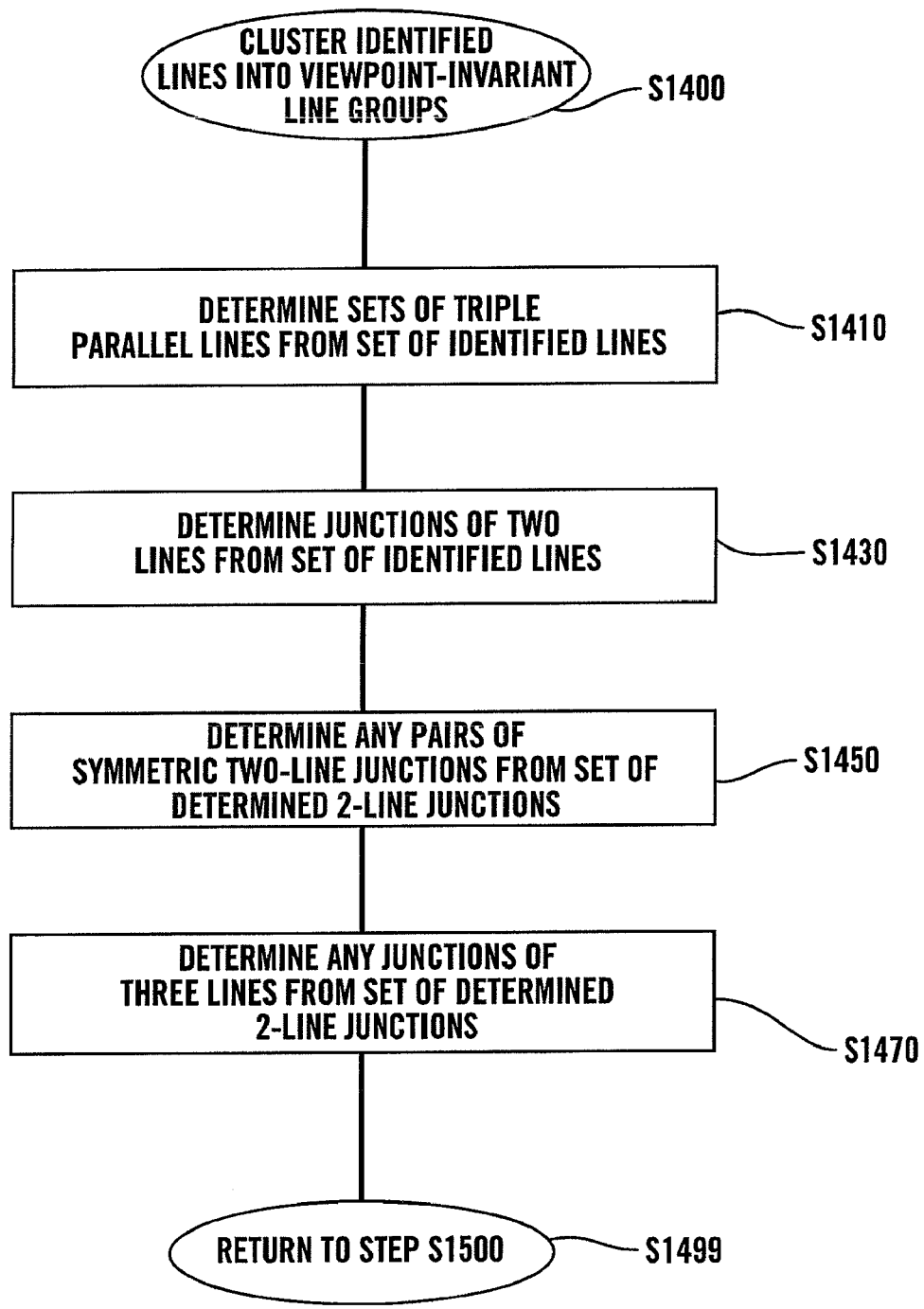
FIG. 8 is a flowchart outlining a first exemplary embodiment of a method for determining at least one viewpoint-invariant line group.

FIG. 8 is a flowchart outlining a first exemplary embodiment of a method for determining one or more viewpoint-invariant line groups from the located and analyzed linear features according to this invention. As outlined above, in step S1400, various ones of the located lines, i.e., groups of the identified linear features and/or the generated virtual lines, are grouped or clustered together into viewpoint-invariant line groups. These viewpoint-invariant line groups represent spatial relationships between edges in the wireframe models that are expected to appear in the obtained image when it contains instances of the one or more objects to be located in the image.

As shown in FIG. 8, beginning in step S1400, operation continues to step S1410, where sets of triple parallel lines are determined from the identified linear features and/or the generated virtual lines. Then, in step S1430, one or more junctions of two lines are determined from the identified linear features and/or the generated virtual lines. Next, in step S1450, any pairs of symmetric two-line junctions occurring within the set of determined 2-line junctions are determined or identified. Then, in step S1470, any junctions of three lines occurring within the set of determined 2-line junctions are determined or identified. Operation then continues to step S1499, which returns operation of the method to step S1500.

It should be appreciated that the viewpoint-invariant line groups represent spatial relationships that do not change regardless of the angle that the object is viewed at. Typically, such viewpoint-invariant line groups are defined by the number of lines in the group, the connections between the lines, the relative lengths of the lines and/or the relative angles between two intersecting lines. Various common ones of the viewpoint-invariant line groups are shown in, and described relative to, FIGS. 28-32. Once the located lines are grouped or clustered together into one or more viewpoint-invariant line groups, each viewpoint-invariant line group can be analyzed to determine which object most likely gave rise to that viewpoint-invariant line group and the size, orientation and other parameters of that instance of that object.

Figure 9:
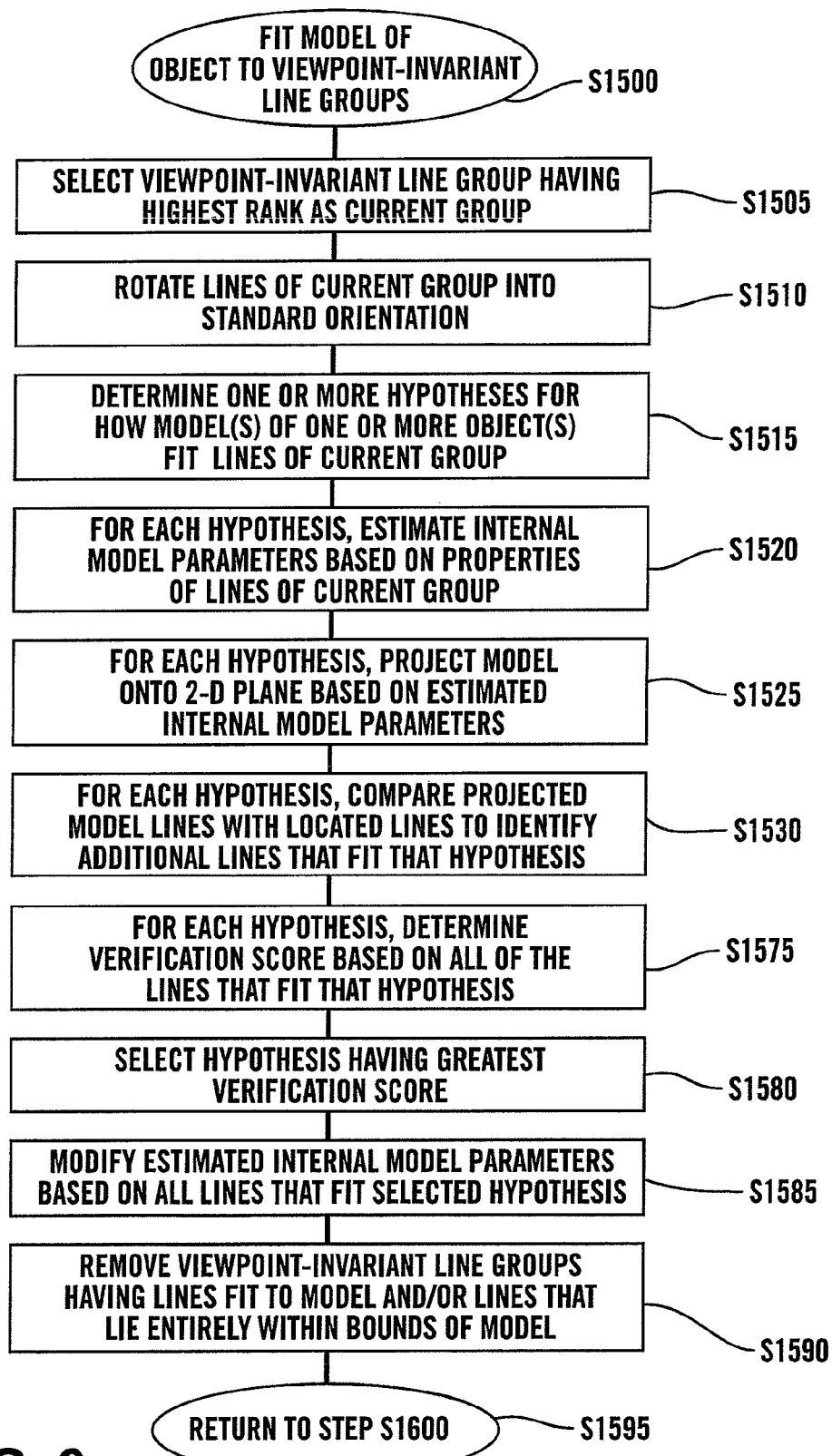
FIG. 9 is a flowchart outlining a first exemplary embodiment of a method for fitting the model of the object(s) to be located to the determined viewpoint-invariant line group.

FIG. 9 is a flowchart outlining a first exemplary embodiment of a method for fitting a model of an object to be identified to one or more of the identified viewpoint-invariant line groups determined in step S1400. Beginning in step S1500, operation of the method continues to step S1505, where a viewpoint-invariant line group that has a highest rank is selected as a current group. Then, in step S1510, the lines of the current viewpoint-invariant line group are rotated into a standard orientation that allows possible correlations to be made between the lines of the current group to be fit to the lines constituting the one or more models for the one or more objects to be located in the obtained image. Next, in step S1515, one or more hypotheses are determined, where each hypothesis describes how one of the one or more models for one of the one or more objects to be located fits the lines of the current group. Operation then continues to step S1520.

In step S1520, for each hypothesis, internal model parameters for the fitted model are estimated based on properties of the lines of the current group. Next, in step S1525, for each hypothesis, based on the estimated internal model parameters, the model for the object to be located is projected on to a two-dimensional plane. Then, in step S1530, for each hypothesis, the edges of the projected model are compared with located lines, i.e., various linear features and/or virtual lines, that have been identified in the obtained image and that are generally near to the lines of the current group to identify any additional ones of those lines that correspond to other edges of the fitted and projected model of a particular hypothesis. Operation then continues to step S1575.

In step S1575, for each hypothesis, a verification score is determined based on all of the lines that have been identified as corresponding to edges in the fitted and projected model based on how the model is fit to the current group for that hypothesis. Then, in step S1580, the hypothesis, describing how the object model fits to the current group, having the greatest verification score is selected. Next, in step S1585, for the selected hypothesis, the estimated internal model parameters and viewpoint parameters, such as orientation, length, width, height and the like are modified from a best fit to only the lines of the current group to a best fit of all of the lines that are identified as corresponding to or associated with edges in the projected model of the selected hypothesis. Operation then continues to step S1590.

In step S1590, any viewpoint-invariant line groups that have one or more lines, that have either been associated with edges of the projected model of the selected hypothesis or that have lines that lie entirely within the bounds of the best-fit model, are discarded, such as by being removed from a list of identified viewpoint-invariant line groups. It should be appreciated that steps S1505-S1590 are then repeated until all of the identified viewpoint-invariant line groups are either matched to one of the one or more models for one of the one or more objects or are discarded. Operation then continues to step S1595, which returns operation of the method to step S1600.

Figure 10:
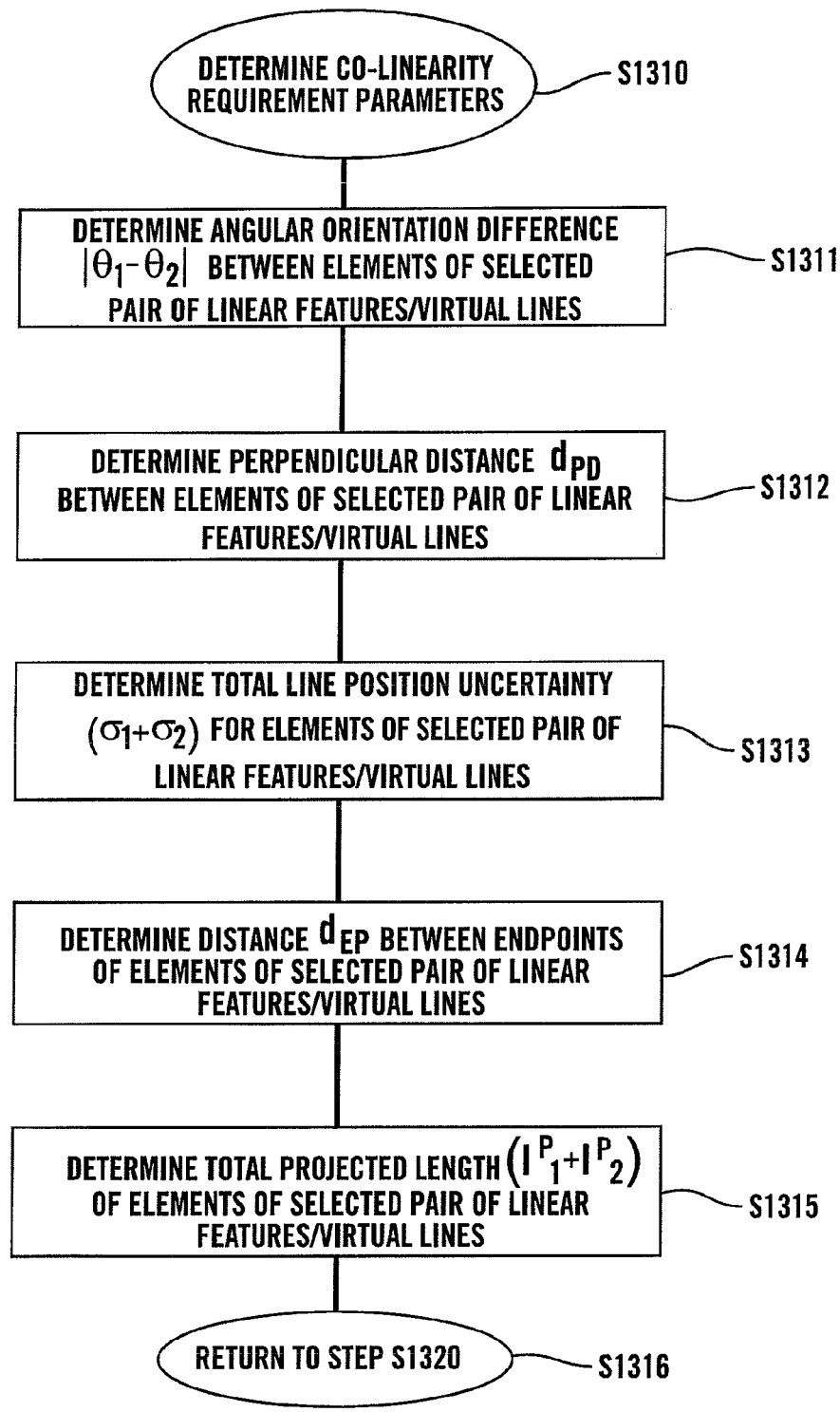
FIG. 10 is a flowchart outlining one exemplary embodiment of a method for determining co-linearity requirements parameters for sets of linear features.

FIG. 10 is a flowchart outlining one exemplary embodiment of the method for determining the co-linearity parameters of step S1310. As shown in FIG. 10, beginning in step S1310, operation continues to step S1311, where the angular orientation difference between the linear features (and/or virtual lines, if analyzed as described above) of the selected pair of linear features (and/or virtual lines) is determined as:

$$\Delta\theta = |\theta_1 - \theta_2| \quad (5)$$

Then, in step S1312, the perpendicular distance $d_{PD}$ between the linear features (and/or virtual lines) of the selected pair of linear features (and/or virtual lines) is determined as shown in FIG. 6. Next, in step S1313, the total line position uncertainty $(\sigma_1 + \sigma_2)$ for the linear features (and/or virtual lines) of the selected pair of linear features (and/or virtual lines) is determined. The line position uncertainty values $\sigma_1$ and $\sigma_2$ for the two linear features (and/or virtual lines) 1 and 2 represents the uncertainty of the position of the elements 1 and 2, respectively, in the direction perpendicular to their length. In various exemplary embodiments, for linear features, the line position uncertainty $\sigma_1$ and $\sigma_2$ is assumed to be equal to one-half of the length of the minor axis of the best-fit ellipse for the corresponding linear feature. In various other exemplary embodiments, the line position uncertainty $\sigma_V$ for a virtual line $L_V$ is assumed to be one half of the length-weighted average of the uncertainties $\sigma_1$ and $\sigma_2$ of its constituent linear features $L_1$ and $L_2$. Operation then continues to step S1314.

In step S1314, the endpoint distance $d_{EP}$ between the endpoints of the linear features (and/or virtual lines) of the selected pair of linear features (and/or virtual lines) is determined as outlined above with respect to FIG. 6. Next, in step S1315, the total projected length $(l^P_1 + l^P_2)$ of the two linear features (and/or virtual lines) of the selected pair of linear features (and/or virtual lines) is determined as outlined above with respect to FIG. 6. Operation then continues to step S1316, which returns operation of the method to step S1320.

Figure 11:
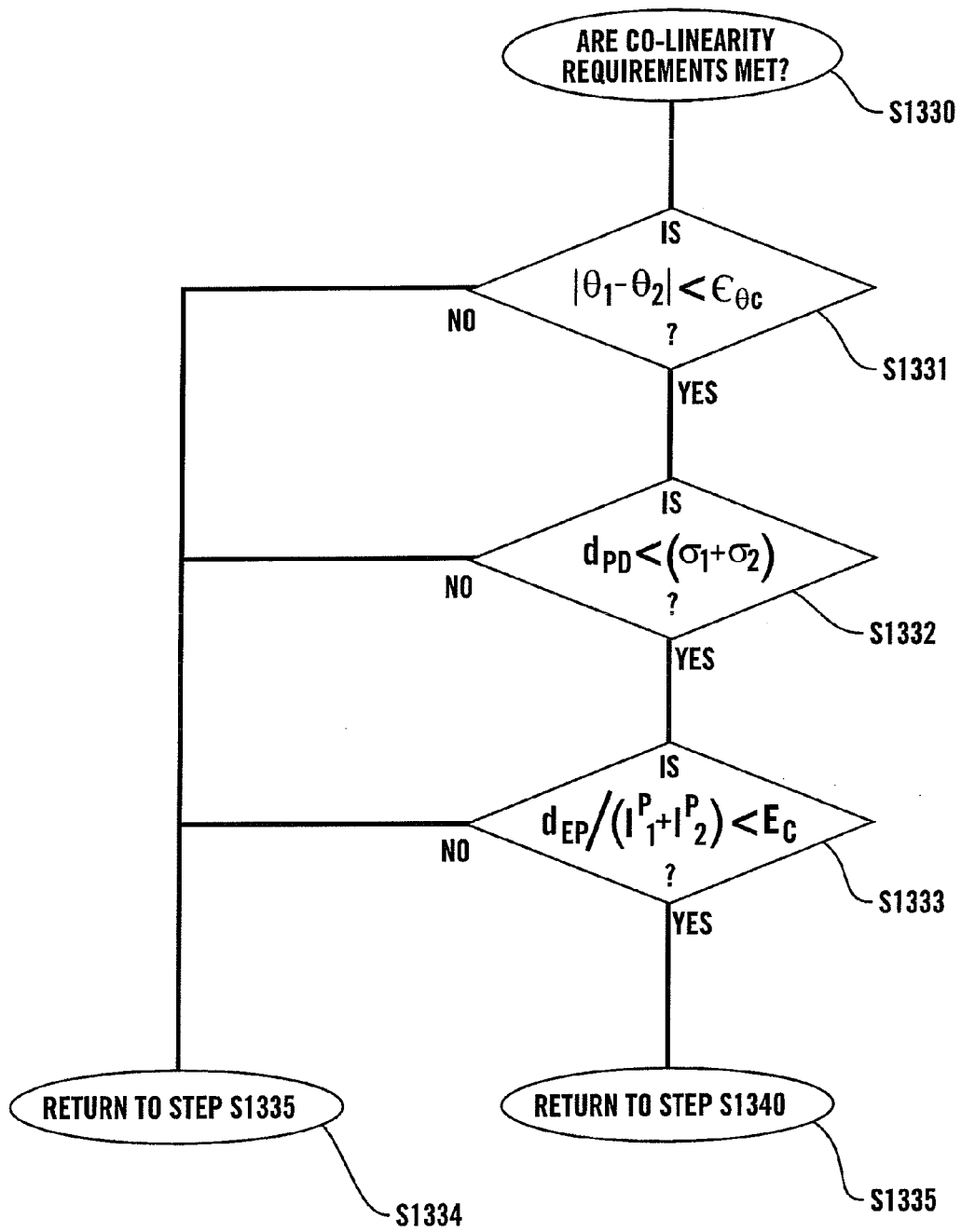
FIG. 11 is a flowchart outlining one exemplary embodiment of a method for determining if the co-linearity requirements are met.

FIG. 11 is a flowchart outlining one exemplary embodiment for the method for determining whether the co-linearity requirements of step S1330 are met. As shown in FIG. 11, operation of the method begins in step S1330 and continues to step S1331, where a determination is made whether the angular offset or difference $\Delta\theta$ meets the criterion:

$$\Delta\theta = |\theta_1 - \theta_2| < \epsilon_{\theta c}, \quad (6)$$

where $\epsilon_{\theta c}$ is a user specified threshold that provides a limit on how large the angle can be between the linear features (and/or virtual lines) before they can no longer be considered to be co-linear. If $\Delta\theta < \epsilon_{\theta c}$ operation continues to step S1332. Otherwise, operation jumps directly to step S1334.

In step S1332, a determination is made whether the perpendicular off-set distance $d_{PD}$ is less than the total line position uncertainty. That is, whether the perpendicular offset distance $d_{PD}$ meets the criterion:

$$d_{PD} < (\sigma_1 + \sigma_2) \quad (7)$$

If the perpendicular off-set distance $d_{PD}$, is less than the total line uncertainty $\sigma_1$ and $\sigma_2$, operation continues to step S1333. Otherwise, operation again jumps directly to step S1334.

In step S1333, a determination is made whether the ratio of the endpoint distance over the projected lengths of the two linear features and/or virtual lines is less than a user specific endpoint off-set threshold $E_C$. That is, whether the endpoint offset distance $d_{EP}$ meets the criterion:

$$d_{EP}/(l^P_1 + l^P_2) < E_C. \quad (8)$$

This criterion will always be met if the end point distance is negative, i.e., if the linear features (and/or vertical lines) are overlapping. If so, operation jumps to step S1335. Otherwise, operation continues to step S1334. In step S1334, at least one of the co-linear requirements was not met. Accordingly, operation of the method returns to step S1335. In contrast, in step S1335, all of the co-linearity requirements were met. Accordingly, operation of the method returns to step S1340.

It should be appreciated that, while the steps outlined in FIGS. 10 and 11 are shown distinct from each other for ease of understanding and explanation, in a typical implementation of the steps outlined in FIGS. 10 and 11, such as in a programmed microcomputer, microprocessor or the like, steps S1311-S1315 and steps S1331-S1333 would typically be interleaved. For example, step S1331 would be interleaved between steps S1311 and 1312. Similarly, step S1332 would be interleaved between steps S1313 and 1314, while step S1333 would be interleaved between steps S1315 and 1316. In this way, after each set of information sufficient for the next test is determined, it is immediately tested to determine if that co-linearity requirement is met. If not, there is no need to determine the other sets of information and operation can immediately jump to step S1334. In this way, if a pair of linear features and/or virtual lines fails to meet a previous co-linearity requirement, it is not necessary to determine the subsequent co-linearity parameters or perform the further analysis for the subsequent co-linearity requirements.

As outlined above with respect to FIG. 9, the model-based object location or identification systems and methods according to this invention match sets of primitive features extracted from an image which can include points, corners, lines or the like to a predefined model for each such object. While the particular exemplary embodiments discussed in this application use lines as the primitive image features, it should be appreciated that the systems and methods according to this invention are not limited to using lines. Likewise, as discussed herein, in various exemplary embodiments, the object models are parameterized wireframe models. However, it should be appreciated that the object models that can be used with systems and methods according to this invention are not limited to parameterized and/or wireframe models.

A wireframe model of an object comprises a set of q vertices $V = \{X_K[p_m]\}_{K=1 \ldots q}$ and a set of r lines or edges $E = \{E_J\}_{J=1 \ldots r}$. $X_x$ is a three-dimensional vector defined in a model-centered coordinate system and is a function of a set of model internal parameters $p_m$. An edge $E_J$ is a set of two labels pointing to the vertices in the set V that are connected by a particular edge J.

Figure 27:
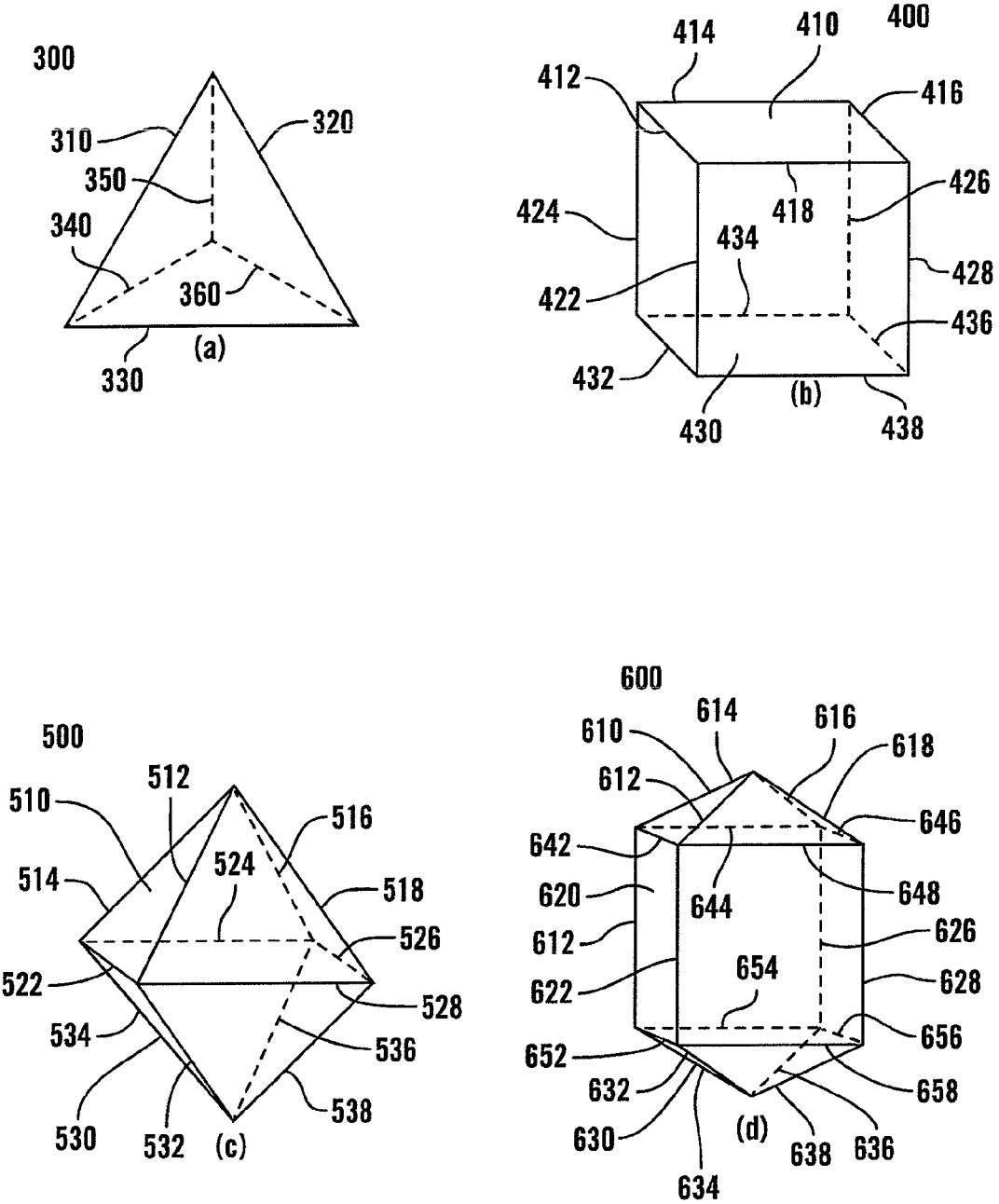
FIG. 27 shows a number of common object shapes of objects that can be identified or located in an image according to this invention.

FIG. 27 shows four exemplary wireframe models of various objects that one may wish to locate or identify in an obtained image. While it should be appreciated that these models are not exhaustive of all possible models for objects that one may wish to locate or identify in an obtained image, these wireframe models and the objects they represent illustrate a number of the most typical viewpoint-invariant line groups (VIG) that will typically occur in the obtained image. In particular, in portion (a) of FIG. 27, a wireframe 300 represents a tetrahedron i.e., a four-sided polyhedron having triangular faces. As shown in FIG. 27, the wire model 300 of the tetrahedron comprises three visible edges 310, 320 and 330 shown in solid lines and three hidden edges 340, 350 and 360, shown in dashed lines. This representational scheme will be repeated throughout this application. The portion (b) of FIG. 27 shows a wireframe 400 of a cubic object. As shown in FIG. 27, the wireframe 400 has a top face 410 comprising edges 412, 414, 416 and 418 and a bottom face comprising edges 432, 434, 436 and 438. A plurality of edges 422, 424, 426 and 428 extend between the faces 410 and 430. As with the tetrahedron 300, the hidden lines 426, 434 and 436 of the cube 400 are shown in dashed lines.

Portion (c) of FIG. 27 shows an octahedron or bipyramid 500. As shown in FIG. 27, the octahedron 500 comprises a top pyramid 510, comprising edges 512, 514, 516 and 518, and a bottom pyramid 530, comprising edges 532, 534, 536 and 538, that are joined together at a square base, where this interface is represented by the edges 522, 524, 526 and 528. As in the tetrahedron and cube, the hidden lines 516, 524, 526 and 536 are shown in dashed form. Portion (d) of FIG. 27 shows the shape exhibited by crystals of glycine, an amino acid important in the pharmaceutical industry. As shown in FIG. 27, the glycine crystal comprises a central cube having a first pyramid extending from the top face of the cube and a second pyramid extending from the bottom face of the cube.

In particular, the glycine crystal 600 shown in FIG. 27 comprises a top pyramid 610 having edges 612, 614, 616 and 618, a central rectangular prism 620 having edges 622, 624, 626 and 628 and a bottom pyramid 630 having edges 632, 634, 636 and 638. The top pyramid 610 and the central rectangular prism 620 are joined at edges 642, 644, 646 and 648, while the bottom pyramid 630 and the central rectangular prism 620 are joined at edges 652, 654, 656 and 658. The wireframe model of the glycine crystal shown in FIG. 27 has three internal parameters $p_m=(h, w, t)$, 20 edges and 10 vertices. In this exemplary embodiment, h is the height of the central rectangular prism 620, w is the width of the rectangular prism 620, and t is the height of the pyramids 610 and 630. It should be appreciated that in general, each of the wireframe models shown in FIG. 27 have the same general kinds of internal parameters, although they will have a different number of edges and vertices.

As further outlined above in FIG. 9, to fit the wireframe model to the located lines, i.e., the linear features and/or virtual lines, that are identified in the obtained image, the wireframe model must be projected onto the image plane. This projection is determined by first applying rigid-body rotations and translations to change each model point X from the model-centered coordinate frame to a camera-centered coordinate frame of the image. That is:

$$X_c = R_z R_y R_x X + T \quad (9)$$

where:
$R_z$, $R_y$, and $R_x$ are rigid-body rotation matrices, which are functions of an in-plane orientation $\theta_z$;
the orientations of the wireframe that extend into the depth of the image are $\theta_y$ and $\theta_x$, respectively, and
$T=(t_x, t_y, t_z)$ is the translation vector.

Each model point is then projected onto the image point according to some imaging model. Under perspective projection, the transformation from a three-dimensional model point $X_c=(X_c, Y_c, Z_c)$ to an image point $x=(x,y)$ is given by:

$$x = \frac{f}{Z_c} X_c, \quad (10)$$

$$y = \frac{f}{Z_c} Y_c. \quad (11)$$

where f is the focal length of a camera.

Figure 37:
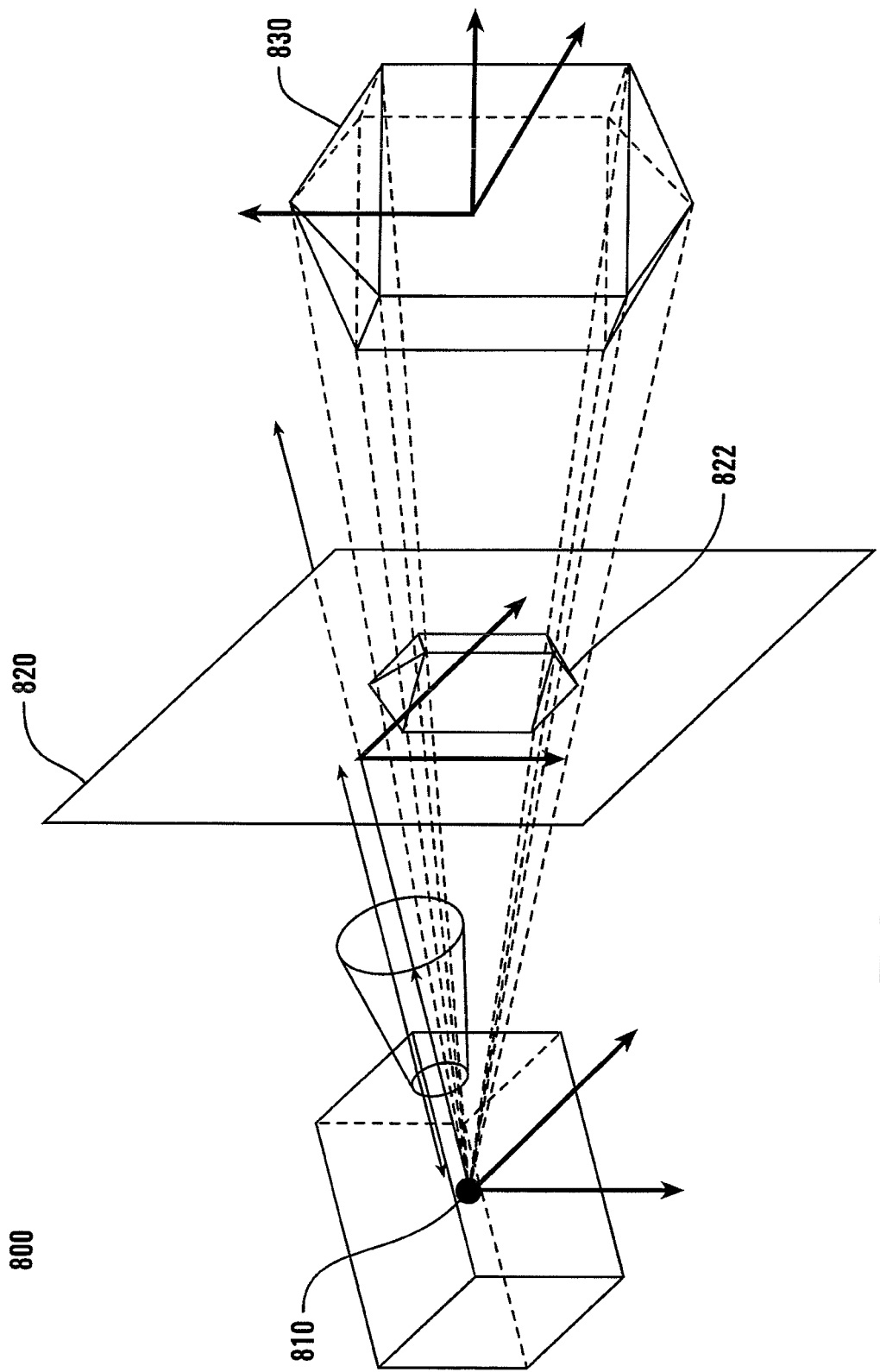
FIG. 37 illustrates how the model of the object shown in FIG. 37 is projected on to a two-dimensional plane.

FIG. 37 shows the prospective projection of a glycine wireframe model onto an image plane. It should be appreciated that, in various exemplary embodiments, the weak perspective imaging model is used. The weak perspective imaging model accurately approximates perspective projections so long as the depth of the objects being imaged is small relative to the distance of the objects from a camera. Under such imaging conditions, the fraction $f/Z_c$ and the in-plane translation parameter $T_z$ can be assumed to be constant for all objects. For images of objects such as crystals obtained using experimental set up shown in FIG. 3, this imaging model holds. It should be appreciated, that, in various exemplary embodiments, the fraction $f/Z_c=1$ and $T_z=0$ are appropriate values.

The projection of a model onto the image plane is completed by determining which of the edges of the wireframe model are visible for a given pose. Given a convex wireframe model, the visible model edges can be determined by the determining an outward normal vector, in the camera-centered coordinates, for each surface of the three-dimensional wireframe model. The sign of the dot project of this normal vector with the camera's optical axis determines whether or not this surface is visible. The visible model edges are then the edges of the visible surfaces.

Projecting the wireframe model onto the image plane results in a set of projected model edges:

$$E^P = \{(M_J, \hat{T}_J, L_J)\}_{J=1 \ldots m} \quad (12)$$

where:
$M_J$ is a vector pointing from the origin of the image coordinate system to the midpoint of the Jth model edge;
$\hat{T}_J$ is the unit tangent of the edge;
$L_J$ is the length of the edge; and
m is the number of visible model edges.

The set of data lines are defined similarly as:

$$S = \{(m_j, \hat{t}_j, l_j)\}_{j=1 \ldots n}, \quad (13)$$

where n is the number of lines, i.e., linear features or virtual lines, identified in the image.

As outlined above with respect to step S1400 of FIG. 4, the located linear features are perceptually clustered into viewpoint-invariant line groups based on an analysis of the located linear features. Perceptual clustering refers to organizing the primitive elements located in the image, such as points or lines, into higher-level, meaningful structures. These structures or groups are useful as visual cues for the location, size and/or orientation of a given object in the image. The viewpoint-invariant line groups are groups or clusters of lines that maintain certain properties regardless of the camera viewpoint. Such viewpoint-invariant line groups are desirable because the orientation of the object with respect to the camera is generally unknown. Various exemplary embodiments of systems and methods according to this invention cluster the located lines into groups that are classified as shown in FIGS. 28-32. It should be appreciated that different ones of the viewpoint-invariant line groups 700 shown in FIGS. 28-32 will correspond to features in differing ones of the wireframe models shown in FIG. 27. In particular, various different classes of viewpoint-invariant line groups 700 include the unconnected viewpoint-invariant line groups 700 shown in FIG. 28, the viewpoint-invariant line groups 720 and 730 having two lines connected at a single point shown in FIG. 29, the viewpoint-invariant line groups 740 and 750 having three lines connected at two points, as shown in FIG. 30, the viewpoint-invariant line groups 760 and 770 having three lines connected at a single point shown in FIG. 31 and the viewpoint-invariant line group 780 having three lines connected at three points shown in FIG. 32.

Figure 28:
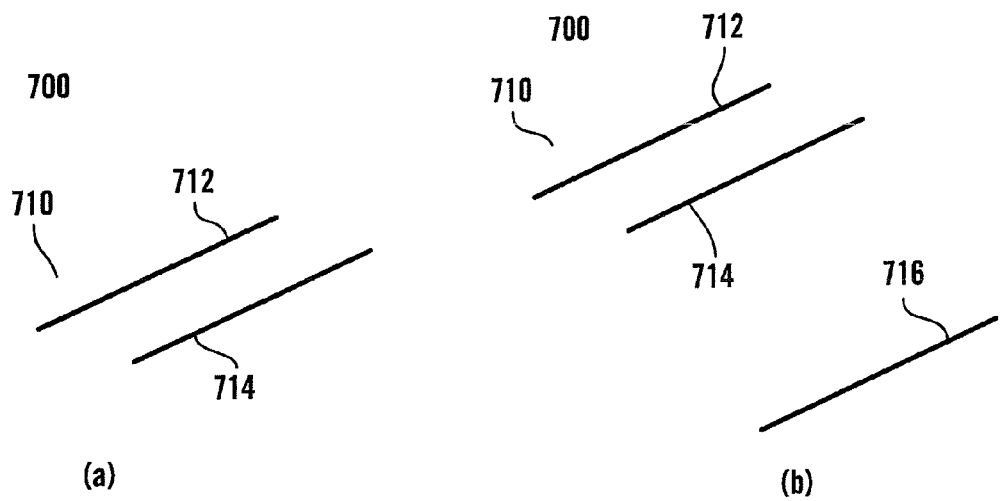
FIG. 28 shows a number of viewpoint-invariant line groups that are characterized by having a plurality of parallel lines.

As shown in FIG. 28, the class of unconnected viewpoint-invariant line group 710 includes the two line invariant line group 710 shown in portion (a) and the three-line group 710 shown in portion (b). In particular, the two line group 710 comprises the parallel lines 712 and 714 that are spaced a first distance apart. The three-line group 710 comprises the parallel line 712 and 714, as well as a third parallel line 716, which is typically spaced a different distance from the line 714 than the distance separating the lines 712 and 714.

Neither of the parallel type group 710 shown in FIG. 28 can be used to identify tetrahedral objects, while only the two-line parallel group 710 can be used to identify octahedral objects. In contrast, both the two-line and three-line groups 710 can be used to identify cubic or glycine-shaped objects. It should be appreciated that, based on the object shape to be identified, the parameters for the parallel type groups will include line length and perpendicular distance between lines.

Figure 29:
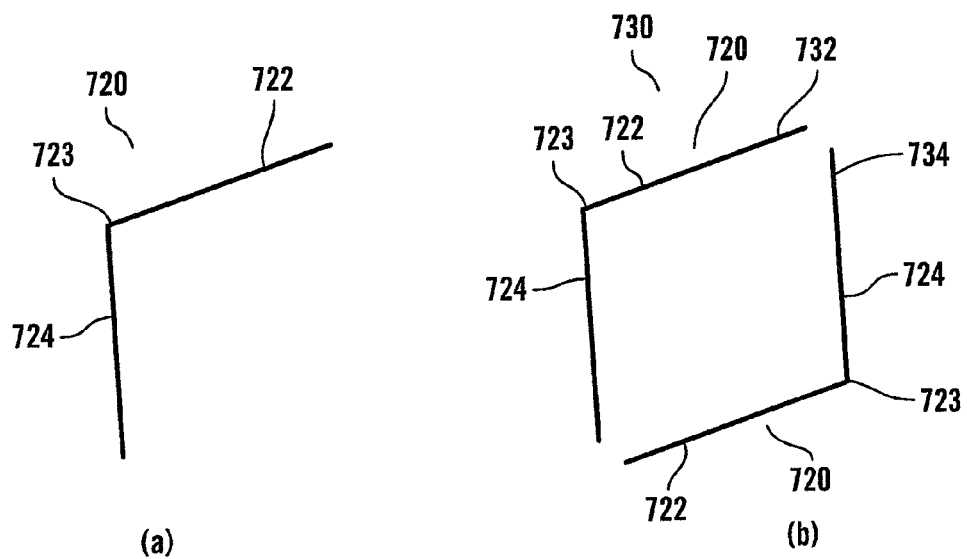
FIG. 29 shows viewpoint-invariant line groups characterized by having two lines joined at a single junction.
Figure 30:
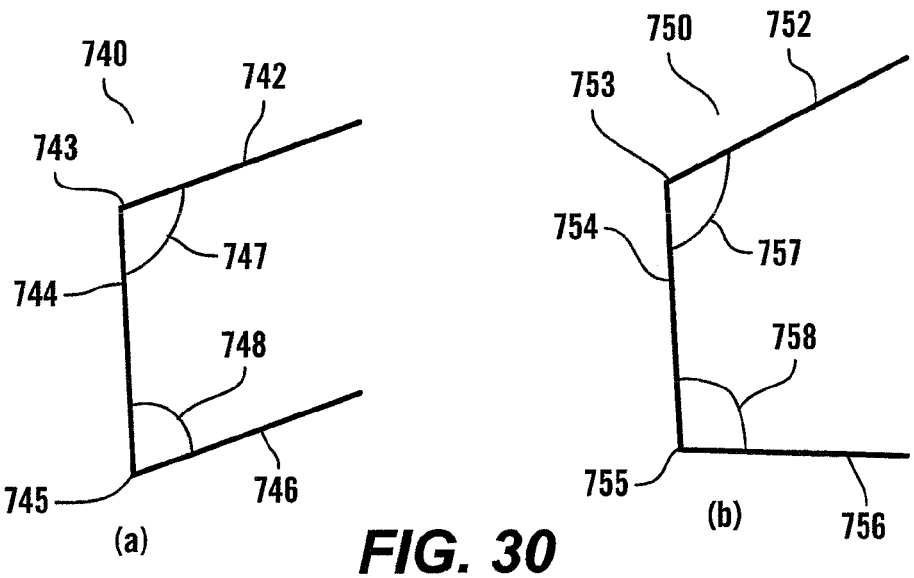
FIG. 30 shows a number of viewpoint-invariant line groups characterized by having three lines joined at two junctions.

FIG. 29 shows, in portion (a), a first junction type viewpoint-invariant line group 720. As shown in FIG. 29, the viewpoint-invariant line group 720 comprises a first line 722 and a second line 724 that meet at a junction or vertex 723. It should be appreciated that the angle between the two lines 722 and 724 will depend substantially on the type of object being recognized and the orientation of that object to the image plane. FIG. 29 shows, in section (b), a symmetric junction viewpoint-invariant line group 730 comprising two of the junction viewpoint-invariant line groups 720. In particular, the pair of symmetric junction viewpoint-invariant line groups 730 will include a first junction viewpoint-invariant line group 732 and a second junction viewpoint-invariant line group 734, where each of the first and second junctions viewpoint-invariant line groups 732 and 734 are individual junction viewpoint-invariant line group 720. The symmetric junctions viewpoint-invariant line groups 732 and 734 are symmetrical, in that they have generally the same line lengths for the edges 722 in each pair and the edges 724 in each pair. Likewise, the edges 722 or 724 in each pair will be generally parallel. Finally, the angles between the edges 722 and 724 in each of the symmetric pair 732 and 734 will be the same. Such symmetric pairs of junction viewpoint-invariant line groups 720 are likely to occur with cubic, glycine-shaped and parallelogram-faced objects, and can occur with octahedral objects, although it is less likely to occur.

FIG. 30 shows a square C-triple type viewpoint-invariant group 740 in portion (a) and a non-square C-triple viewpoint-invariant group 750 in portion (b). In particular, the square C-triple 740 comprises edges 742, 744 and 746 that are connected at junctions 743 between the edges 742 and 744 and 745 between the edges 744 and 746. In particular, for this square C-triple group 740, the angles 747 and 748 will be supplementary (i.e. sum to 180 degrees). Additionally, because the square C-triple group 740 will typically occur on an object that comprises at least in part a rectangular prism, such as a cubic object or a glycine-shaped object, the edges 742 and 746 will typically be the same length. For an object having at least a cubic portion, all of the edges 742, 744 and 746 will have the same length.

In contrast, the non-square C-triple group 750 has angles, 757 and 758 that are not both right angles or projections of right angles. In particular, the non-square C-triple group 750 shown in FIG. 30 comprises three edges 752, 754 and 756 that are connected by junctions 753 and 755. Such non-square C-triple viewpoint-invariant line groups 750 can occur in a variety of different types of objects, including a tetrahedral object, an octahedral object, and the glycine-shaped object. For example, for a tetrahedral object such as that shown in FIG. 27, for a given pose relative to the image plane, the edges 330, 310 and 350 can form such a non-square C-triple viewpoint-invariant line group 750. The edges 612, 622 and 632 or 658 of the glycine-shaped object 650 also form a non-square C-triple viewpoint-invariant line group 750.

It should be appreciated that the angles 757 and 758 can be both acute, both obtuse, one obtuse and one acute, and one of the angles 757 or 758 can be even a right angle or a projection of a right angle. It should be appreciated that the particular angles that a non-square C-triple viewpoint-invariant line group 750 can have will be dependent upon the particular type of object to be identified. For example, if tetrahedral objects are to be identified, the non-square C-triple viewpoint-invariant line group 750 will be limited to those having acute angles. In contrast, for the glycine-shaped object shown in FIG. 27, the angles 757 and 758 will be typically limited to obtuse or right angles. It should also be appreciated that, based on the type of object, the relative lengths of the edges 752, 754 and 756 may be constrained depending on how the edges are fit to the particular model.

Figure 31:
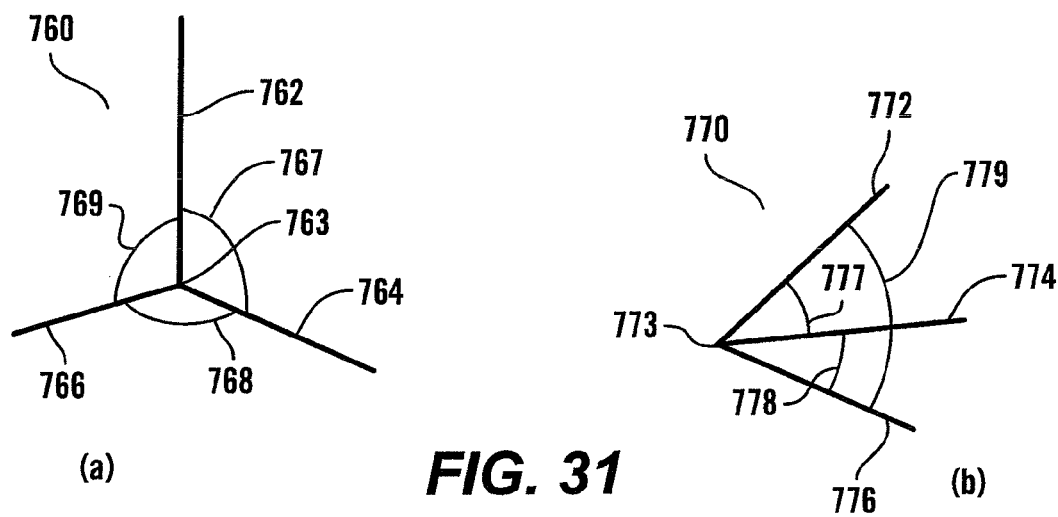
FIG. 31 shows a number of viewpoint-invariant line groups characterized by having three lines joined at a single junction.

FIG. 31 shows, in section (a), a Y-shaped viewpoint-invariant line group 760 and, in section (b), an arrow viewpoint-invariant line group 770. As indicated above, each of these line groups has three edges connected at a single junction. In particular, the Y-shaped viewpoint-invariant line group 760 comprises edges 762, 764 and 766 that are connected at a single junction 763. A first angle 767 extends between the edges 762 and 764, while a second angle 768 extends between the edges 764 and 766, and a third angle 769 extends between the edges 766 and 762. It should be appreciated that the angles 767, 768 and 769 sum to 360 degrees. The Y-shaped viewpoint-invariant line group 760 appears in many different types of objects, including a square object, a tetrahedron object, a glycine-shaped object and the like.

In contrast, the arrow-shaped viewpoint invariant line group 770, while also having three edges, 772, 774 and 776 that meet at a common junction 773, has angles 777, 778 and 779 that are each less than or equal to 180 degrees. In particular, at least one of the angles, such as the angle 777, which extends between the edges 772 and 774, or the angle 778, which extends between the edges 774 and 776, will be less than or equal to 90 degrees, and both can be less than or equal to 90 degrees. The angle 779 between the edges 772 and 776 is obviously the sum of the angles 777 and 778. The arrow-shaped viewpoint-invariant line group 770 also appears in a variety of different objects, including a tetrahedron, an octahedron, a glycine-shaped object or the like.

Figure 12A:
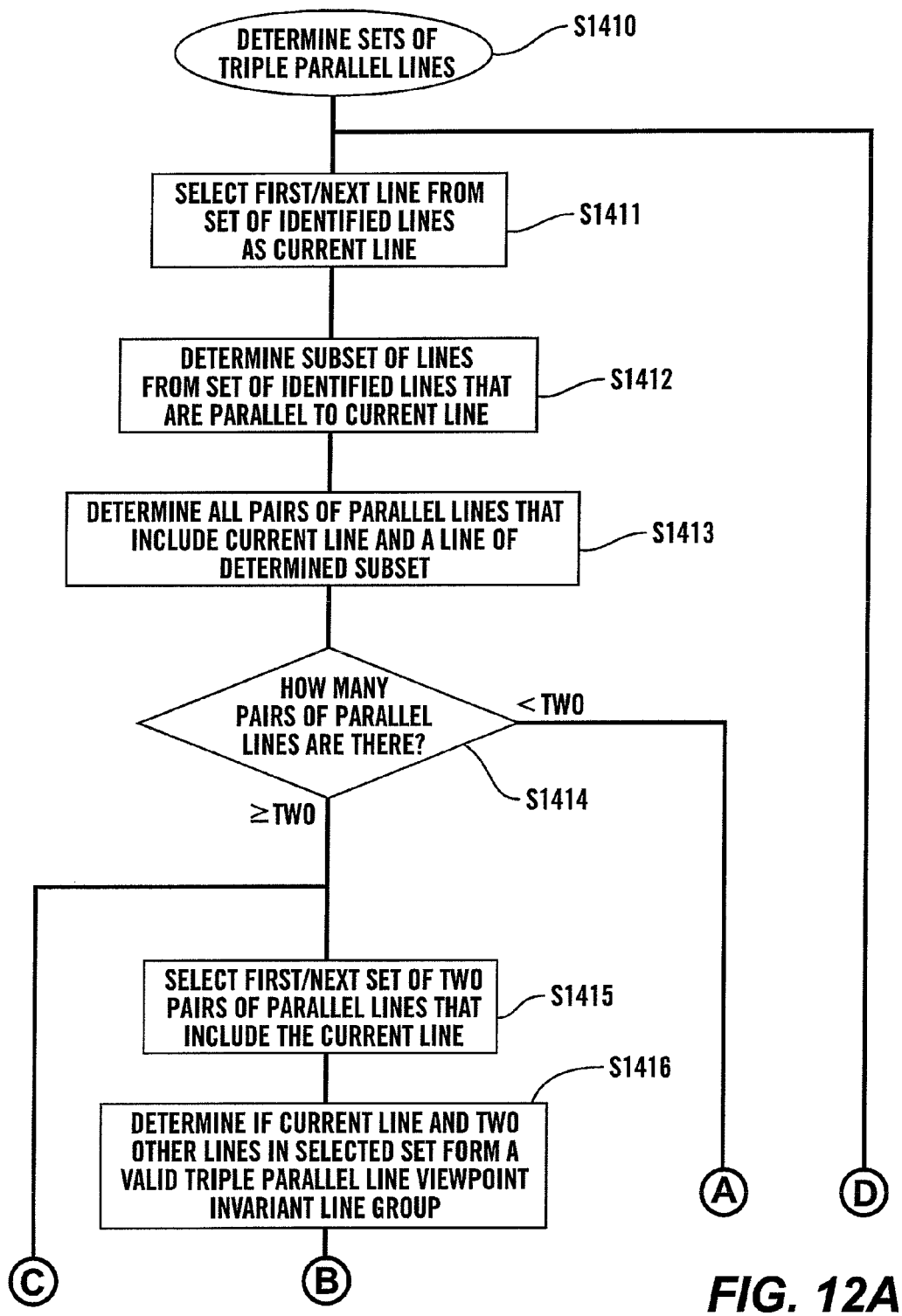
FIGS. 12A and 12B are a flowchart outlining a first exemplary embodiment of a method for determining sets of triple parallel lines from the identified linear features and/or the generated virtual lines.
Figure 12B:
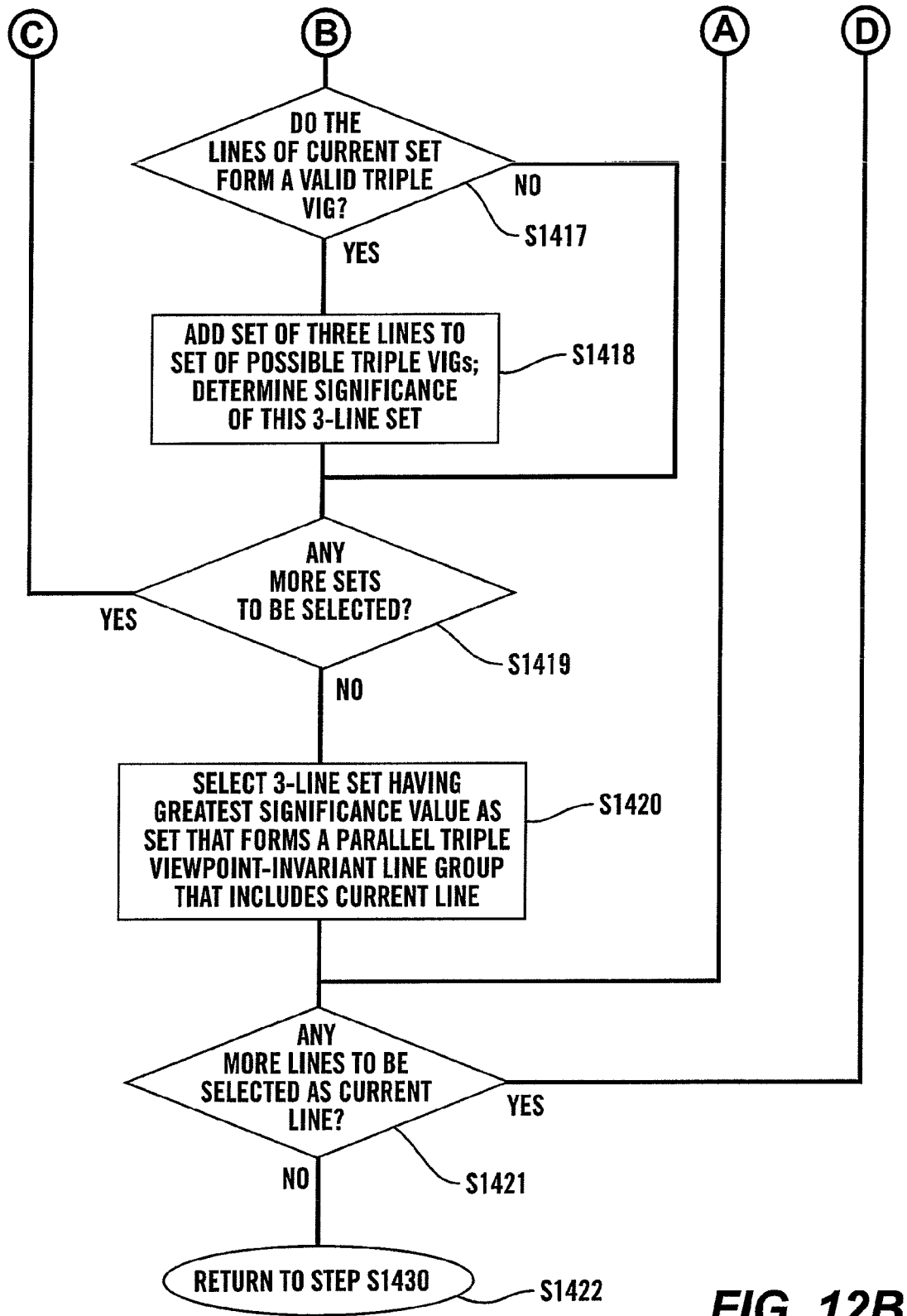
Figure 32:
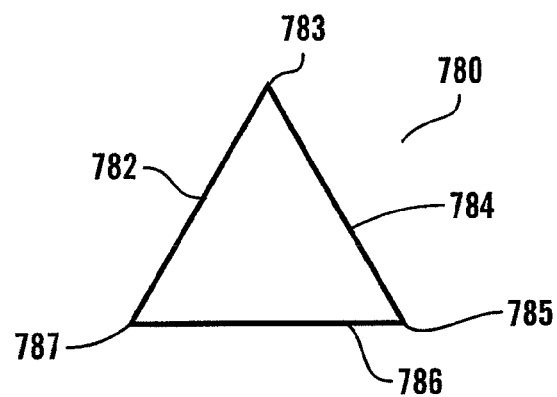
FIG. 32 shows a viewpoint-invariant line group characterized by having three lines joined at three junctions.

FIG. 32 shows a triangle viewpoint-invariant line group 780 comprising three edges, 782, 784 and 786 and three vertices, 783, which lies between the edges 782 and 784, 785, which lies between the edges 784 and 786, and 787, which lies between the edges 786 and 782. The triangle viewpoint-invariant line group 780 also appears in a variety of different objects, including a tetrahedron, an octahedron, glycine-shaped object and the like FIGS. 12A and 12B are a flowchart outlining a first exemplary embodiment of a method for determining sets of triple parallel lines from the identified linear features and/or the generated virtual lines. As shown in FIGS. 12A and 12B, beginning in step S1410, operation continues to step S1411, where a first line or a next line is selected as the current line from the set of identified linear features and/or the generated virtual lines. Then, in step S1412, a subset of the linear features and/or the generated virtual lines that are parallel to the current line are determined from the set of identified linear features and/or the generated virtual lines. Next, in step S1413, all pairs of parallel lines that include the current line and one of the lines of the determined subset of parallel lines are determined. Operation then continues to step S1414.

In step S1414, a determination is made regarding how many pairs of parallel lines were determined in step S1413. If there are less than 2 pairs, operation jumps to step S1421. Otherwise, if there are two or more pairs, operation continues to step S1415, where a first or next set of two pairs of the determined pairs of parallel lines that include the current line is selected. Then, in step S1416, the current line and the two other lines in the selected pair of determined pairs of parallel lines are analyzed to determine if these three lines form a valid triple parallel line viewpoint-invariant line group. Next, in step S1417, a determination is made whether these three lines form a valid triple parallel line viewpoint-invariant line group or VIG. If so, operation continues to step S1418. Otherwise, operation jumps to step S1419.

It should be appreciated that a valid parallel triple comprises three lines that do not share any linear features. That is, if the triple contains at least one virtual line, then it is possible that the virtual line was constructed from a linear feature that is either (1) part of another virtual line in the triple, or (2) one of the other lines in the triple. If either of these conditions is true, the parallel triple is not valid. Thus, a parallel triple is valid if it contains three linear features. A parallel triple is also valid if it contains two linear features and a virtual line that does not contain either linear feature as a constituent linear feature of that virtual line. A parallel triple is also valid if it contains one linear feature and two virtual lines, where neither virtual line contains that linear feature as a constituent linear feature. Finally, a parallel triple is also valid if it contains three virtual lines, where none of the virtual lines contains the same linear feature as one of the other virtual lines of that parallel triple.

Thus, a parallel triple would be invalid if a virtual line C was developed from the linear features A and B, and the parallel triple includes the virtual line C and either of the linear features A or B. The parallel triple would also be invalid if it included both the virtual line C discussed above and a virtual line E that was developed from the linear features A and D. Since the linear feature A is a constituent of both the virtual lines C and E, a parallel triple that includes both the virtual lines C and E is invalid.

In step S1418, the set of these three lines is added to the set of possible triple parallel line viewpoint-invariant line groups and the significance of this 3-line set is determined. It should be appreciated that the significance for a parallel pair i is $S_i$. A parallel triple includes two, overlapping parallel pairs i and j, each having a significance $S_i$ and $S_j$. In various exemplary embodiments, the significance for the parallel triple is $S_i \times S_j$. Next, in step S1419, a determination is made whether there are any more sets of two pairs of the determined pairs of parallel lines to be selected, i.e., sets that have not yet been examined. If so, operation jumps back to step S1415. Otherwise, if all of the sets of two pairs of the determined pairs of parallel lines have been selected, operation continues to step S1420. In step S1420, the 3-line set of parallel lines having the greatest significance value is selected as the set of three parallel lines that form a parallel triple viewpoint-invariant line group that includes current line and is added to a list of parallel triple viewpoint-invariant line groups. Operation then continues to step S1421.

It should be appreciated that, in some exemplary embodiments, if there are exactly two sets of paired parallel lines, steps S1415 and S1419 can be omitted. In this case, in step S1420, the single 3-line set of parallel lines resulting from the 2 sets of paired parallel lines is added to the list of parallel triple viewpoint-invariant line groups. Then, in step S1421, a determination is made whether there are any more lines to be selected, i.e., lines that have not yet been examined. If so, operation jumps back to step S1411. Otherwise, if all of the lines have been selected, operation continues to step S1422, which returns operation of the method to step S1430.

Figure 13A:
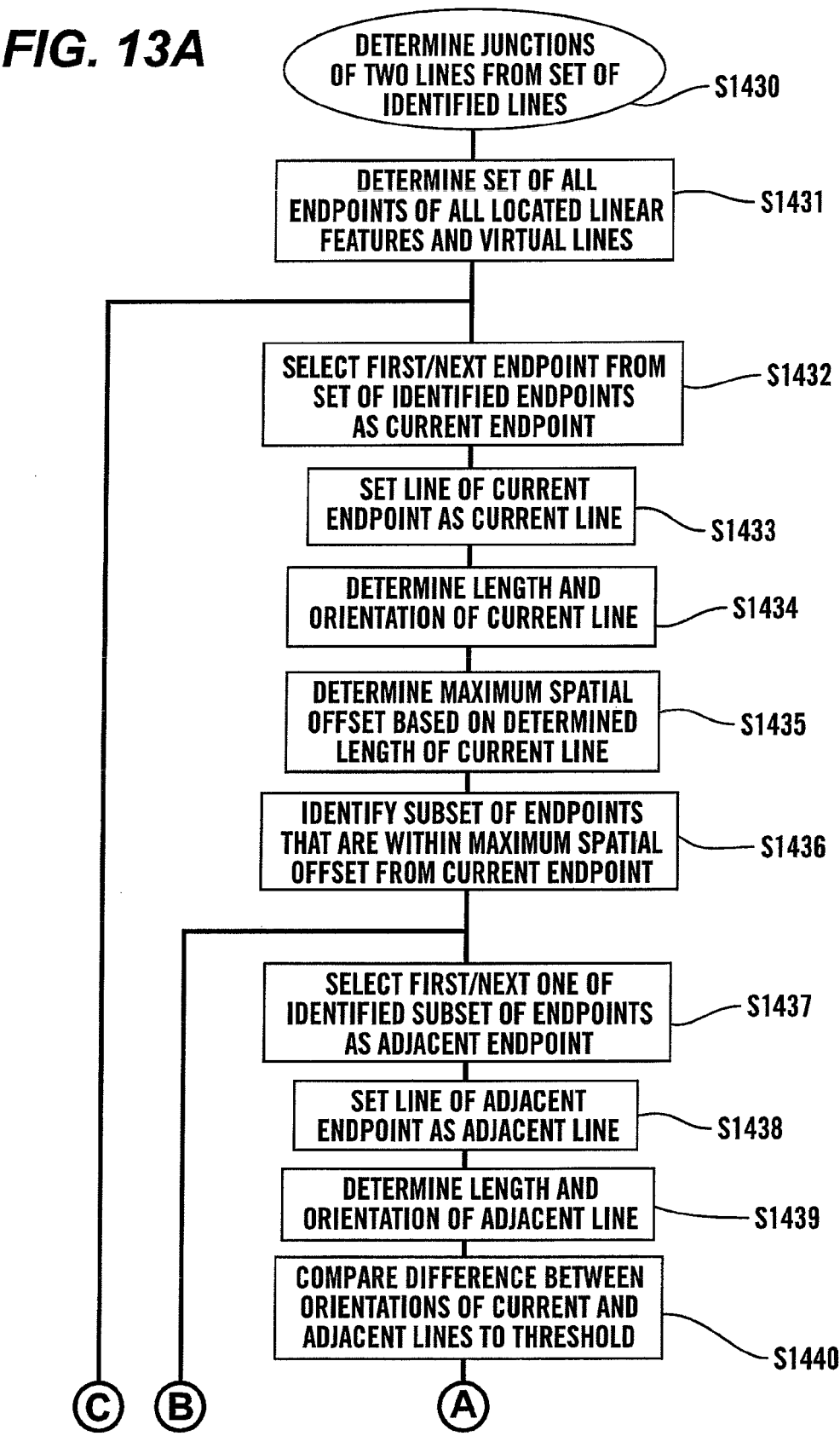
FIGS. 13A and 13B are a flowchart outlining a first exemplary embodiment of a method for determining one or more junctions of two lines from the identified linear features and/or the generated virtual lines.
Figure 13B:
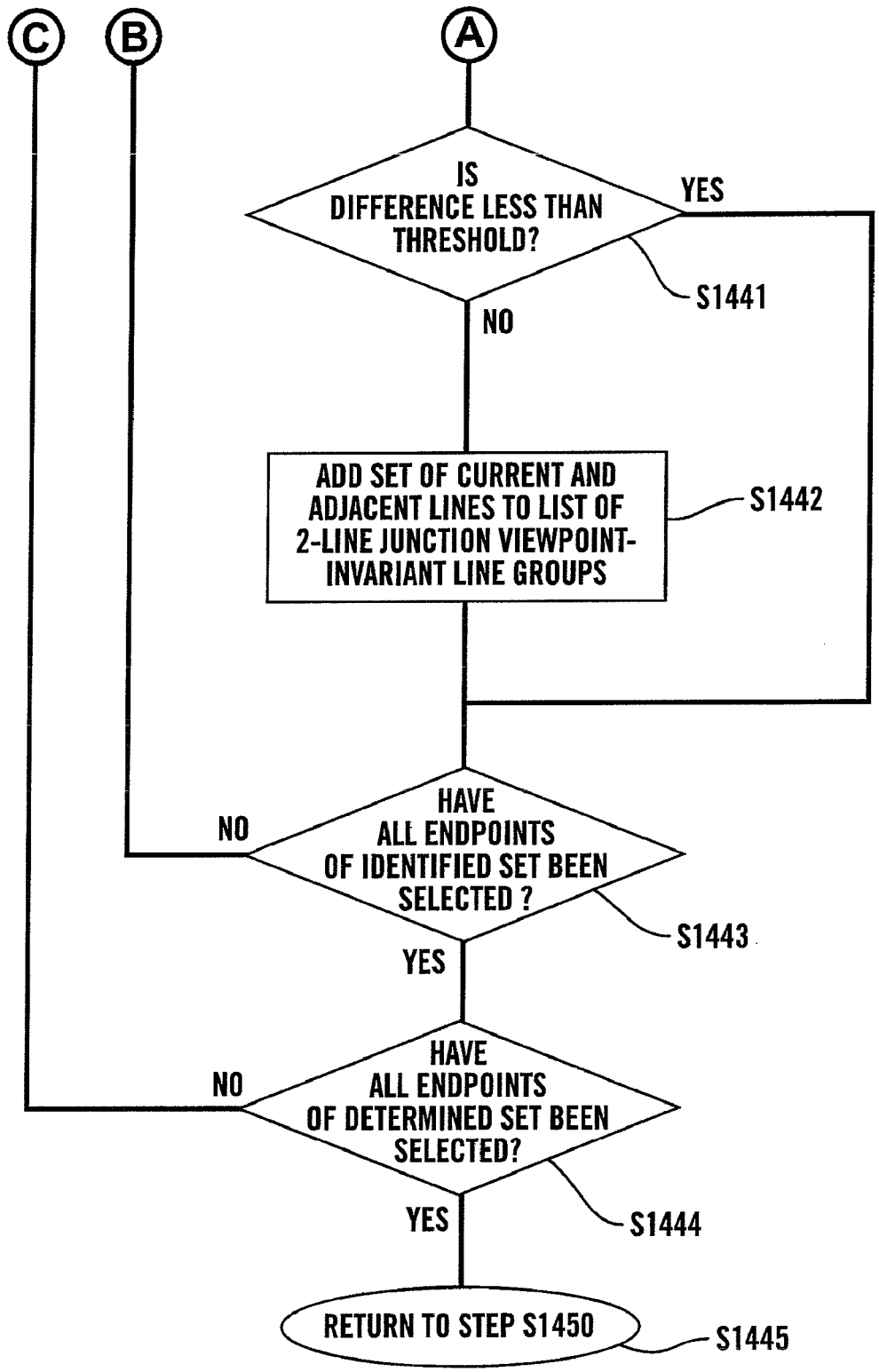

FIGS. 13A and 13B are a flowchart outlining a first exemplary embodiment of a method for determining one or more junctions of two lines from the identified linear features and/or the generated virtual lines. As shown in FIGS. 13A and 13B, beginning in step S1430, operation continues to step S1431, where a set of all endpoints of all identified linear features and/or generated virtual lines is determined. Next, in step S1432, a first endpoint or the next endpoint is selected as the current endpoint from the set of identified endpoints. Then, in step S1433, the line that includes the current endpoint is selected as the current line. Operation then continues to step S1434.

In step S1434, the length and the orientation of the current line are determined. Then, in step S1435, a maximum spatial offset for the current line is determined based on the determined length of the current line. Next, in step S1436, a subset of endpoints in the set of determined endpoints that are within the determined maximum spatial offset from the current endpoint is determined. Operation then continues to step S1437.

In step S1437, a first or next endpoint is selected from the identified subset of endpoints as the current adjacent endpoint. Next, in step S1438, the line that includes the current adjacent endpoint is selected as the current adjacent line. Then, in step S1439, the length and the orientation of the current adjacent line are determined Operation then continues to step S1440.

In step S1440, the difference between the orientations of the current line and the current adjacent line is compared to a threshold difference value. Then, in step S1441, a determination is made whether the difference is less than the threshold difference value. If not, operation continues to step S1442. Otherwise, operation jumps to step S1443. In step S1442, the set of the current line and the current adjacent line is added to a list of 2-line junction viewpoint-invariant line groups. Operation then continues to step S1443, where a determination is made whether there are any more endpoints in the determined subset to be selected. If so, operation jumps back to step S1437. Otherwise, if all of the endpoints of the subset have been selected, operation continues to step S1444. In step S1444, a determination is made whether there are any more endpoints of the determined set to be selected. If so, operation jumps back to step S1432. Otherwise, if all of the endpoints of the determined set have been selected, operation continues to step S1445, which returns operation of the method to step S1450.

Figure 14A:
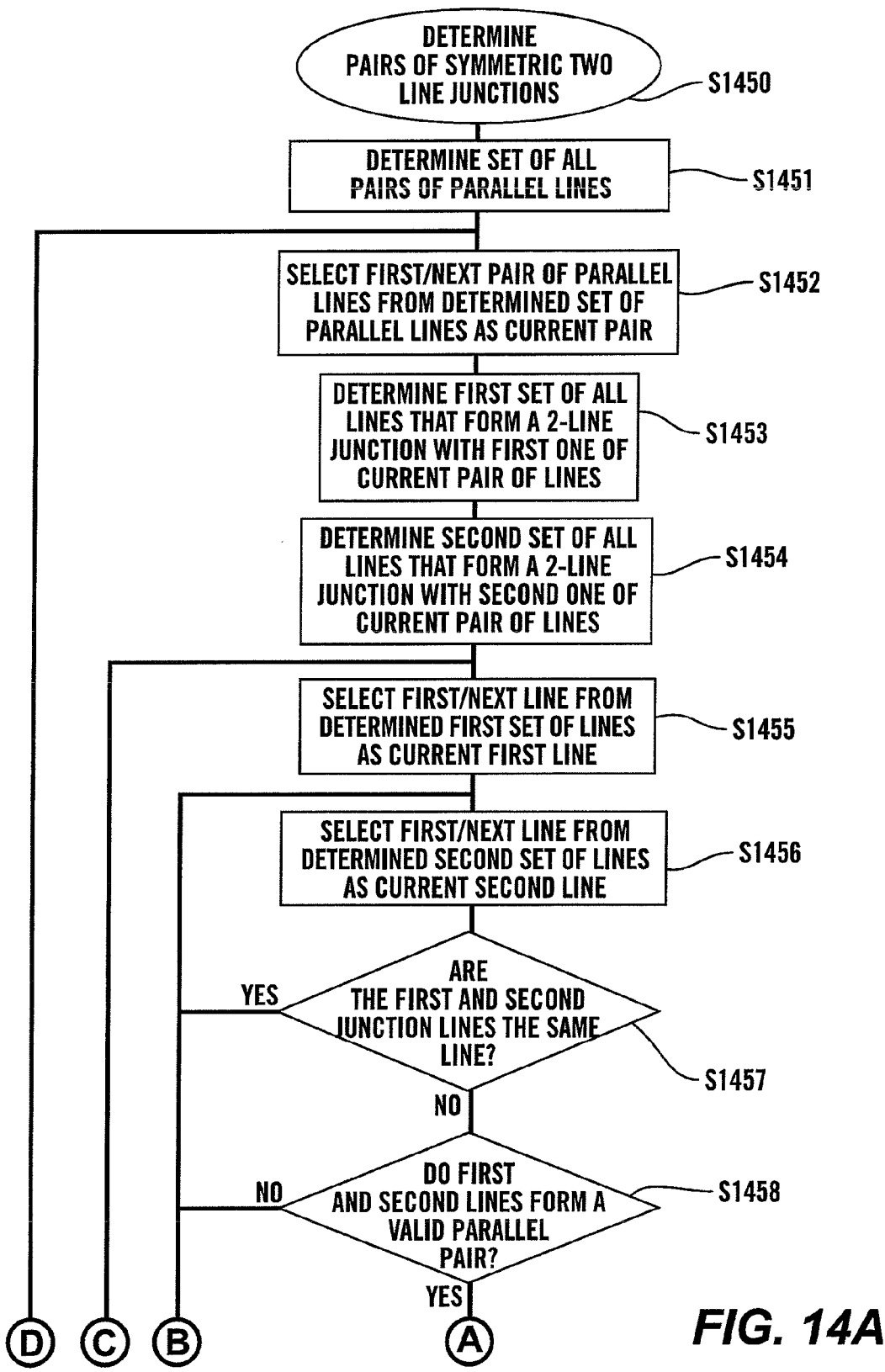
FIGS. 14A and 14B are a flowchart outlining a first exemplary embodiment of a method for determining or identifying any pairs of symmetric two-line junctions that occur within the set of determined 2-line junctions.
Figure 14B:
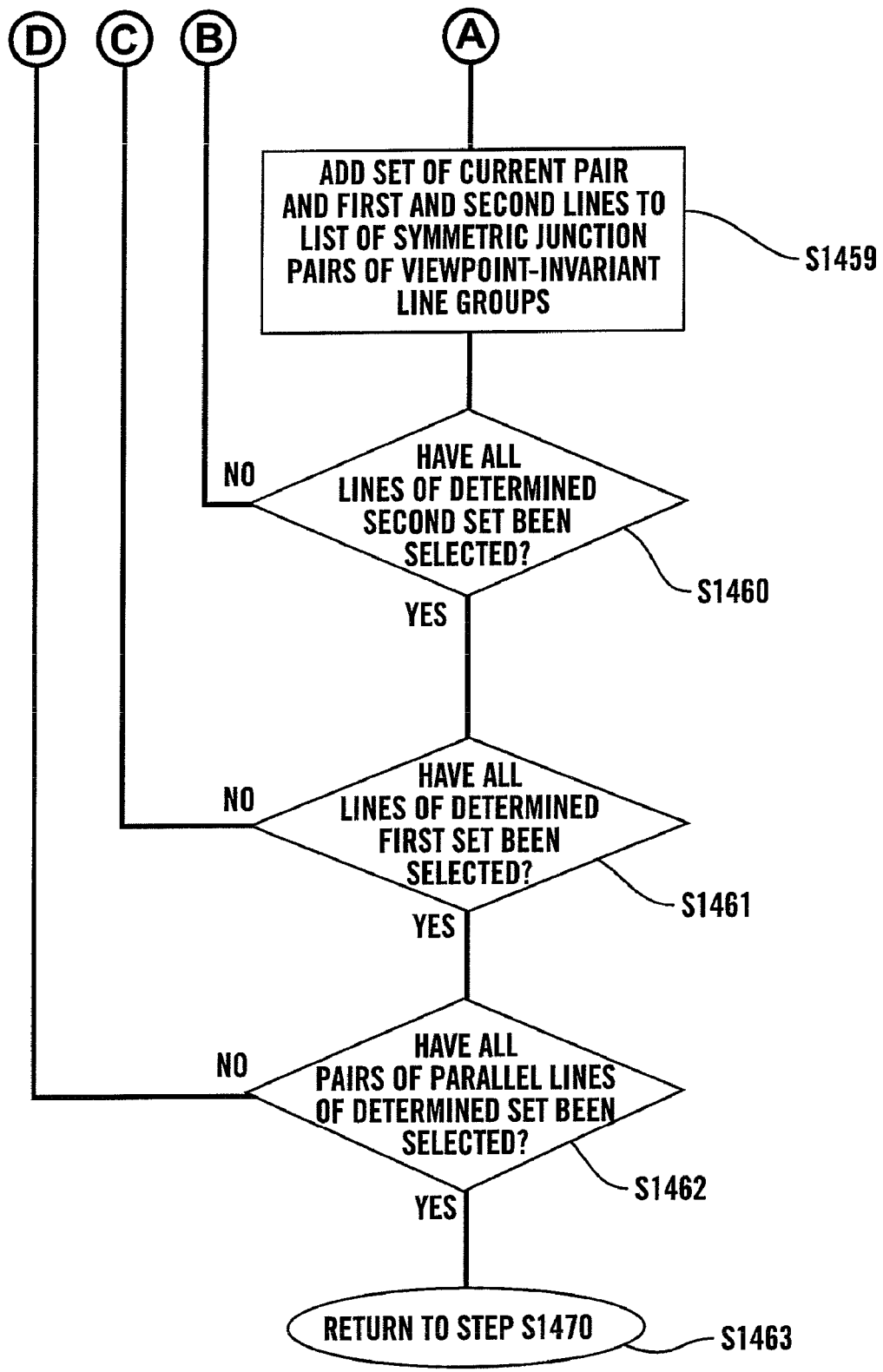

FIGS. 14A and 14B are a flowchart outlining a first exemplary embodiment of a method for determining or identifying any pairs of symmetric two-line junctions that occur within the set of determined 2-line junctions. As shown in FIGS. 14A and 14B, beginning in step S1450, operation continues to step S1451, where a set of all pairs of parallel lines is determined. Then, in step S1452, a first pair or the next pair of parallel lines is selected as the current pair of parallel lines from the determined set of parallel lines. Next, in step S1453, a first set of all lines, if any, that form a 2-line junction with a first one of current pair of lines is determined from the set of 2-line junction viewpoint-invariant line groups determined in step S1430. Operation then continues to step S1454.

In step S1454, a second set of all lines, if any, that form a 2-line junction with the second one of current pair of lines is determined from the set of 2-line junction viewpoint-invariant line groups determined in step S1430. Next, in step S1455, a first or next line is selected from the determined first set of lines as the current first line. Then, in step S1456, a first or next line is selected from the determined second set of lines as the current second line. Operation then continues to step S1457.

In step S1457, a determination is made whether the first and second junction lines are the same line. If so, operation jumps back to step S1456. Otherwise, if the first and second junction lines are not the same line, operation continues to step S1458. In step S1458, a determination is made whether the current first and second lines form a valid parallel pair. If not, operation again jumps back to step S1456. Otherwise, if the current first and second lines do form a valid parallel pair, operation continues to step S1459. In step S1459, the set of the current pair and the current first and second lines is added to a list of symmetric junction pairs of viewpoint-invariant line groups. Operation then continues to step S1460.

In step S1460, a determination is made whether there are any more lines in the determined second set of lines to be selected. If so, operation again jumps back to step S1456. Otherwise, if all of the lines in the determined second set of lines have been selected, operation continues to step S1461. In step S1461, a determination is made whether there are any more lines in the determined first set of lines to be selected. If so, operation jumps back to step S1455. Otherwise, if all of the lines in the determined first set of lines have been selected, operation continues to step S1462. In step S1462, a determination is made whether there are any more pairs of parallel lines of the determined set to be selected. If so, operation jumps back to step S1452. Otherwise, if all of the pairs of parallel lines of the determined set have been selected, operation continues to step S1463, which returns operation of the method to step S1470.

Figure 15A:
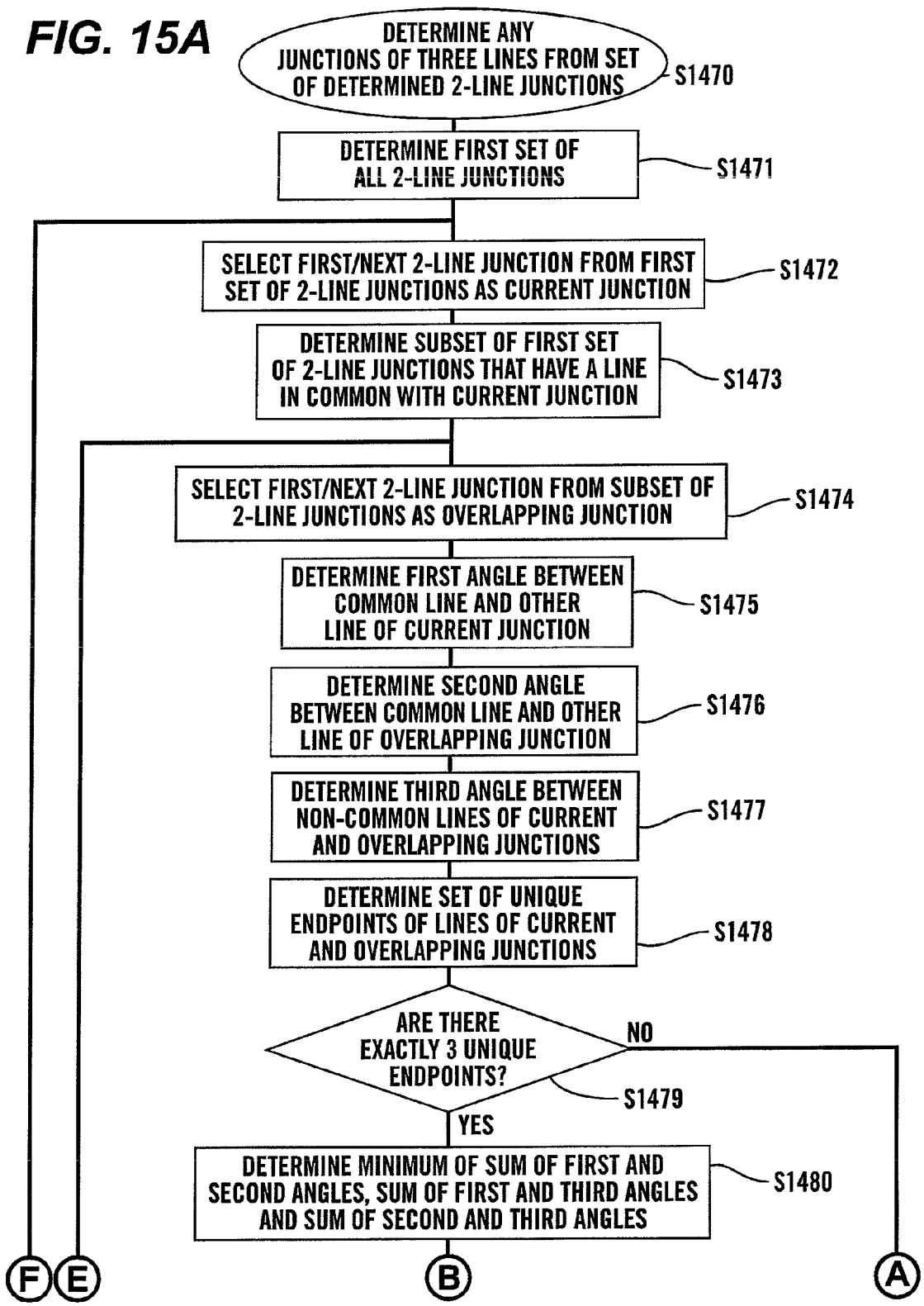
FIGS. 15A, 15B and 15C are a flowchart outlining a first exemplary embodiment of a method for determining or identifying any junctions of three lines occurring within the set of determined 2-line junctions.
Figure 15B:
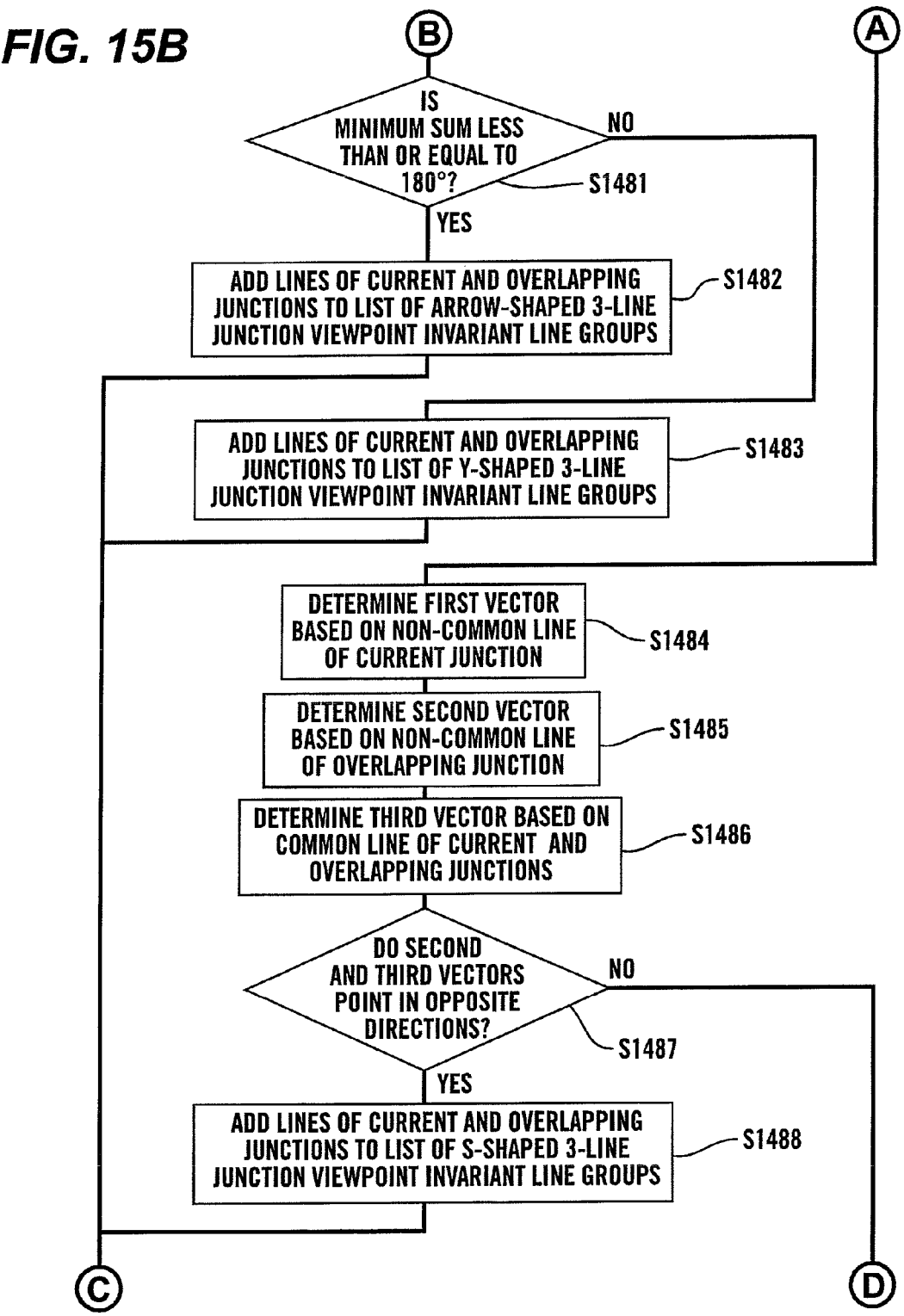
Figure 15C:
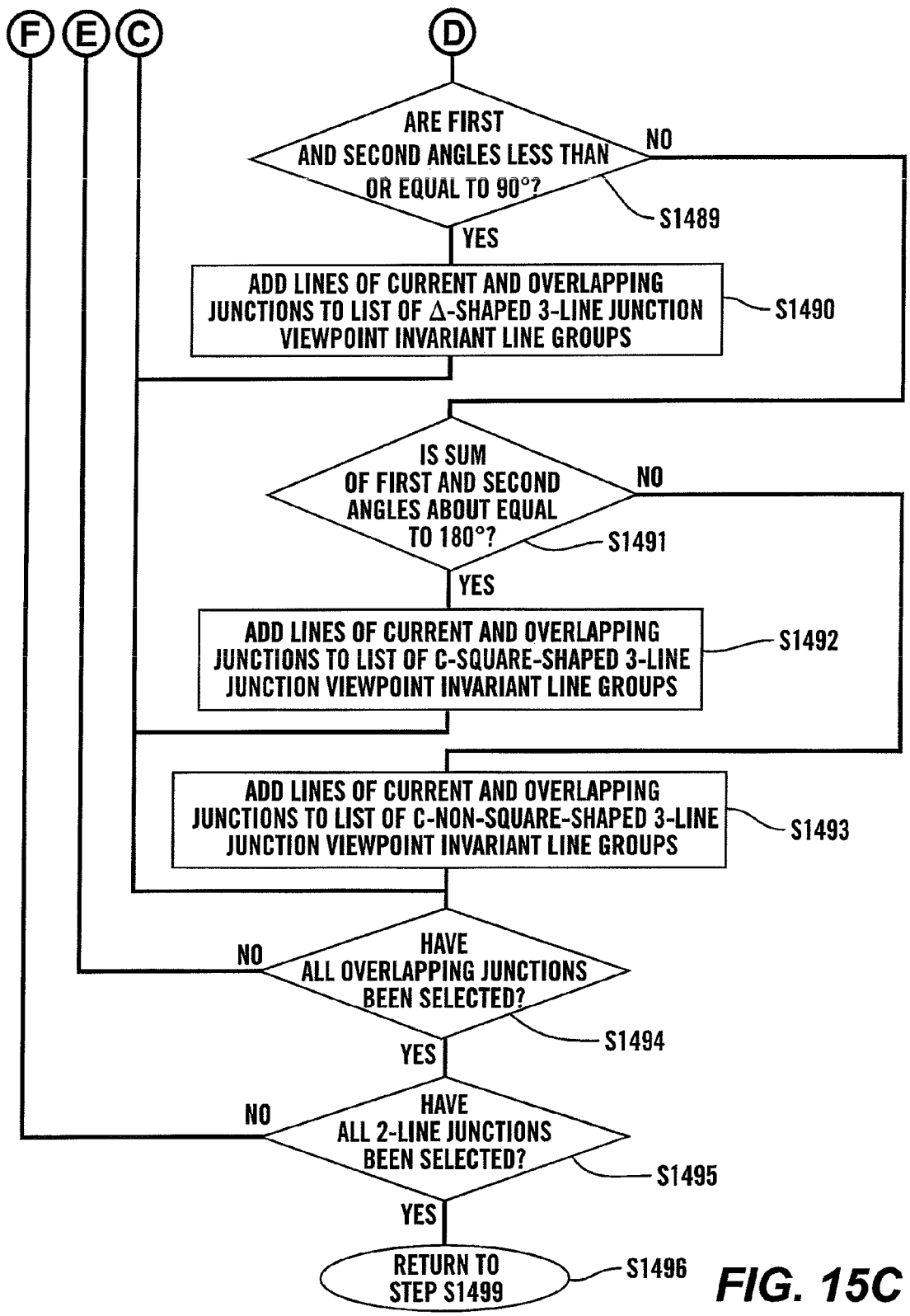

FIGS. 15A, 15B and 15C are a flowchart outlining a first exemplary embodiment of a method for determining or identifying any junctions of three lines occurring within the set of determined 2-line junctions. As shown in FIGS. 15A, 15B and 15C, beginning in step S1470, operation continues to step S1471, where a first set of all 2-line junctions is determined. Then, in step S1472, a first 2-line junction or the next 2-line junction is selected as the current 2-line junction from the determined first set of 2-line junctions. Next, in step S1473, a subset of the first set of 2-line junctions that have a line in common with the current 2-line junction is determined. Operation then continues to step S1474.

In step S1474, a first or next 2-line junction is selected as a current overlapping 2-line junction from the determined subset of 2-line junctions. Next, in step S1475, a first angle between the common line and the other line of the current 2-line junction is determined, where the line that is shared between the two 2-line junctions is the common line. Then, in step S1476, a second angle between the common line and the other line of the current overlapping 2-line junction is determined. Operation then continues to step S1477.

In step S1477, a third angle between the non-common lines of the current 2-line junction and the current overlapping 2-line junction, if it exists, is determined. Then, in step S1478, a set of unique endpoints of the three lines of the current 2-line junction and the current overlapping 2-line junction is determined. Next, in step S1479, a determination is made whether there are exactly 3 unique endpoints in the determined set of unique endpoints. If not, operation jumps to step S1484. Otherwise, if there are exactly 3 unique endpoints in the determined set of unique endpoints, operation continues to step S1480.

In step S1480, a minimum of the sum of the first and second angles, the sum of the first and third angles, if it exists, and the sum of the second and third angles, if it exists, is determined. Next, in step S1481, a determination is made whether the determined minimum sum is less than or equal to 180° C. If not, operation jumps to step S1483. Otherwise, if the determined minimum sum is less than or equal to 180° C., operation continues to step S1482, where the lines of the current 2-line junction and the current overlapping 2-line junction are added as an arrow-shaped 3-line junction viewpoint-invariant line group to a list of arrow-shaped 3-line junction viewpoint-invariant line groups. Operation then jumps to step S1494. In contrast, in step S1483, the lines of the current 2-line junction and the current overlapping 2-line junction are added as a Y-shaped 3-line junction viewpoint-invariant line group to a list of Y-shaped 3-line junction viewpoint-invariant line groups. Operation then again jumps to step S1494.

In contrast, in step S1484, a first vector based on the non-common line of the current 2-line junction is determined. Then, in step S1485, a second vector based on the non-common line of the current overlapping 2-line junction is determined. Next, in step S1486, a third vector based on the common line of the current 2-line junction and the current overlapping 2-line junction is determined. Then, in step S1487, a determination is made whether the first and second vectors point in opposite directions. If not, operation jumps to step S1489. Otherwise, if the second and third vectors do point in generally opposite directions, operation continues to step S1488. In step S1488, the lines of current 2-line junction and the current overlapping 2-line junction are added as an S-shaped 3-line junction viewpoint-invariant line group to a list of S-shaped 3-line junction viewpoint-invariant line groups.

In step S1489, a determination is made whether the first and second angles are both less than or equal to 90°, and at least one of the first and second angles is substantially less than 90°. If not, operation jumps to step S1491. Otherwise, if the first and second angles are both less than or equal to 90°, and at least one of the first and second angles is substantially less than 90°, operation continues to step S1490. In step S1490, the lines of the current 2-line junction and the current overlapping 2-line junction are added as a Δ-shaped 3-line junction viewpoint-invariant line group to a list of Δ-shaped 3-line junction viewpoint-invariant line groups. Operation then again jumps to step S1494.

In step S1491, a determination is made whether the sum of the first and second angles is about equal to 180°. If not, operation jumps to step S1493. Otherwise, if the sum of the first and second angles is about equal to 180°, operation continues to step S1492. In step S1492, the lines of the current 2-line junction and the current overlapping 2-line junction are added as a C-square-shaped 3-line junction viewpoint-invariant line group to a list of C-square-shaped 3-line junction viewpoint-invariant line groups. Operation then again jumps to step S1494. In contrast, in step S1493, the lines of the current 2-line junction and the current overlapping 2-line junction are added as a C-non-square-shaped 3-line junction viewpoint-invariant line group to a list of C-non-square-shaped 3-line junction viewpoint-invariant line groups. Operation then continues to step S1494.

In step S1494, a determination is made whether there are any more 2-line junctions in the determined subset of 2-line junctions having a line in common with the current 2-line junction to be selected. If so, operation jumps back to step S1474. Otherwise, if all of the 2-line junctions in the determined subset of 2-line junctions have been selected, operation continues to step S1495. In step S1495, a determination is made whether there are any more 2-line junctions of the determined set of 2-line junctions to be selected. If so, operation jumps back to step S1472. Otherwise, if all of the 2-line junctions of the determined set of 2-line junctions have been selected, operation continues to step S1496, which returns operation of the method to step S1499.

It should be appreciated that the methods outlined above and shown in FIGS. 12-15 are not the exclusive ways in which to determine or cluster the lines in the obtained image into the various viewpoint-invariant line groups. Thus, it should be appreciated that these disclosed methods are intended to illustrate how various viewpoint-invariant line groups may be identified, rather than limit the invention to these embodiments. Likewise, depending on the shape of the 3-dimensional object(s) to be identified in the obtained image, various ones of the viewpoint-invariant line groups may not be necessary or desirable, and their generation may be omitted from the above-outlined methods. Likewise, other viewpoint-invariant line groups may be necessary or desirable to identify the 3-dimensional object(s) in the obtained image, and thus their generation may be added to the above-outlined methods.

It should be appreciated that, as outlined above, different ones of the various viewpoint-invariant line groups 700-780 will be useful in recognizing different types of objects. Additionally, the particular angles that will occur between the edges in various ones of the viewpoint-invariant line groups 700-780 and the lengths of the edges will depend on the orientation and size of the particular object in the image.

As outlined above, to locate instances of a particular object that occur in an obtained image, the located lines, i.e. linear features and virtual lines, are analyzed to identify occurrences of the various viewpoint independent line groups 700 that are present in the wire frame model of each different object to be located or identified. It should be appreciated that systems and methods according to this invention are not limited to locating a single object in the obtained image. Rather, the determined viewpoint-invariant line group 700 can be analyzed in view of a variety of differently-shaped objects, each having a different model.

It should be appreciated that, in various exemplary environments, all occurrences of all of the different viewpoint independent groups that are present in a particular wire frame model of an object are identified. For each such identified viewpoint independent group, a significance measure for that identified viewpoint independent line group is determined based on the line lengths, endpoint distances for a viewpoint-invariant line group that has one or more junctions and/or orientation differences for viewpoint-invariant line groups having parallel lines. This significance measure is described in "3-Dimensional object recognition from single two-dimensional images," D. G. Lowe, Artificial Intelligence 31 (3) 355-395, 1987, incorporated by reference herein in its entirety. In exemplary embodiments where such significance measurements are generated, the significance measures are used to order the identified viewpoint independent line groups from the most to least visually salient, with the most visually salient independent line groups considered first in the model-fitting stage.

Figure 33:
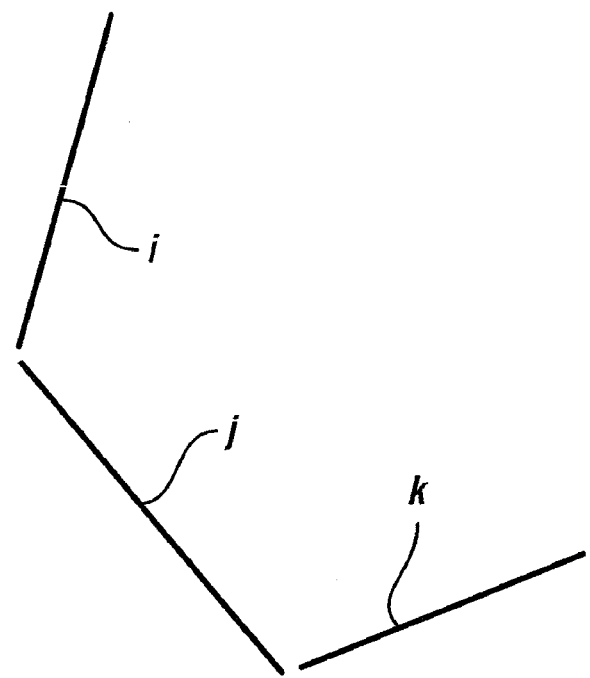
FIG. 33 shows three lines obtained from an image according to this invention that are identified as a C-junction type viewpoint-invariant line group.
Figure 34:
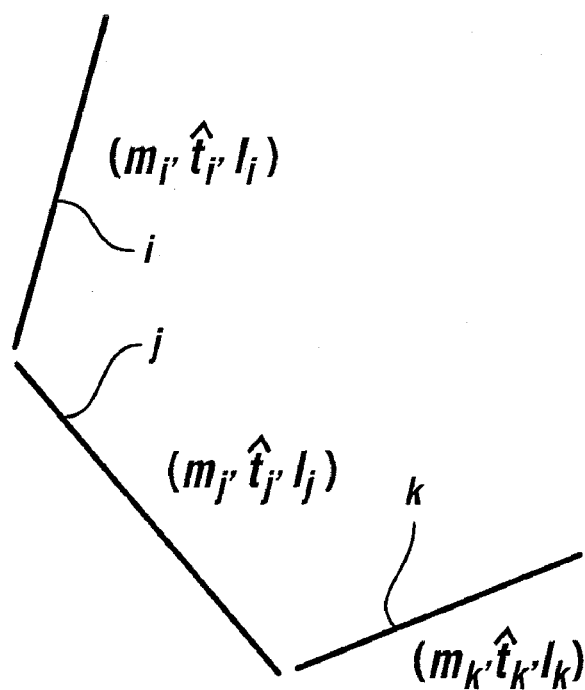
FIG. 34 illustrates how the lines shown in FIG. 33 are parameterized.

As outlined above with respect to step S1500 of FIG. 4, after generating the set of viewpoint-invariant line groups, the model of the one or more objects to be identified or located in the obtained images are fit to at least some of the viewpoint-invariant line groups that were identified in step S1400 of FIG. 4. FIG. 33 shows one such exemplary viewpoint independent line group. In particular, the viewpoint independent line group shown in FIG. 33 is a non-square C-triple 750. In particular, the edges of this viewpoint independent line group are identified as the i, j and k edges. Accordingly, as shown in FIG. 14, each of these i j and k edges are parameterized as outlined above.

Fitting the model to the selected viewpoint independent line group comprises determining the model parameters and viewpoint parameters such that a two-dimensional projection of the geometric wireframe model matches the low-level features extracted from the image that are captured in the viewpoint-invariant line group. Because the viewpoint and model parameters, such as size or orientation, etc., are, by definition, unknown, the viewpoint-invariant line group provides the starting point for fitting the model to the located lines of the selected viewpoint-invariant line group. As outlined in FIG. 9, to fit the model to these located lines of the selected viewpoint-invariant line group, it is first desirable to determine how the located viewpoint-invariant line groups correspond to the various edges in each of the one or more wireframe models.

Figure 16:
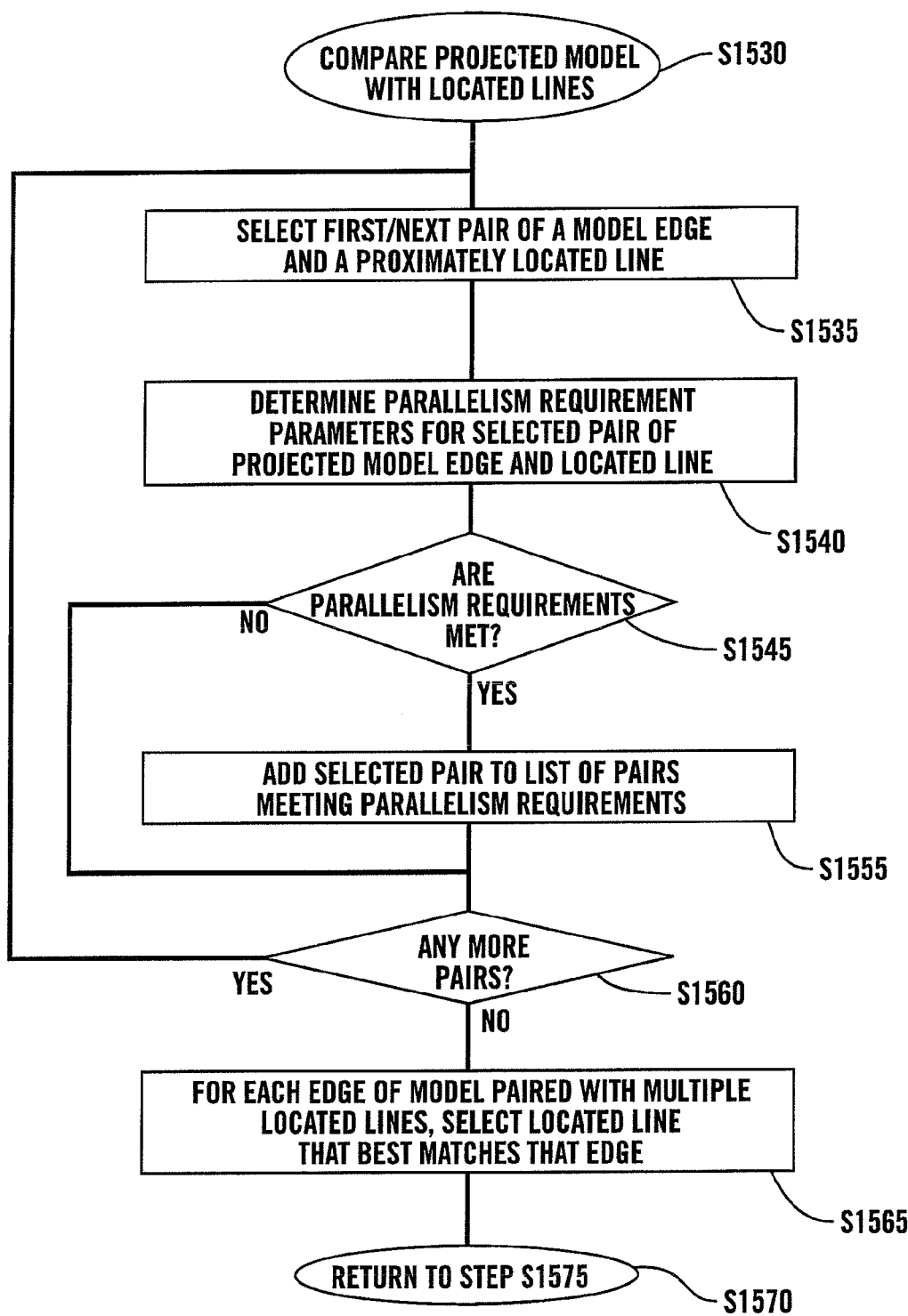
FIG. 16 is a flowchart outlining one exemplary embodiment of a method for comparing located lines to projected model lines.

FIG. 16 is a flowchart outlining a first exemplary embodiment of a method for comparing, for each hypothesis, in turn, edges of the projected object model of that particular hypothesis with the located lines in the obtained image according to this invention. As shown in FIG. 16, beginning in step S1530, operation continues to step S1535, where, for each hypothesis in turn, a first or next pair of an edge of the projected object model for that hypothesis, where the edge does not correspond to one of the lines of the current viewpoint-invariant line group, and a located line, i.e., located linear feature or generated virtual line, that is proximate to that edge, are selected for analysis. Then, in step S1540, one or more parallelism parameters for the selected projected object model edge and the selected located line are determined. Next, in step S1545, a determination is made whether the determined parallelism requirements are met. If so, operation continues to step S1555. Otherwise, operation jumps directly to step S1560. It should be appreciated that the "parallelism" requirements will typically depend on the spatial relationships between the particular edge of the object model in the pair being analyzed and the selected located line.

In step S1555, because the parallelism requirements have been met in step S1545, the selected pair of elements is added to a list of pairs that meet the parallelism requirements. Then, in step S1560, a determination is made whether any more pairs need to be selected and analyzed. If so, operation returns to step S1535. Otherwise, operation continues to step S1565, where, for each edge or line of the projected object model that has been paired with two or more located lines, a located line that best matches the edge that it is paired with is added as an additional line of the object to the viewpoint-invariant line group. It should be appreciated that, in looking for matches between the model edges and the located lines, there may be multiple located lines that satisfy the parallelism requirements with a single model edge. It should be appreciated that, in various exemplary embodiments, where there are multiple matches with a single model edge, the "best" match is selected based on a "quality" of the match. Of course, if there are no located lines that match the parallelism requirement, step S1565 can be skipped. Operation then continues to step S1570, which returns operation of the method to step S1575.

Figure 17:
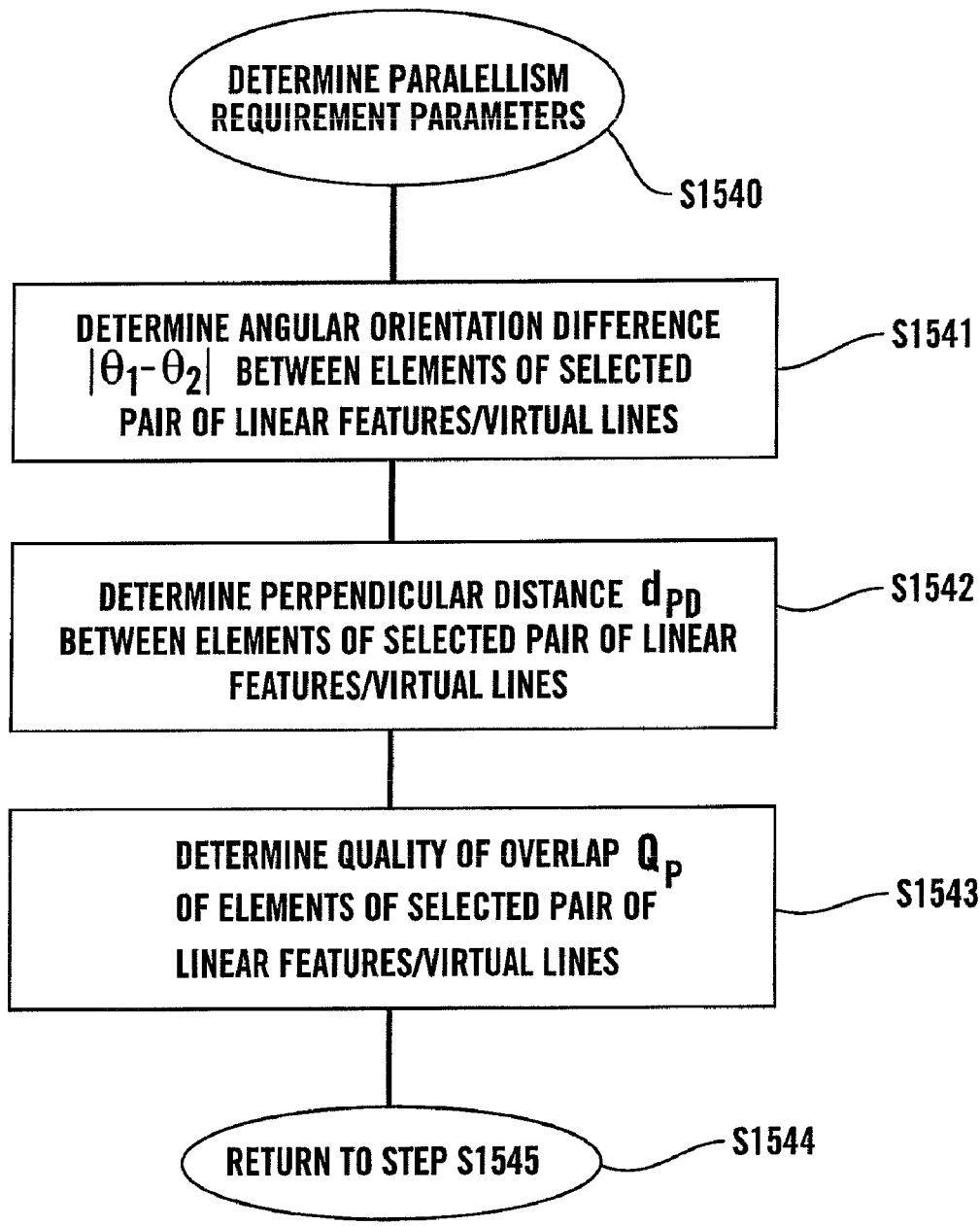
FIG. 17 is a flowchart outlining one exemplary embodiment of a method for determining parallelism requirement parameters for linear features and/or virtual lines relative to unmatched projected edges.

FIG. 17 is a flowchart outlining a first exemplary embodiment of a method for determining the angularity parameters of step S1540. As shown in FIG. 17, beginning in step S1540, operation of the method continues to step S1541, where the angular orientation difference $\Delta\theta$ between the linear features and/or virtual lines of the selected pair of elements is determined. In particular, $\Delta\theta$ is determined as outlined above, except that the input angles $\theta1$ and $\theta2$ represent the orientations of a different set of elements. Next, in step S1542, the determined perpendicular distance $d_{PD}$ between the linear features and/or virtual lines of the selected pair of elements is determined as outlined above. Again, this perpendicular distance $d_{PD}$ is the perpendicular distance for a distinct pair of linear features and/or virtual lines. Then, in step S1543, a quality of overlap measure $Q_p$ for the linear features and/or virtual lines of the selected pair of elements is determined. In particular, in various exemplary embodiments, the quality of the overlap is defined as:

$$Q_P = (l^P_1 + l^P_2)/2l_v, \quad (14)$$

where:

$l^P_1$ and $l^P_2$ are the projected lengths of the pair of selected projected edge and selected located line onto a new virtual line, as outlined above with respect to FIG. 6 for that selected pair; and $l_v$ is the length of that new virtual line.

It should be appreciated that this overlap quality measure $Q_P$ is scale independent, as it depends only on the relative lengths of the lines. Overlapping pairs give a $Q_P$ of between 0.5 and 1. In particular, a value of 0.5 represents that the lines overlap only at their endpoints, while a value of 1 represents that the lines perfectly overlap. Operation then continues to step S1544, which returns operation of the method to step S1545.

Figure 18:
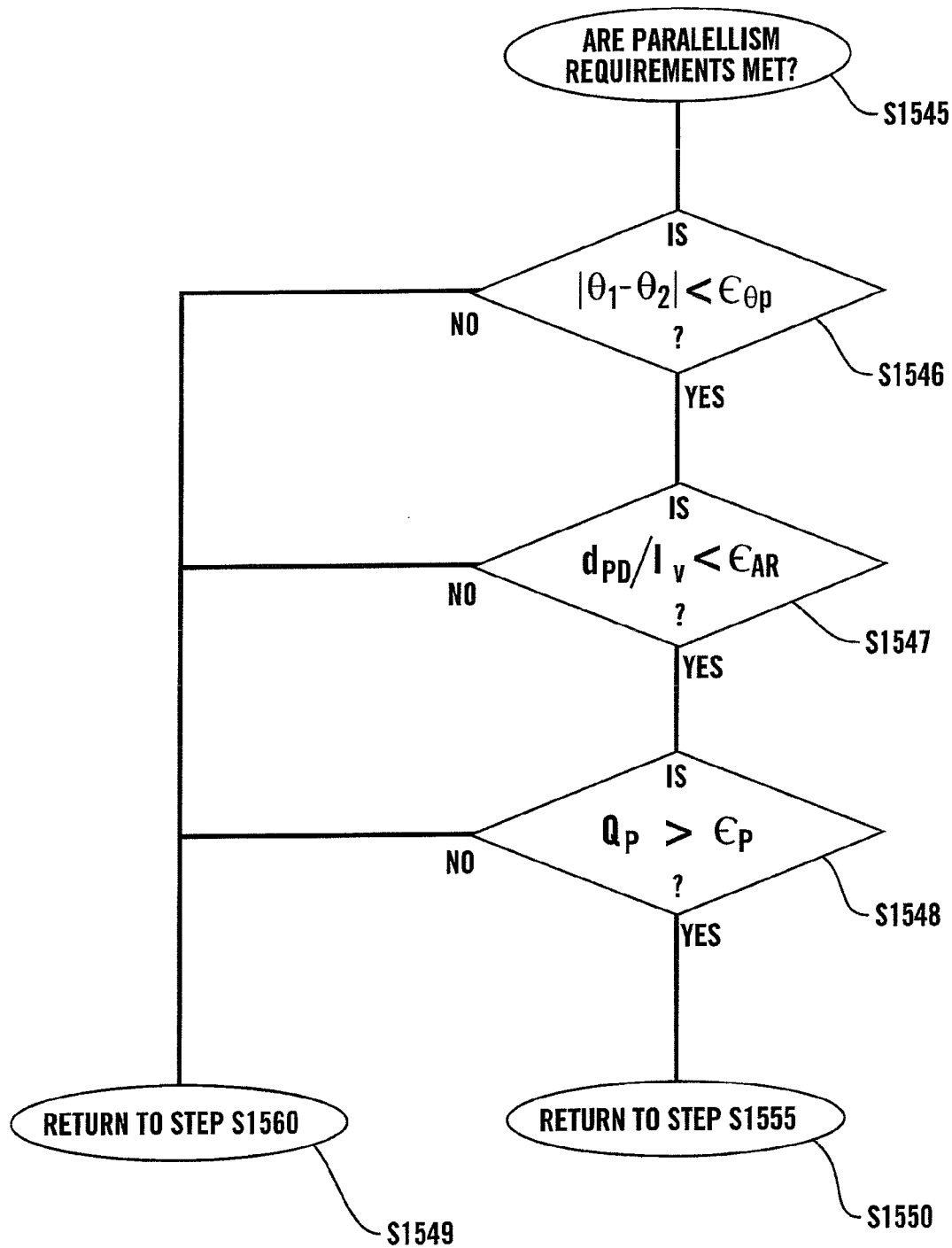
FIG. 18 is a flowchart outlining one exemplary embodiment of a method for determining if the parallelism requirements are met.

FIG. 18 is a flowchart outlining one exemplary embodiment of a method for determining if the parallelism requirements of step S1545 are met. As shown in FIG. 18, operation of the method begins in step S1545, and continues to step S1546, where a determination is made whether the angular orientation difference $\Delta\theta$ meets the criterion:

$$\Delta\theta = |\theta_1 - \theta_2| < \epsilon_{\theta P}, \quad (15)$$

where $\epsilon_{\theta P}$ is a user specified threshold. If the absolute value of the angular orientation difference $\Delta\theta$ is less than $\epsilon_{\theta P}$, operation continues to step S1547. Otherwise, operation jumps to step S1549.

In step S1547, a determination is made whether the ratio of the length of the new virtual line $l_v$ to the perpendicular off-set distance $d_{PD}$ is greater than a user specified threshold $\epsilon_{AR}$. That is, whether the perpendicular off set distance $d_{PD}$ meets the criterion:

$$l_V/d_{PD} > \epsilon_{AR}. \quad (16)$$

If so, operation continues to step S1548. Otherwise, operation again jumps directly to step S1549.

In step S1548, a determination is made whether the overlap quality measure $Q_P$ is greater than the user specified quality threshold $\epsilon_P$. That is whether the overlap quality measure $Q_P$ meets the criterion:

$$Q_P > \epsilon_P. \quad (17)$$

If so, all of the angularity requirements are met and operation jumps to step S1550, which returns control of the method to step S1555. Otherwise, operation continues to step S1549. Step S1549, which is reached when any one or more of the parallelism requirements are not met, returns operation of the method to step S1560.

It should be appreciated that, in various exemplary embodiments according to this invention, to obtain appropriate results, the overlap quality threshold $\epsilon_P$ should be quite high, such as, for example, on the order of 0.86 or higher.

It should be appreciated that, in step S1555, a significance measure can be used to determine which of two or more lines best fit a particular edge of a projected object model. One potential significance measure of each pair that meets the linearity requirements that can be used is based on the probability that that pair of linear features and/or virtual features will occur. That is, the significance measure is determined using a probability-based metric suggested in "3-Dimensional Object Recognition from Single Two-Dimensional Images", D. G. Lowe, Artificial Intel, 31(3): 355-395, 1987., which is incorporated herein by reference in its entirety. In particular, the metric suggested by Lowe for the significance S is:

$$S = 180° l^2_{min}/(4\Delta\theta d_{pd} l_{max}), \quad (18)$$

where:

$l_{min}$ is the length of the shorter one of the projected edge and the selected located line in the pair of the projected edge and the selected located lines:

$l_{max}$ is the length of the longer one of the pair of the projected edge and the selected located lines; and $\Delta\theta$, as outlined above, is a magnitude of the angular difference, in degrees, in the orientations of the pair of the projected edge and the selected located lines.

It should be appreciated that this metric is based on the assumption that the line orientations are uniformly distributed and that the density of line segments of lengths that are greater than a given length l is $l/l^2$. This significance measure gives higher significance to longer linear features or virtual lines. It should be appreciated, that in general, the significance comes into play only when there is a conflict between high quality matches between the projected edge and two or more located lines. Thus, the significance measure will favor the longer located line.

Figure 36:
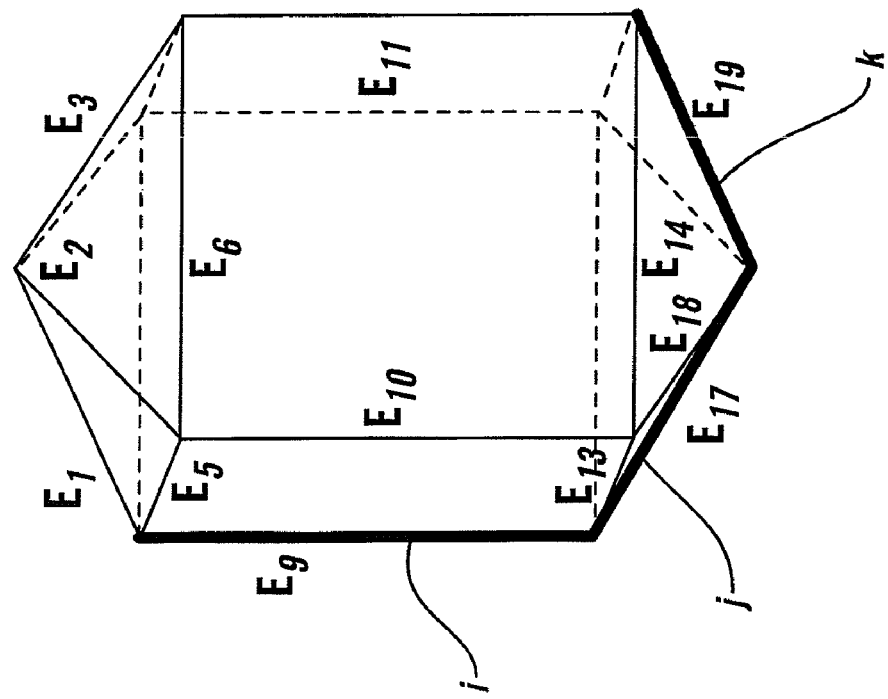
FIG. 36 shows a second hypothesis for fitting the model of the object to be located to the viewpoint-invariant line group shown in FIG. 33.
Figure 35:
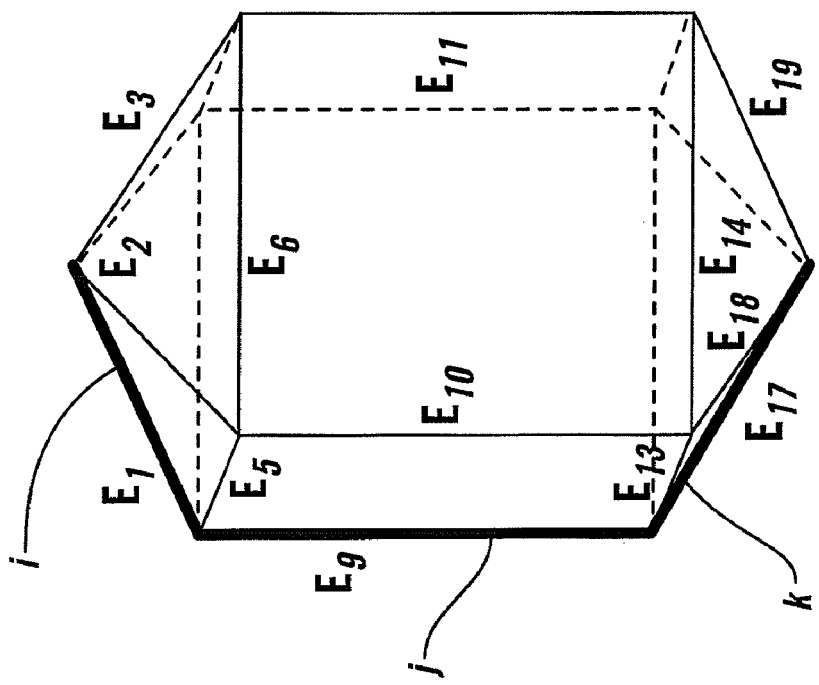
FIG. 35 shows a first hypothesis for fitting the wire model of a particular object to the viewpoint-invariant line group shown in FIG. 33.

FIGS. 35 and 36 show two different possibilities, or hypotheses, for how the edges i, j and k of the viewpoint-invariant line group shown in FIG. 33 correspond to the visible edges of a glycine-shaped wireframe model. In FIGS. 35 and 36, each of the visible edges E in the wireframe glycine model are labeled. In FIG. 35, a first hypothesis associates the line i of the selected viewpoint independent line group shown in FIG. 33 with the edge E1, the line j with the edge E9 and the line k with the edge E17. As shown in FIG. 36, a second hypothesis associates the line i of the viewpoint-invariant line group shown in FIG. 33 with the edge E9, the line j with the edge E17 and the line k with the edge E19. As outlined above, because multiple correspondences between the selected viewpoint-invariant line group and each of the one or more wireframe models are possible, in various exemplary embodiments according to this invention, multiple hypothesis may be generated as needed for a particular viewpoint-invariant line group.

For each such hypothesis, the viewpoint parameters must be estimated, a process also referred to as the pose estimation or the alignment. While this has been studied extensively in the prior art, such prior art methods assume that the internal model parameters are already known. However, as outlined above, because the sizes as well as the orientation of the objects are not known, such prior art models are not particularly useful. In contrast, in various exemplary embodiments according to this invention, the internal model parameters to be used in a particular hypothesis are estimated using the properties of the located lines that form the viewpoint-invariant line group, along with at least one assumed orientation of the object in the camera-centered coordinate system.

As outlined above, for the glycine-shaped object to be recognized, there are three internal model parameters, the height h along the edges E9-E11, the width w along the edges E5, E6, E13 and E14, and the height t of the pyramid perpendicular to the lines E5, E6, E13 or E14. For example, given the first hypothesis shown in FIG. 35, the model height h is estimated as $l_j \cos\theta_x$, while the width w is estimated as $$2\cos\theta_y(\max(|\hat{t}_i \cdot \hat{t}_j^\perp|, |\hat{t}_k \cdot \hat{t}_j^\perp|)) \quad (19)$$

where $\theta_y$ and $\theta_x$ are assumed orientations in depth; and $\hat{t}_j^\perp$ is a unit vector perpendicular to $\hat{t}_j$.

The pyramid height t is estimated as $w \tan(\alpha/2)$, where a is assumed to be 45 degrees.

It should be appreciated that, despite being based on several assumptions, few if any of which are likely to be completely accurate, such parameter estimates provide a useful starting point for fitting the model to the lines forming the viewpoint-invariant line group. It should also be appreciated that, given the correspondences, the assumed orientations in depth and the model parameters, the remaining model viewpoint parameters are estimated in a fairly straight-forward manner.

First, as outlined above in FIG. 9 and as shown in FIG. 37, the three-dimensional model is projected on to the image plane using Eqs. (15)-(17), assuming $\theta_z$, $t_x$ and $t_y$ are equal to zero. Next, in various exemplary embodiments, the in-plane orientation $\theta_z$ is estimated using a weighted average of the orientation differences between the lines of the viewpoint-invariant line group and the corresponding projected model lines, i.e., model lines $E_1$, $E_9$ and $E_{17}$, projected onto the image plane, for hypothesis 1 and lines $E_9$, $E_{17}$ and $E_{19}$, projected onto the image plane, for hypothesis 2. Accordingly, the assumption that $\theta_z$ is equal to zero can be relaxed. In particular, in various exemplary embodiments, based on the now-estimated in-plane orientation $\theta_z$ the three-dimensional model is once again projected into the image plane. Based on the re-projected model lines, the translations $t_x$ and $t_y$ are estimated from a weighted average of the spatial differences between the midpoints of the model lines and the midpoints of the corresponding lines of the selected viewpoint-invariant line group for the particular hypothesis.

The re-projected and translated model lines that do not correspond to the lines of the selected viewpoint-invariant line group, for a given hypothesis, then form a set of projected model lines $E^P$ that can be compared directly with the remaining located lines in a set of located lines. In particular, in various exemplary embodiments, the additional model edge-located line correspondences are identified based on the parallelism between the model edges $E^P$ and located lines that are spatially adjacent to the corresponding projected model edges. FIGS. 17 and 18 outline one exemplary embodiment of determining which adjacent located lines best match the projected model lines $E^P$.

Once any additional corresponding located lines are associated with the additional projected model lines $E^P$ for the particular hypothesis, a verification score can be associated with that hypothesis. The verification score quantifies the amount of evidence in an image that supports the accuracy of a given correspondence hypothesis. In various exemplary embodiments, the verification score is determined as the percentage of visible model line length for the projected and translated model edges E that are associated with corresponding located lines. It should be appreciated that more advanced methods for determining the verification score can be used. It should also be appreciated that a verification score threshold can be used to filter out any hypothesis that, while providing the highest verification score for a particular viewpoint independent line group, still is not sufficiently high to indicate confidence that the viewpoint independent line group actually corresponds to an object appearing in the obtained image.

Once a hypothesis is identified that has a verification score that is better than any other hypothesis for that viewpoint-invariant line group and that is greater than the verification score threshold, the mismatch between the corresponding model and all of the associated or corresponding data lines is then adjusted, minimized and/or optimized. In various exemplary embodiments, this can be done by solving the optimization problem:

$$\min_{p} \phi = \sum_{i \in M} l_i(e_{1i} + e_{2i})^2, \quad (20)$$

where:

M is the set of data lines for which a correspondence has been identified;

p is the parameter vector;

$l_i$ is the length of a particular located line i; and $e_{1i}$ and $e_{2i}$ are the perpendicular distances from the endpoints $e_1$ and $e_2$ of the ith located line to the corresponding model line.

Figure 38:
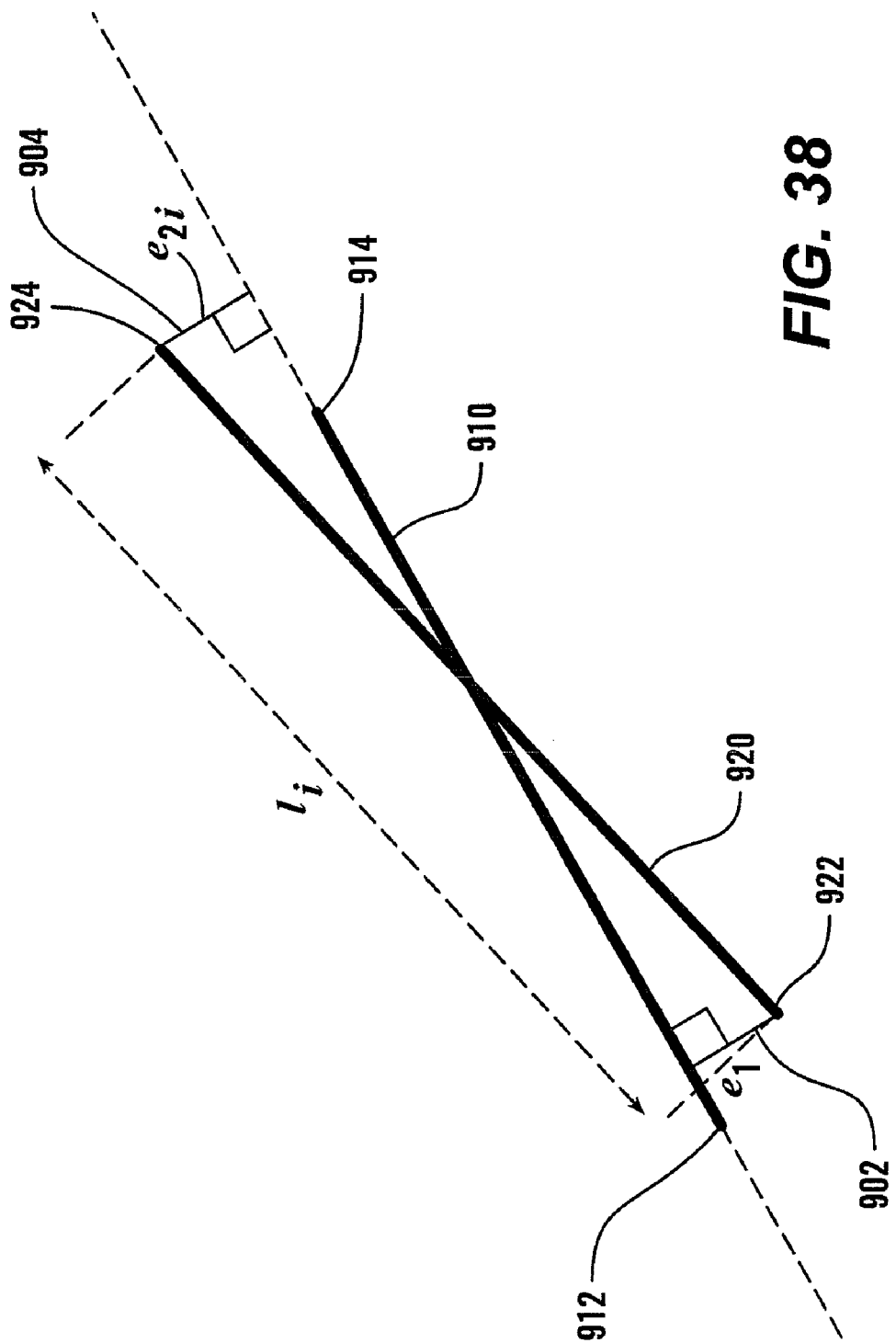
FIG. 38 illustrates one exemplary embodiment of a method for determining which located lines correspond to edges of the projected model.

This is shown in FIG. 38. In particular, FIG. 38 shows the relationship between a model line 910 and a located line 920. The model line 910 includes endpoints 912 and 914, while the located line includes endpoints 922 and 924. FIG. 38 also shows the length $l_i$ of the located line 920 and the distances $e_{1i}$ and $e_{2i}$ of the endpoints 922 and 924 of the located line 920 to the corresponding model line 910. The parameter vector p for the glycine model shown in FIGS. 27, 35 and 36 is:

$$p = |h w t \theta_x \theta_y \theta_z t_x t_y| \quad (21)$$

Of course it should be appreciated that the optimization problem set forth in Eq. (21) is subject to the model and imaging constraints set forth in Eq. (15)-(17).

As set forth above with respect to FIG. 9, once the model is adjusted, optimized or the like, any other viewpoint-invariant line groups that remain in the list of identified viewpoint-invariant line groups and which overlap the adjusted projected object model are removed from further consideration. This is done because an assumption is made that only a single crystal appears within the bounds of any adjusted projected object model. That is, an assumption is made that each line within the bounds of the image can be attributed to only one crystal. Thus, once a model is successfully fit to a set of located lines, any viewpoint-invariant line groups that contain one or more of those lines are considered invalid. Furthermore, it is assumed that any line completely contained within the adjusted projected model of an identified object arises due to unmodeled features of that crystal. Thus, any viewpoint-invariant line group that contains one or more such lines is considered invalid.

Figure 39:
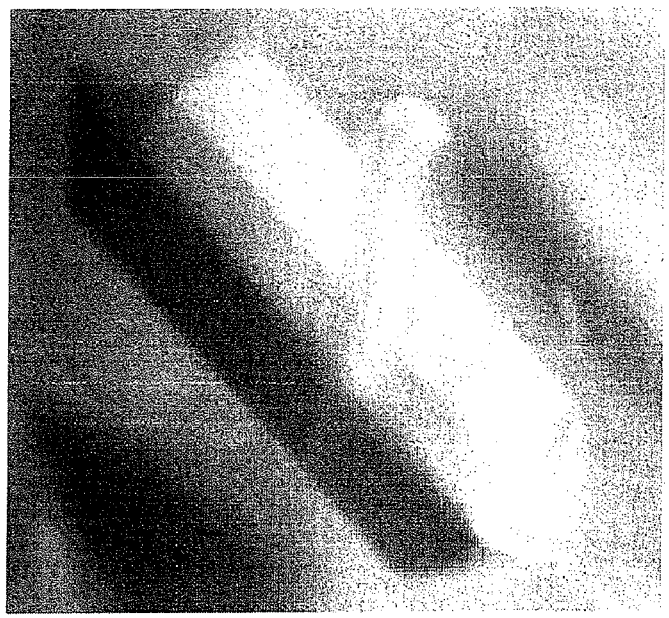
FIG. 39 shows a portion of an exemplary image, that can be analyzed using systems and methods according to this invention, that contains at least one instance of an object to be located in the image.
Figure 40:
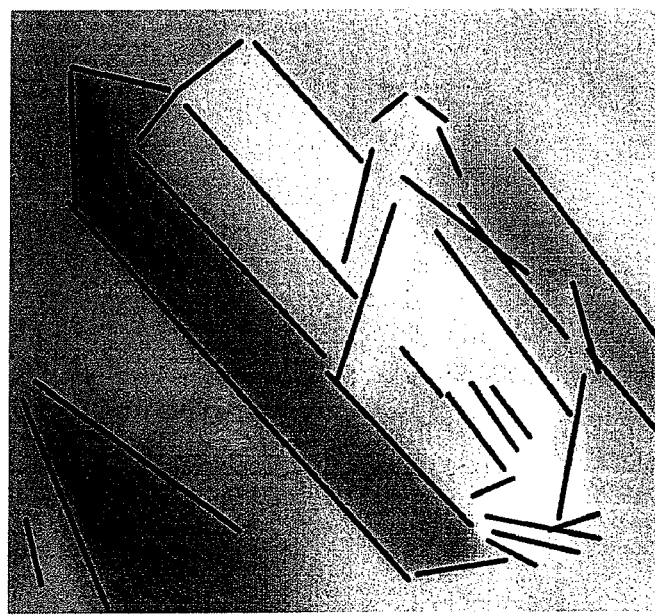
FIG. 40 shows the linear features identified by analyzing the image portion shown in FIG. 39.
Figure 41:
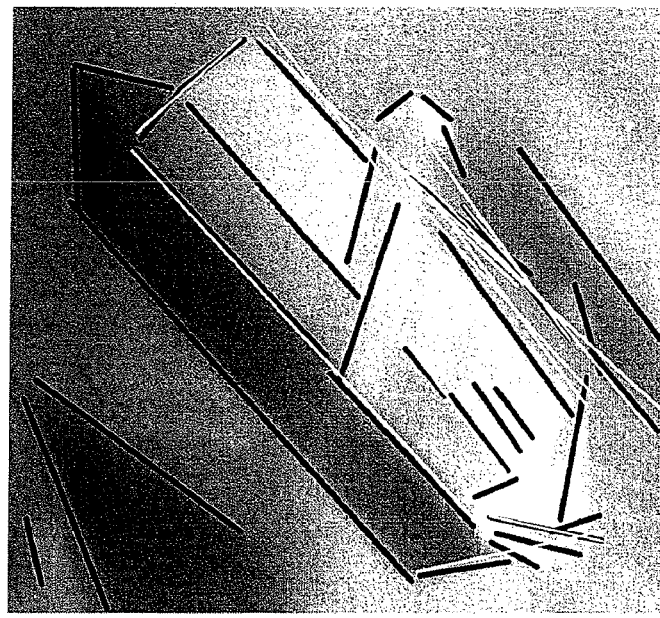
FIG. 41 illustrates the virtual lines created by analyzing the linear features shown in FIG. 40.

FIGS. 39-46 illustrate the above-outlined exemplary embodiment of a method according to this invention. In particular, FIG. 39 shows a portion of an exemplary obtained image of glycine crystals. FIG. 40 shows a set of linear features identified by analyzing the image shown in FIG. 39 as outlined above. FIG. 41 shows one exemplary embodiment of generating virtual lines by identifying any potential co-linear lines that represent a single edge of the object in the image.

Figure 42:
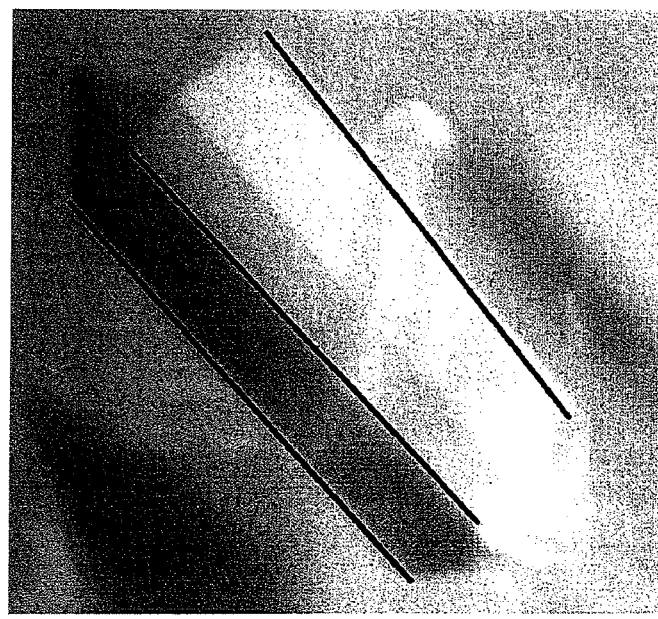
FIG. 42 shows a selected parallel-type viewpoint-invariant line group selected from the linear features and virtual lines shown in FIG. 39.
Figure 43:
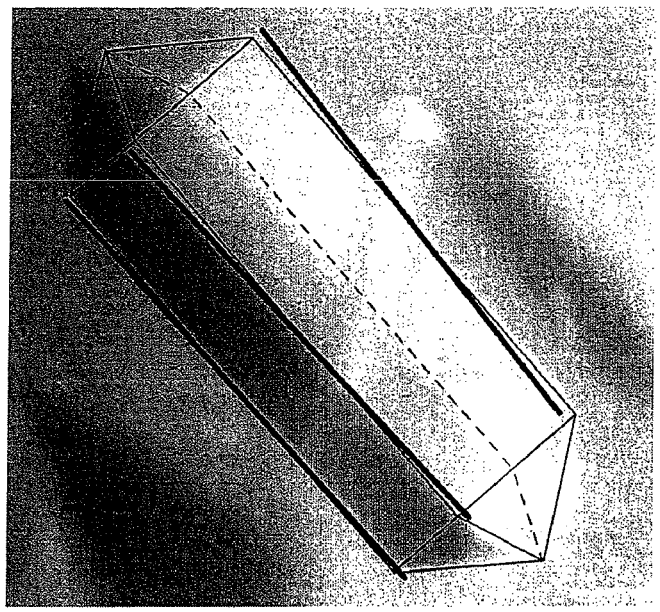
FIG. 43 shows a first hypothesis for fitting the model of the object to be identified to the viewpoint-invariant line group shown in FIG. 42.
Figure 44:
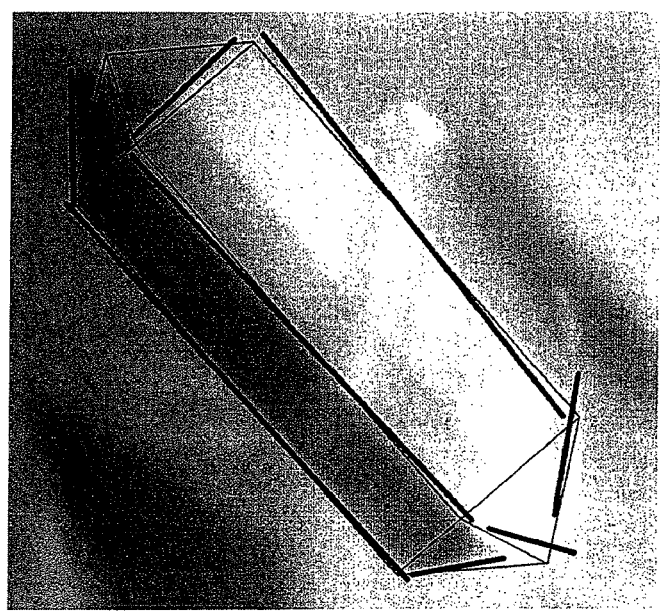
FIG. 44 shows one exemplary embodiment of a projection of the fit and parameterized model shown in FIG. 43 onto the image plane and various additional ones of the lines shown in FIG. 41 that have been matched to other edges in the projected model.

FIG. 42 is one exemplary embodiment of a most visually salient viewpoint independent line group of all of the viewpoint-invariant line groups that occur in the set of located linear features and generated virtual lines shown in FIG. 41. In particular, this viewpoint-invariant line group is a three-line parallel viewpoint-invariant line group. FIG. 43 shows the projection of the glycine wireframe model shown in FIG. 27 onto the image plane. In particular, the projected wireframe model shown in FIG. 43 has already been re-projected and translated as outlined above. FIG. 44 shows additional ones of the lines shown in FIG. 41 that meet the parallelism requirements for various ones of the edges of the projected model that do not correspond to the three-line parallel viewpoint-invariant line group. FIG. 44 also shows the adjusted, re-projected wireframe model for the glycine crystal that has been adjusted based on all of the located lines.

Figure 45:
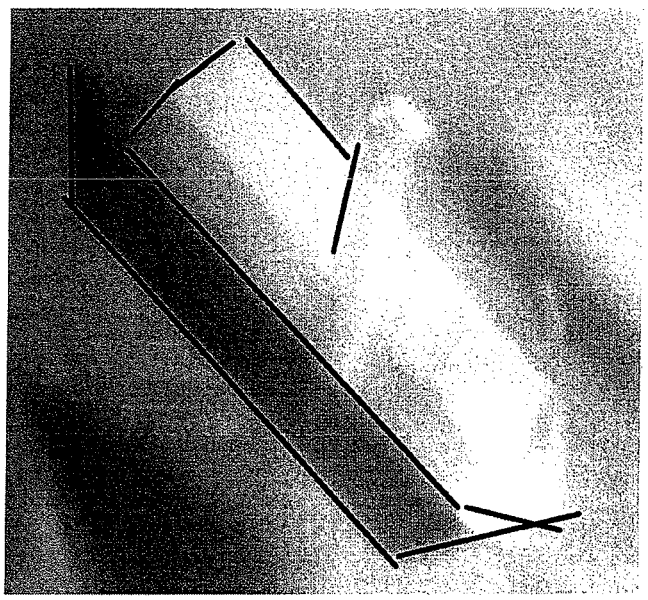
FIG. 45 shows one exemplary embodiment of identifying located lines which are to be removed from the set of located lines based on their location relative to the located object shown in FIG. 44.
Figure 46:
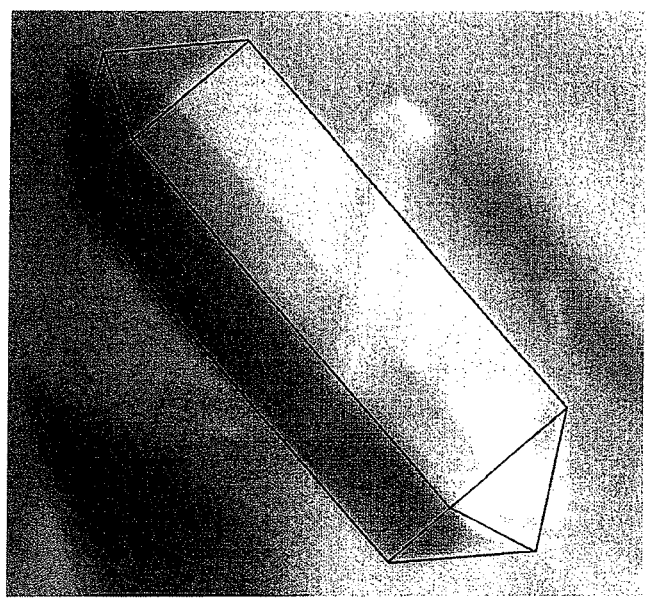
FIG. 46 shows the object shown in FIG. 39 with an optimized object model fit to it.

FIG. 45 shows one exemplary embodiment of some additional viewpoint-invariant line groups that share at least one line with the set of lines shown in FIG. 44 that are associated with the projected glycine model. These additional viewpoint-invariant line groups, along with any other lines that are wholly within the bounds of the projected glycine wireframe model, are removed from further consideration of the lines and viewpoint-invariant line groups of, or obtained from analyzing, the set of linear features and virtual lines shown in FIG. 41. FIG. 46 shows the adjusted projected wireframe model superimposed over the located glycine crystal shown in FIG. 39.

While this invention has been described in conjunction with the exemplary embodiments outlined above, various alternatives, modifications, variations, improvements and/or substantial equivalents, whether known or that are or may be presently foreseen, may become apparent to those having at least ordinary skill in the art. Accordingly, the exemplary embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

What is claimed is:

1. A system for identifying an object appearing in an image, the image having a plurality of pixels, each pixel having an image value, and containing at least one object of at least one type of object to be identified, each type of object to be identified represented by a 3-dimensional model, each 3-dimensional model including edges and spatial relationships between the edges, the system comprising:

a logic circuit configured to analyze the plurality of pixels to determine a plurality of line-like features in the image, group at least some of the line-like features into at least one viewpoint-invariant line group, each viewpoint-invariant line group corresponding to at least one spatial relationship between edges of at least one of the 3-dimensional models, analyze at least one determined viewpoint-invariant line group to identify, for each such determined viewpoint-invariant line group, a 2-dimensional projection of one of the at least one 3-dimensional models that corresponds to that determined viewpoint-invariant line group, and identify, for at least one determined viewpoint-invariant line group for which there is a 2-dimensional projection of one of the at least one 3-dimensional models, the viewpoint-invariant line group as corresponding to an object appearing in the image.

2. The system of claim 1, wherein there are a plurality of objects in the image, the objects having at least one parameter and being involved in a process having at least one controllable process parameter, the logic circuit further configured to repeat the at least one determined viewpoint-invariant line group analyzing step and the identifying step to determine a plurality of viewpoint-invariant line groups that each corresponds to one of the plurality of objects appearing in the image, fit, for each determined viewpoint-invariant line group that corresponds to an object appearing in the image, the 3-dimensional model for that object to the viewpoint-invariant line group based on the 2-dimensional projection, determine, for each object appearing in the image, at least one parameter for that object based on the fitted 3-dimensional model for that object, and control at least one of the at least one controllable process parameter based on at least one of the at least one parameter determined from the determined objects.

3. The system of claim 1, wherein the logic circuit is configured to analyze the plurality of pixels to determine a plurality of line-like features in the image by analyzing the plurality of pixels of the obtained image to locate linear features occurring within the image, analyzing the located linear features at least to identify pairs of located linear features that are sufficiently co-linear, generating virtual lines for at least some pairs of located linear features that are sufficiently co-linear, wherein the line-like features include the located linear features and the generated virtual lines.

4. The system of claim 1, wherein the logic circuit is configured to analyze at least one determined viewpoint-invariant line group to identify, for each such determined viewpoint invariant line group, a 2-dimensional projection of one of the at least one 3-dimensional models that corresponds to that determined viewpoint-invariant line group by selecting one of at least one determined viewpoint-invariant line group, determining, for the selected viewpoint-invariant line group and for each of at least one of the 3-dimensional models, at least one hypothesis for how the line-like features of the selected viewpoint-invariant line group correspond to edges of that 3-dimensional model, determining, for each determined hypothesis, a 2-dimensional projection of the 3-dimensional model of that hypothesis based on the corresponding selected viewpoint-invariant line group, determining, for each determined hypothesis, if any other line-like features appearing in the image match visible edges of the 2-dimensional projection determined for that hypothesis, associating, for each determined hypothesis, each such matching linelike feature with that hypothesis, and determining a score for each determined hypothesis based on the selected viewpoint-invariant line group and any matching line-like features associated with that hypothesis.

5. The system of claim 4, wherein the logic circuit is configured to identify, for at least one determined viewpoint-invariant line group that corresponds to a 2-dimensional projection of one of the at least one 3-dimensional models, the viewpoint-invariant line group as an object appearing in the image by selecting, for a selected viewpoint-invariant line group, a hypothesis associated with the viewpoint-invariant line group that has a highest score as the selected hypothesis for the selected viewpoint-invariant line group, determining if the selected hypothesis has a score at least equal to a score threshold, discarding, if the score is not at least equal to the score threshold, the selected viewpoint-invariant line group, and identifying, if the score is at least equal to the score threshold for the selected hypothesis, the selected viewpoint-invariant line group and any matching other line-like features as an object appearing in the image.

6. The system of claim 5, wherein the logic circuit is further configured to determine, if the score is at least equal to the score threshold, if any other viewpoint-invariant line groups and/or any other line-like features sufficiently overlap the 2-dimensional projection of the 3-dimensional model of that hypothesis into the image, remove from further consideration any determined other viewpoint invariant line groups and any other line-like features that sufficiently overlap the 2-dimensional projection of the 3-dimensional model of that hypothesis into the image, and repeat the viewpoint-invariant line group selecting step through the determined other viewpoint-invariant line groups and other line-like features removing step for at least one additional viewpoint-invariant line group.

7. The system of claim 5, wherein the logic circuit is further configured to, if the score is not at least equal to the score threshold, repeat the viewpoint-invariant line group selecting step through the selected hypothesis having a score at least equal to a score threshold determining step for at least one additional viewpoint-invariant line group.

8. The system of claim 5, wherein the logic circuit is further configured to repeat, after either the discarding step, the selecting step in response to the selected hypothesis having a score at least equal to a score threshold determining step for at least one additional viewpoint-invariant line group.

9. The system of claim 1, further including an image capture device configured to obtain an image comprising the plurality of pixels having image values.

10. A system for identifying an object appearing in an image having a plurality of pixels, the system comprising:
a logic circuit configured to
determine a plurality of line-like features in the image based on pixels in the image,
group at least two of the line-like features into at least one viewpoint-invariant line group that corresponds to at least one spatial relationship between edges of a 3-dimensional model representing a type of object to be identified,
use the viewpoint-invariant line group to identify a 2-dimensional projection of the 3-dimensional model that corresponds to the viewpoint-invariant line group, and
in response to the identified 2-dimensional projection, identify the viewpoint-invariant line group as corresponding to an object appearing in the image.

11. The system of claim 10, wherein the logic circuit is configured to group the at least two of the line-like features by grouping the at least two of the line-like features into at least one viewpoint-invariant line group that corresponds to at least one spatial relationship between edges of a 3-dimensional including edges and spatial relationships between the edges.

12. The system of claim 10, wherein the logic circuit is configured to group the at least two of the line-like features by grouping the at least two of the line-like features based upon a known spatial relationship expected for the object being imaged.

13. The system of claim 10, wherein the logic circuit is configured to identify the viewpoint-invariant line group as corresponding to an object appearing in the image by identifying the viewpoint-invariant line group as corresponding to a known object having a spatial relationship corresponding to the 3-dimensional model.

14. The system of claim 10, wherein the logic circuit is configured to control at least one controllable process parameter for processing the object to which the viewpoint-invariant line group has been identified as corresponding to.

15. The system of claim 10, wherein the logic circuit is configured to identify the viewpoint-invariant line group as corresponding to an object appearing in the image by
determining, for the viewpoint-invariant line group and for the 3-dimensional model, an hypothesis that characterizes correspondence between the line-like features of the selected viewpoint-invariant line group and edges of the 3-dimensional model,
determining a 2-dimensional projection of the 3-dimensional model of the hypothesis based on the viewpoint-invariant line group,
determining whether any other line-like features appearing in the image match visible edges of the 2-dimensional projection,
associating each matching line-like feature with the hypothesis,
determining a score for the hypothesis based on the viewpoint-invariant line group and any matching line-like features associated with the hypothesis, and
in response to the score being at least equal to a score threshold, identifying the viewpoint-invariant line group and any matching line-like features as corresponding to an object appearing in the image.

16. The system of claim 10, wherein the logic circuit is configured to identify the viewpoint-invariant line group as corresponding to an object appearing in the image by
determining, for the viewpoint-invariant line group and for the 3-dimensional model, a plurality of hypotheses that characterize correspondence between the line-like features of the selected viewpoint-invariant line group and edges of the 3-dimensional model,
determining a 2-dimensional projection of the 3-dimensional model of each hypothesis based on the viewpoint-invariant line group,
for each hypothesis, determining whether any other line-like features appearing in the image match visible edges of the 2-dimensional projection,
for each hypothesis, associating each matching line-like feature with the hypothesis,
determining a score for each hypothesis based on the viewpoint-invariant line group and any matching line-like features associated with the hypothesis, and
for the highest-scoring hypothesis, identifying the viewpoint-invariant line group and any matching line-like features for the hypothesis as corresponding to an object appearing in the image.

17. A non-transitory computer readable medium having stored thereon software for characterizing objects in an image, comprising:
instructions for determining a plurality of line-like features in the image based on pixels in the image;
instructions for grouping at least two of the line-like features into at least one viewpoint-invariant line group that corresponds to at least one spatial relationship between edges of a 3-dimensional model representing a type of object to be identified;
instructions for using the viewpoint-invariant line group to identify a 2-dimensional projection of the 3-dimensional model that corresponds to the viewpoint-invariant line group; and
instructions for identifying the viewpoint-invariant line group as corresponding to an object appearing in the image, in response to the identified 2-dimensional projection.

18. The computer readable medium of claim 17, wherein the instructions for grouping the at least two of the line-like features include instructions for grouping the at least two of the line-like features into at least one viewpoint-invariant line group that corresponds to at least one spatial relationship between edges of a 3-dimensional including edges and spatial relationships between the edges.

19. The computer readable medium of claim 17, wherein the instructions for grouping the at least two of the line-like features include instructions for grouping the at least two of the line-like features based upon a known spatial relationship expected for the object being imaged.

20. The computer readable medium of claim 17, wherein the instructions for identifying the viewpoint-invariant line group as corresponding to an object appearing in the image include instructions for identifying the viewpoint-invariant line group as corresponding to a known object having a spatial relationship corresponding to the 3-dimensional model.

21. The computer readable medium of claim 17, further including instructions for controlling at least one controllable process parameter for processing the object to which the viewpoint-invariant line group has been identified as corresponding to.

22. The computer readable medium of claim 17, wherein the instructions for identifying the viewpoint-invariant line group as corresponding to an object appearing in the image include instructions for
- determining, for the viewpoint-invariant line group and for the 3-dimensional model, an hypothesis that characterizes correspondence between the line-like features of the selected viewpoint-invariant line group and edges of the 3-dimensional model,
- determining a 2-dimensional projection of the 3-dimensional model of the hypothesis based on the viewpoint-invariant line group,
- determining whether any other line-like features appearing in the image match visible edges of the 2-dimensional projection,
- associating each matching line-like feature with the hypothesis,
- determining a score for the hypothesis based on the viewpoint-invariant line group and any matching line-like features associated with the hypothesis, and
- in response to the score being at least equal to a score threshold, identifying the viewpoint-invariant line group and any matching line-like features as corresponding to an object appearing in the image.

23. The computer readable medium of claim 17, wherein the instructions for identifying the viewpoint-invariant line group as corresponding to an object appearing in the image include instructions for
- determining, for the viewpoint-invariant line group and for the 3-dimensional model, a plurality of hypotheses that characterize correspondence between the line-like features of the selected viewpoint-invariant line group and edges of the 3-dimensional model,
- determining a 2-dimensional projection of the 3-dimensional model of each hypothesis based on the viewpoint-invariant line group,
- for each hypothesis, determining whether any other line-like features appearing in the image match visible edges of the 2-dimensional projection,
- for each hypothesis, associating each matching line-like feature with the hypothesis,
- determining a score for each hypothesis based on the viewpoint-invariant line group and any matching line-like features associated with the hypothesis, and
- for the highest-scoring hypothesis, identifying the viewpoint-invariant line group and any matching line-like features for the hypothesis as corresponding to an object appearing in the image.

* * * * *

UNITED STATES PATENT AND TRADEMARK OFFICE
CERTIFICATE OF CORRECTION

PATENT NO. : 8,204,302 B2  
APPLICATION NO. : 13/047491  
DATED : June 19, 2012  
INVENTOR(S) : Larsen et al.

Page 1 of 1

It is certified that error appears in the above-identified patent and that said Letters Patent is hereby corrected as shown below:

In the Specification

Col. 32, line 1: "180° C." should read --180°.--.

Col. 32, line 3: "180° C.," should read --180°,--.

Signed and Sealed this  
Thirtieth Day of September, 2014

Michelle K. Lee  
*Deputy Director of the United States Patent and Trademark Office*